US008221979B2

(12) United States Patent
Gelb et al.

(10) Patent No.: US 8,221,979 B2
(45) Date of Patent: Jul. 17, 2012

(54) COMPOSITIONS AND METHODS FOR DETECTING NOONAN SYNDROME

(75) Inventors: Bruce D. Gelb, New York, NY (US); Marco Tartaglia, Rome (IT); Len Pennacchio, Walnut Creek, CA (US)

(73) Assignees: Mount Sinai School of Medicine, New York, NY (US); The Regents of the University of California, Oakland, CA (US)

( * ) Notice: Subject to any disclaimer, the term of this patent is extended or adjusted under 35 U.S.C. 154(b) by 405 days.

(21) Appl. No.: 12/443,752

(22) PCT Filed: Nov. 16, 2007

(86) PCT No.: PCT/US2007/085005
§ 371 (c)(1),
(2), (4) Date: Mar. 31, 2009

(87) PCT Pub. No.: WO2008/061239
PCT Pub. Date: May 22, 2008

(65) Prior Publication Data
US 2010/0009361 A1    Jan. 14, 2010

Related U.S. Application Data

(60) Provisional application No. 60/866,204, filed on Nov. 16, 2006.

(51) Int. Cl.
*C12Q 1/68* (2006.01)
*C12P 19/34* (2006.01)
*C07H 21/02* (2006.01)
*C07H 21/04* (2006.01)

(52) U.S. Cl. ...... 435/6.11; 435/6.1; 435/6.12; 435/6.17; 435/91.2; 536/23.5; 536/24.31; 536/24.33

(58) Field of Classification Search .................. None
See application file for complete search history.

(56) References Cited

U.S. PATENT DOCUMENTS
2010/0227778 A1* 9/2010 Neel et al. .................... 506/23

OTHER PUBLICATIONS

Lepri et al. Human Mutation. 2011. 32: 760-772.*
Hirschhorn et al. Genetics in Medicine. vol. 4, No. 2, pp. 45-61, Mar. 2002.*
Ioannidis et al. Nature genetics (2001) 29:306-309.*
Lucentini et al. The Scientist (2004) vol. 18, p. 20.*
Pandit, et al. "Gain-of-function RAF1 mutations cause Noonan and LEOPARD syndromes with hypertrophic cardiomyopathy". Nature Genetics, Advance Online Publication, Jul 1, 2007. DOI: 10.1038/ng2073.
NCBI SNP Database, National Center for Biotechnology Information, National Library of Medicine, NIH (Bethesda, MD, USA). Aug. 6, 2003, rs8192671, ss12587263.
NCBI SNP Database, National Center for Biotechnology Information, National Library of Medicine, NIH (Bethesda, MD, USA). Jul. 12, 2002. rs3730271, ss4916225.
Hart et al., "A Mutation in the SOS1 Gene Causes Heredity Gingival Fibromatosis Type 1," Am. J. Human Genetics, vol. 70, pp. 943-954 (2002).
Pandit et al., "Gain-of-function RAF1 mutations cause Noonan and LEOPARD syndromes with hypertrophic cardiomyopathy," Nat. Genet., vol. 39, No. 8, pp. 1007-1012 (2007).
PCT/US07/076248: International Preliminary Report on Patentability dated Mar. 5, 2009 (8 pages).
PCT/US07/076248: International Search Report and Written Opinion of the International Searching Authority dated Sep. 30, 2008 (10 pages).
PCT/US07/085005: International Preliminary Report on Patentability dated May 28, 2009 (7 pages).
PCT/US07/085005: International Search Report dated Sep. 30, 2008 (7 pages).
PCT/US07/085005: Written Opinion of the International Searching Authority dated Sep. 30, 2008 (6 pages).
Razzaque et al., "Germline gain-of-function mutations in IRAF1i cause Noonan syndrome," Nature Genetics, vol. 39, No. 8, pp. 1013-1017 (2007).
Roberts et al., "Germline Gain-of-Function Mutations in SOS1 Cause Noonan Syndrome," Nature Genetics, vol. 39, No. 1, pp. 70-74 (2007).
Tartaglia et al., "Gain of Function SOS1 Mutations Cause Distinctive From of Noonan Syndrome," Nature Genetics, vol. 39, No. 1, pp. 75-79 (2007).
Zenker et al., "SOS1 is the Second Most Common Noonan Gene But Plays No Major Role in Cardio-Facio-Cutaneous Syndrome," J. Med. Genetics, vol. 44, pp. 651-656 (2007).
EP Application No. 07864549.6: Search Report dated Jan. 29, 2010 (3 pages).
PCT/US07/85005: International Search Report dated Sep. 30, 2008 (7 pages).

* cited by examiner

*Primary Examiner* — Carla Myers
(74) *Attorney, Agent, or Firm* — Troutman Sanders LLP

(57) ABSTRACT

Diagnostic and therapeutic applications for Noonan Syndrome are described. The diagnostic and therapeutic applications are based on certain mutations in a RAS-specific guanine nucleotide exchange factor gene SOS1 or its expression product. The diagnostic and therapeutic applications are also based on certain mutations in a serine/threonine protein kinase gene RAF1 or its expression product thereof. Also described are nucleotide sequences, amino acid sequences, probes, and primers related to RAF1 or SOS1, and variants thereof, as well as host cells expressing such variants.

6 Claims, 30 Drawing Sheets

SOS1 (Genomic) – SEQ ID NO:6

| Gene | SOS1 | Variant 1 |
|---|---|---|
| DNA : | 134.60 Kb | NT_022184 |
| mRNA : | 4002 bp | NM_005633 |
| CDS : | 4002 bp | NP_005624 |

| NON CODANT MRNA | CDS | initiator and stop codon | genomic and intronic adjacent sequences | allelic variation |
|---|---|---|---|---|

EXON 1 87 bp (SEQ ID NO: 85)
tccacggctggtacctgtgtcgggtgggtggccaggcgcgggcctcgcccccagcccc
ctcgccagggctagcccggctgcgcggcgcccggagggggccggccgtccggtgggc
cgcggccctgttccgcgctgcgagctcgccctctcgcggctccctggccggccgccgc
cgcccctctccccgccagaggcgccccgggggcacc**ATGCAGGCGCAGCAGCTGCCCT
ACGAGTTTTTCAGCGAAGAGAACGCGCCCAAGTGGCGGGGACTACTGGTGCCTGCGCTG
AAAAAG**gtgaggagcacgcgggacccgcttccggccgcagcccccagcgcgggcgc
tggggaagggctggggaggcggggcgcgcgcagggccgtctttcttccggtctcgccg
cgtctccaaaaggacggcgcacacggagaggccccctcatacggctggctctcggtgt
tgacatcca EXON 2 126 bp (SEQ ID NO: 86)
ttggccagggtggtctcaaactcctgacctcaggtgatctgcccgccttggcctcccag
agtgctggcattacaggcatgagccaccctgcccggccacaaaccacatttttaaag
ttttaaaaatttgtttaatgatatggaacccacattttaattactttgcttttgttta
tag**GTCCAGGGGCAAGTTCATCCTACTCTCGAGTCTAATGATGATGCTCTTCAGTATGT
TGAAGAATTAATTTTGCAATTATTAAATATGCTATGCCAAGCTCAGCCCCGAAGTGCTT
CAGATGTAGAG**gtatgacaaatgttgtcttgtatttactttatatctaatttgtgtgtt
ggttgtaatgtcagtgaacagggaaagaatttgctctctctatatatatggtatataag
aaaatgaagcctggatttaactctttacaggttgagtatcccttatccagaatgcttgg
gaacagaagtgttt EXON 3 132 bp (SEQ ID NO: 87)
attaaggaactaatacattgacaattactgtttctcttagcttcatatgtttgtaatg
taaattataccacatgtgaaaagctctacttttggtattctttgatttaaaagtaaat
tttaagtgaagagcactatttaatatatttttgcttagttgttattttcctatttcc
aag**GAACGTGTTCAAAAAGTTTCCCTCATCCAATTGATAAATGGGCAATAGCTGATGC
CCAATCAGCTATTGAAAAGAGGAAGCGAAGAAACCCTTTATCTCTCCCAGTAGAAAAAA
TTCATCCTTTATTAAAG**gtaatgctgaactactgccttcttgccttttaagggaaaaat
aaaacccaccattttttatacaataagaatatatttatggataattgagtcaactaag
agtaaaattctctcattctaagttttccagagatttatgtggtgagaagggatgctatg
ataataagaaaatataaact

Figure 5A-1

EXON 4  165 bp (SEQ ID NO: 88)
ttttcaatagtaatacatatattattcattgttgaaccacttacaattaaatgttgttg
gtaagcacaggcctcaggaaaaaagtgtaagttaaggtgcaaatatgttttttatttt
taatcagtgtgttaaatgtacagtatatgatgtttaaacatgcttttcttttaattttg
cag**GAGGTCCTAGGTTATAAAATTGACCACCAGGTTTCTGTTTACATAGTAGCAGTCTT
AGAATACATTTCTGCAGACATTTTAAAGCTGGTTGGGAATTATGTAAGAAATATACGGC
ATTATGAAATTACAAAACAAGATATTAAAGTGGCAATGTGTGCTGACAAG**gtaggaaac
tgagcttttctattttttttcttaagtttcttttttatgacttattagatgctaacgtact
attcatatagaataaaattgtattatgtgttggggaatatctccagtaacctaatagta
gggattcaagataccactttatagaaataagacattagatatataatattaaa EXON 5  210 bp (SEQ ID NO: 89)
tgttgaattctgttttagagaagctgtggagggatgctggcaatatatccaagaagaga
aatttgtttgtctgcttttttatcatttaagaactttattcagagaacttagagcattt
cacatcaaattctacgaaagcttcatatttttattatacttttttatatctctgactgta
tag**GTATTGATGGATATGTTTCATCAAGATGTAGAAGATATTAATATATTATCTTTAAC
TGACGAAGAGCCTTCCACCTCAGGAGAACAAACTTACTATGATTTGGTAAAAGCATTTA
TGGCAGAAATTCGACAATATATAAGGGAACTAAATCTAATTATAAAAGTTTTTAGAGAG
CCCTTTGTCTCCAATTCAAAATTGTTTTCAGCTAAT**gtaagtatcattgtatatatgcc
tctcattgaatgtgttgtgaaatttgcatgaccacttcaaatttgaagttgtacagttc
atcattactaatttgttaattttttttaagttgtgggacttaattcatgatcacaaagtt
ttacaacagtttcaagagatttaacattagaaattaaga EXON 6  144 bp (SEQ ID NO: 90)
cactgacctagagaaatgtatttgcaaattgtacacctttgcagaaggaattcttgaat
tgtcctttattcatatttctaagtcattaaaattttttcactgtgtctgacatgttaaat
tttgtgattataaaatgacttattggctcaaaatttgtttaatattataataatacagc
ctcactgaattaatgtgttttcccccaaacag**GATGTAGAAAATATATTTAGTCGCATA
GTAGATATACATGAACTTAGTGTAAAGTTACTGGGCCATATAGAAGATACAGTAGAAAT
GACAGATGAAGGCAGTCCCCATCCACTAGTAGGAAGCTGCTTTGAAGACTTAGCAGAG**g
taagtacttcaattatatacccgaaaagtctgcataaaagcctacatttacattaaaat
tgagagtcttacttctttccagctaaagtcatagatactaattgttgactatttatctg
ttattgctccttttttcatagggtcattgtcaacatatgtttctgttatcttagcaaaca
ga EXON 7  111 bp (SEQ ID NO: 91)
tctcttacttgagaatattgggatctcttctattaaaattataattagtagtcatataa
ttttttgcttagagactttcaaagacatacataattgtgctcgcatagtcgtgcccata
attaaatctttctgtgtttgtaatggtaaattatttatgttttaccttctttatttct
aag**GAACTGGCATTTGATCCATATGAATCGTATGCTCGAGATATTTTGCGACCTGGTTT
TCATGATCGTTTCCTTAGTCAGTTATCAAAGCCTGGGGCAGCACTTTATTTGCAG**gtat
agtaattttaaatgaagatgtacaatgtctgaaaagtaaacttaaaaaaaaaattaaa
tcacttttttttccagtcaataggcgaaggtttcaaagaagctgttcaatatgttttac
ccaggctgcttctggcccctgtttaccactgtctccattactttgacttttgaaggt

Figure 5A-2

EXON 8  99 bp (SEQ ID NO: 92)
ttgatccatatgaatcgtatgctcgagatattttgcgacctggttttcatgatcgtttc
cttagtcagttatcaaagcctggggcagcactttatttgcaggtatagtaattttaaa
tgaagatgtacaatgtctgaaaagtaaacttaaaaaaaaattaaatcacttttttttc
cag**TCAATAGGCGAAGGTTTCAAAGAAGCTGTTCAATATGTTTTACCCAGGCTGCTTCT
GGCCCCTGTTTACCACTGTCTCCATTACTTTGAACTTTTGAAG**gtaagaaaactcttta
ttgttatttgtaacatattcaagtgtgaatttttttttttgctacttcatttgtaaatt
attgtgtgagtaccctgcacattagtgtgtttctgttttcttttccagtcaagaagca
aatggaaatcagtctgcaaagagtagcatattttctcgtcttagt EXON 9  128 bp (SEQ ID NO: 93)
cttaacactgctaatcttggtcttttaatgtagaaaacttggttgtgtattaatagtaa
cacacaagaaaaacacttttaaaaagaatatttgatgacacatttaaaatttttattgt
gacagttgaataaatgttattttatccttaaatgagttattattatttatccaaaa
atgtactactggttcagattgtcattttggctttacag**CAGTTAGAAGAAAAAAGTGA
AGATCAAGAAGACAAGGAATGTTTAAAACAAGCAATAACAGCTTTGCTTAATGTTCAGA
GTGGTATGGAAAAAATATGTTCTAAAAGTCTTGCAAAACGAAGACTGAG**gtgaatattt
ttacttttaaaatatcctttttttccctgaatattgtggtgtaaattcagggatcccag
ttccctcctcaagtaaacaatgaagaaaatagttttagtgacaagcctggtcttttaga
ggaagtgacatcaaagccaagagaattgttattgtttgaaaaacctttcata EXON 10  656 bp (SEQ ID NO: 94)
atttctaggttgctttaattttcaaaattgtgtaattttgtaattctaatctatttggg
gaattagtgaataccttctcagtgagacttgtaaaaatctactttacactttcccttta
cttacatgagctctaggttttctgtcatctatgtactaataatgtctttttctttattc
cag**TGAATCTGCATGTCGGTTTTATAGTCAGCAAATGAAGGGGAAACAACTAGCAATCA
AGAAGATGAACGAGATTCAGAAGAATATTGATGGTTGGGAGGGAAAAGACATTGGACAG
TGTTGTAATGAATTTATAATGGAAGGAACTCTTACACGTGTAGGAGCCAAACATGAGAG
ACACATATTTCTCTTTGATGGCTTAATGATTTGCTGTAAATCAAATCATGGGCAGCCAA
GACTTCCTGGTGCTAGCAATGCAGAATATCGTCTTAAAGAAAAGTTTTTATGCGAAAG
GTACAAATTAATGATAAAGATGACACCAATGAATACAAGCATGCTTTTGAAATAATTTT
AAAAGATGAAAATAGTGTTATATTTTCTGCCAAGTCAGCTGAAGAGAAAAACAATTGGA
TGGCAGCATTGATATCTTTACAGTACCGGAGTACACTGGAAAGGATGCTTGATGTAACA
ATGCTACAGGAAGAGAAAGAGGAGCAGATGAGGCTGCCTAGTGCTGATGTTTATAGATT
TGCAGAGCCTGACTCTGAAGAGAATATTATATTTGAAGAGAACATGCAGCCCAAGGCTG
GAATTCCAATTATCAAAGCAGGAACTGTTATTAAACTTATAGAGAGGCTTACGTACCAT
ATGTACGCAG**gtaagaattatgcagttgcctgtcacttttgttttcctgcttcaaactg
atttcttcctgcatggttatattgtgcctaaaatagaaagaaactaacaaccaaag
acctcttttctttgactaaaaataccccactttatatttctttggaatgttttactttt
tctactacactta

Figure 5A-3

EXON 11  82 bp (SEQ ID NO: 95)
caccactaatttaggaggcactaagctagcagtgcattaccaagtccaaagccttctac
ttggcaaaacatttggaacttttaaacttgactatttgatctatttgaaaatgtaca
taacagttttaatcattttgaatcatagagtttaataagatattttccttttcttct
tag**ATCCCAATTTTGTTCGGACATTTCTTACAACATACAGATCCTTTTGCAAACCTCAA
GAACTACTGAGTCTTATAATAGAAAG**gtctgtccatttaaaaaatatttaaattcatta
ttttttgttaaaaagagattgagctaagatccttttcagaaatgttagatgagcttta
aaatatacttcacaagcacttttcaataaataaaatctcttagatgaacatttatttt
ataataatgttagcttttattatttcaat EXON 12  123 bp (SEQ ID NO: 96)
aataattttattagcctttaatactataggagtctcacttgtttacactgatatgcata
tcttcagtaattttttacagtattctcttgatttgctgactggtgaaaacgtttgtgg
ttttctatttgtataactcgatataattagtcttttcattaatttgttctattttatgt
tag**GTTTGAAATTCCAGAGCCTGAGCCAACAGAAGCTGATCGCATAGCTATAGAGAATG
GAGATCAACCCTTGAGTGCAGAACTGAAAAGATTTAGAAAAGAATATATACAGCCTGTG
CAACTGCG**gtaagcattaaataaatgaagtaaataagtctttatcaaactttcgtttca
atgttgaagtatataaggacctttcccaaacaaggagagggtgacaataaaattagta
aattaaatttactaattagagcagttatcagaaattatagtataagccttaacatagaa
ttttggaagtg EXON 13  104 bp (SEQ ID NO: 97)
aattagagcagttatcagaaattatagtataagccttaacatagaattttggaagtgtt
aagcacactgataagattaatttggtaagagttactgcattttcatttgtattgtactg
tgcattgtgataaacatttatgtttgattccatgtaattcaattctgtgttaatgcca
tag**AGTATTAAATGTATGTCGGCACTGGGTAGAGCACCACTTCTATGATTTTGAAAGAG
ATGCATATCTTTTGCAACGAATGGAAGAATTTATTGGAACAGTAAGAG**gtatgttttt
ttttaggtgcctagttttatatgtaataaaagtaccaacacggtgactatcaattgat
gtcattggggctcagtaatgtaagatgtttataatagtaccagcataaccatttcaaaa
agttaaaattttcatcaaatagcatttagacctgcaaatggctcaagtca EXON 14  223 bp (SEQ ID NO: 98)
agattaggattggggaccgggaaatggaaaaggagaacttgcattttcattttgatca
tttgaacttttatagcaaagatacattcaggtgtcatccgtgtgactttaaaccattt
ttaaaatataaaatattaaataaagaatatttaaatgttatttaaaatataatgtattg
cag**GTAAAGCAATGAAAAAATGGGTTGAATCCATCACTAAAATAATCCAAAGGAAAAAA
ATTGCAAGAGACAATGGACCAGGTCATAATATTACATTTCAGAGTTCACCTCCCACAGT
TGAGTGGCATATAAGCAGACCTGGGCACATAGAGACTTTTGACCTGCTCACCTTACACC
CAATAGAAATTGCTCGACAACTCACTTTACTTGAATCAGATCTATACCG**gtatgtaatt
taacattcaagttgaaaagtcatttcaaaagagttaacttttaaaatgaaatactgatt
tctgccttatagggttttcataagacttaactgaaatattacatgaagtgtctagtaat
aaggccaggcaggcagttcctgttcttttactccctggtccctctagctga

Figure 5A-4

EXON 15  120 bp (SEQ ID NO: 99)
ccataaggaaatatgcataattacactttttttgttatacctttgttttcacagaccttc
tgttggtataagaggaaagtcatatgagagtttagtttttatttgtctcctttactta
ataaaacaatgtctatattagagaaaaaagtgtcatgtagaattatgtattgatgattt
tag**AGCTGTACAGCCATCAGAATTAGTTGGAAGTGTGTGGACAAAAGAAGACAAAGAAA
TTAACTCTCCTAATCTTCTGAAAATGATTCGACATACCACCAACCTCACTCTGTGGTTT
GAGAA**gtaagtattcctagcattcttatattttatagctgtcagctatgttatgaattt
caatgcaattttttttgtttgtttttttgagacggagttttgctctgtcacataggctg
gagtgcagtggcacatcggcccactgaaacctccacctcccaggctcaagcgatcctcc
cacctcag EXON 16  163 bp (SEQ ID NO: 100)
gtatgcctgactggaggcactgccttccttctatcagtcaccctgaatgtgtcttctct
atagtagttatactatcgccacccccctactctctacattattttatttactaaattct
ttaagctataactttattggaaaaactctaaacctttagttcactttttttttattcc
cag**ATGTATTGTAGAAACTGAAAATTTAGAAGAAAGAGTAGCTGTGGTGAGTCGAATTA
TTGAGATTCTACAAGTCTTTCAAGAGTTGAACAACTTTAATGGTGTCCTTGAGGTTGTC
AGTGCTATGAATTCATCACCTGTTTACAGACTAGACCACACATTTGAG**gtaggtttcta
catgtgtttttaaaatgaactttcattccctattagaaaaattagatttttaacaatta
ttatctttaattttaaatgtctcatttgtcttttcagtagtagattaaaagactgaat
tatctaagttttgtaatgaattggttgcttttaaaatttaagcattccta EXON 17  118 bp (SEQ ID NO: 101)
actttaagtttatactgaggtctatgaagataatttatttgaagcaatatttgaagcaa
tgttacagtcataaaatcaaattgatactgttgtatttgggcgtttctgttagcctagt
attttttttgacaagacctttgattccttttgtaaacttacgcctatttttttttcctta
tag**CAAATACCAAGTCGCCAGAAGAAAATTTTAGAAGAAGCTCATGAATTGAGTGAAGA
TCACTATAAGAAATATTTGGCAAAACTCAGGTCTATTAATCCACCATGTGTGCCTTTCT
TTG**gtaagtatttcttttctgaattttttattgcatttctggataaaacaaaacactcatt
tcattaaatgactgaataattacatgtgtaatatgccagcagaaaatacttgtttgatc
aatatttagcacctgaagcccttttagaattttttctcattaagacttaaggtgaagtcta
atatac EXON 18  173 bp (SEQ ID NO: 102)
ttaagtctttcacagatactttctcttaagctgctgttttcatatcatggaaatctgag
ccttggttcttttgttttggcaactgagatggtacagtgtaatatacccacaattaatg
aaacagaaaaaaacttgcatttccttcttatccttgaaatcattccattatatcttc
tag**GAATTTATCTCACTAATATCTTGAAAACAGAAGAAGGCAACCCTGAGGTCCTAAAA
AGACATGGAAAAGAGCTTATAAACTTTAGCAAAAGGAGGAAAGTAGCAGAAATAACAGG
AGAGATCCAGCAGTACCAAAATCAGCCTTACTGTTTACGAGTAGAATCAGATATCAAA**g
taagttgaattatttaaagattcatacttctgattaagtttctaaactacttaataaaa
ggcaggtttattttataggggagaaaaagtaaaataaaccttaaaagaaataattcaaa
tttacttgtattaaatgttttcttaactttccatgaatttcaaactgaatttataattt
tg

Figure 5A-5

EXON 19  117 bp (SEQ ID NO: 103)
ttaagtttctaaactacttaataaaaggcaggtttatttttataggggagaaaaagtaaa
ataaaccttaaaagaaataattcaaatttacttgtattaaatgttttcttaactttcca
tgaatttcaaactgaatttataattttgaatattaataattttttctttgcatttattt
tag**AGGTTCTTTGAAAACTTGAATCCGATGGGAAATAGCATGGAGAAGGAATTTACAGA
TTATCTTTTCAACAAATCCCTAGAAATAGAACCACGAAACCCTAAGCCTCTCCCAAGAT
TT**gtaagcatttgtatatttgtctggtgatgtcattactaccatatgtgttatatagtt
ttccataaaggtattcagggatgaagtatacatgtgatagttaaaagtaatgaaaaagt
acttaataattatgtccaggaatatcccacttccttccaaataaatgaatgttagtatt
aattt EXON 20  265 bp (SEQ ID NO: 104)
ggctttagcaaaatagaatgttaatgctttaaatgttctacttttatttgaataattat
gtccttattagtgatttatgattttcctgtatattagctgaattttaccaggcacatat
agaaaaacttcctttctactacagtgtttaaagtattgtgtttcttttgatatgtcta
cag**CCAAAAAAATATAGCTATCCCCTAAAATCTCCTGGTGTTCGTCCATCAAACCCAAG
ACCAGGTACCATGAGGCATCCCACACCTCTGCAGCAGGAGCCAAGGAAAATTAGTTATA
GTAGGATCCCTGAAAGTGAAACAGAAAGTACAGCATCTGCACCAAATTCTCCAAGAACA
CCGTTAACACCTCCGCCTGCTTCTGGTGCTTCCAGTACCACAGATGTTTGCAGTGTATT
TGATTCCGATCATTCGAGCCCTTTTCACTCAA**gtaggtgcaaaaattctaagtgcatta
aggtatttgttagtactatacatgctagaggtaaaaaagaatctctgttattttttgt
atgtgtgaacttgtagttaagtcaaatgccatttcaaaagataatattataaaaatata
agacaaattctaaactccaccaacttgaaatttct EXON 21  45 bp (SEQ ID NO: 105)
atgaaatcaagtaaagctaaaaggaatcttaaattcccaatatgatatcatttttttct
tctcaaaagtaagtagtaatgaggttttactataaactgttacagcattctttaaaacg
acaatgacaataacatttcatcataatacaaattttgcagatgagttgaatatatca
atgaaagaaaaaaatctactttttcttgtttcctttcacag**GCAATGATACCGTCTTTA
TCCAAGTTACTCTGCCCCATGGCCCAA**gttagtatatttggtttaagactcataattct
tgctttggctttaaaaatcaaaccaagtgtaaccttcctgctaaaactcttcttgggt
ctggcagcattggtaccttgcttgcaacatcctagaagtgaggccttcacttgtgctat
ctttagatcataagtgatttgcttaaattt EXON 22  119 bp (SEQ ID NO: 106)
tgcatgcttttatggcagtttgctttaatgaaatactattcggtattggtttattgaac
agcttttggtatttctacacattacttttaattataagcaatttccagctaagacttt
caaggtaaataaatgaaataaaattcctgtggacttttcttaaaaatttaacatccca
cag**GATCTGCTTCTGTATCATCTATAAGTTTAACCAAAGGCACTGATGAAGTGCCTGTC
CCTCCTCCTGTTCCTCCACGAAGACGACCAGAATCTGCCCCAGCAGAATCTTCACCATC
TAAG**gtaaagtaagaaatcttgttgtgtagaaattggaatcattacagttcattataat
aaacggctgtctagtttagttctcactaggataagttaacatttcagagtatacaggct
taatagtttaaacaaggattacatatagatttagcatgcagtaatgttcttttcttctg
aaggtag

Figure 5A-6

EXON 23  492 bp (SEQ ID NO: 107)
aggcattgtctcaaaaaaaaaatttttttttaattaaaaagaaaacatatggcaaaac
tccctgttccacacttagcatcctgccaatagcatgtttgaaaaccccaacttaattct
tatagtcatgatacttcataaatttattaataaatgtgtatttattcttttcatttgt
tagATTATGTCTAAGCATTTGGACAGTCCCCCAGCCATTCCTCCTAGGCAACCCACATC
AAAAGCCTATTCACCACGATATTCAATATCAGACCGGACCTCTATCTCAGACCCTCCTG
AAAGCCCTCCCTTATTACCACCACGAGAACCTGTGAGGACACCTGATGTTTTCTCAAGC
TCACCACTACATCTCCAACCTCCCCCTTTGGGCAAAAAAAGTGACCATGGCAATGCCTT
CTTCCCAAACAGCCCTTCCCCCTTTACACCACCTCCTCCTCAAACACCTTCTCCTCACG
GCACAAGAAGGCATCTGCCATCACCACCATTGACACAAGAAGTGGACCTTCATTCCATT
GCTGGGCCGCCTGTTCCTCCACGACAAAGCACTTCTCAACATATCCCTAAACTCCCTCC
AAAAACTTACAAAAGGGAGCACACACACCCATCCATGCACAGAGATGGACCACCACTGT
TGGAGAATGCCCATTCTTCCTGAgttcctctgtactgggatgtatatttcctagcccc
aaatccattgctggcaatggatgcactgaatgtgccagcactgaggagttaaaatgaga
actccaaacactaacgactcttcttcaagatgcagtataagacaatgaattttaaccta
gatgtaattatacaatggaaatggta

Figure 5A-7

RAF1 (SEQ ID NO:1)

```
   1  cgcaggtcgg gaggacgagc accgagtcga gggctcgctc gtctgggccg cccgagagtc
  61  ttaatcgcgg gcgcttgggc cgccatctta gatggcggga gtaagaggaa aacgattgtg
 121  aggcgggaac ggctttctgc tgccttttt gggccccgaa aagggtcagc tggccgggct
 181  ttggggcgcg tgccctgagg cgcggagcgc gtttgctacg atgcggggc tgctcggggc
 241  tccgtcccct gggctgggga cgcgccgaat gtgaccgcct ccgctccct cacccgccgc
 301  ggggaggagg agcgggcgag aagctgccgc cgaacgacag gacgttgggg cggcctggct
 361  ccctcaggtt taagaattgt ttaagctgca tcaatggagc acatacaggg agcttggaag
 421  acgatcagca atggttttgg attcaaagat gccgtgtttg atggctccag ctgcatctct
 481  cctacaatag ttcagcagtt tggctatcag cgccgggcat cagatgatgg caaactcaca
 541  gatccttcta agacaagcaa cactatccgt gttttcttgc cgaacaagca agaacagtg
 601  gtcaatgtgc gaaatggaat gagcttgcat gactgcctta tgaaagcact caaggtgagg
 661  ggcctgcaac cagagtgctg tgcagtgttc agacttctcc acgaacacaa aggtaaaaaa
 721  gcacgcttag attggaatac tgatgctgcg tctttgattg gagaagaact tcaagtagat
 781  ttcctggatc atgttcccct cacaacacac aactttgctc ggaagacgtt cctgaagctt
 841  gccttctgtg acatctgtca gaaattcctg ctcaatggat tcgatgtca gacttgtggc
 901  tacaaatttc atgagcactg tagcaccaaa gtacctacta tgtgtgtgga ctggagtaac
 961  atcagacaac tcttattgtt tccaaattcc actattggtg atagtggagt cccagcacta
1021  ccttctttga ctatgcgtcg tatgcgagag tctgtttcca ggatgcctgt tagttctcag
1081  cacagatatt ctacacctca cgccttcacc tttaacacct ccagtccctc atctgaaggt
1141  tccctctccc agaggcagag gtcgacatcc acacctaatg tccacatggt cagcaccacc
1201  ctgcctgtgg acagcaggat gattgaggat gcaattcgaa gtcacagcga atcagcctca
1261  ccttcagccc tgtccagtag ccccaacaat ctgagcccaa caggctggtc acagccgaaa
1321  accccgtgc cagcacaaag agagcgggca ccagtatctg ggacccagga gaaaaacaaa
1381  attaggcctc gtggacagag agattcaagc tattattggg aaatagaagc cagtgaagtg
1441  atgctgtcca ctcggattgg gtcaggctct tttggaactg tttataaggg taaatggcac
1501  ggagatgttg cagtaaagat cctaaaggtt gtcgacccaa ccccagagca attccaggcc
```

Figure 5B-1

```
1561 ttcaggaatg aggtggctgt tctgcgcaaa acacggcatg tgaacattct gcttttcatg 1621 gggtacatga caaaggacaa cctggcaatt gtgacccagt ggtgcgaggg cagcagcctc 1681 tacaaacacc tgcatgtcca ggagaccaag tttcagatgt tccagctaat tgacattgcc 1741 cggcagacgg ctcagggaat ggactatttg catgcaaaga acatcatcca tagagacatg 1801 aaatccaaca atatatttct ccatgaaggc ttaacagtga aaattggaga ttttggtttg 1861 gcaacagtaa agtcacgctg gagtggttct cagcaggttg aacaacctac tggctctgtc 1921 ctctggatgg ccccagaggt gatccgaatg caggataaca acccattcag tttccagtcg 1981 gatgtctact cctatggcat cgtattgtat gaactgatga cgggggagct tccttattct 2041 cacatcaaca accgagatca gatcatcttc atggtgggcc gaggatatgc ctccccagat 2101 cttagtaagc tatataagaa ctgccccaaa gcaatgaaga ggctggtagc tgactgtgtg 2161 aagaaagtaa aggaagagag gcctcttttt ccccagatcc tgtcttccat tgagctgctc 2221 caacactctc taccgaagat caaccggagc gcttccgagc catccttgca tcgggcagcc 2281 cacactgagg atatcaatgc ttgcacgctg accacgtccc cgaggctgcc tgtcttctag 2341 ttgactttgc acctgtcttc aggctgccag gggaggagga aagccagca ggcaccactt 2401 ttctgctccc tttctccaga ggcagaacac atgttttcag agaagctgct gctaaggacc 2461 ttctagactg ctcacagggc cttaacttca tgttgccttc ttttctatcc ctttgggccc 2521 tgggagaagg aagccatttg cagtgctggt gtgtcctgct ccctccccac attccccatg 2581 ctcaaggccc agccttctgt agatgcgcaa gtggatgttg atggtagtac aaaaagcagg 2641 ggcccagccc cagctgttgg ctacatgagt atttagagga agtaaggtag caggcagtcc 2701 agccctgatg tggagacaca tgggattttg gaaatcagct tctggaggaa tgcatgtcac 2761 aggcgggact ttcttcagag agtggtgcag cgccagacat tttgcacata aggcaccaaa 2821 cagcccagga ctgccgagac tctggccgcc cgaaggagcc tgctttggta ctatggaact 2881 tttcttaggg gacacgtcct cctttcacag cttctaaggt gtccagtgca ttgggatggt 2941 tttccaggca aggcactcgg ccaatccgca tctcagccct ctcagggagc agtcttccat 3001 catgctgaat tttgtcttcc aggagctgcc cctatggggc ggggccgcag ggccagcctt
```

Figure 5B-2

```
3061 gtttctctaa caaacaaaca aacaaacagc cttgtttctc tagtcacatc atgtgtatac 3121 aaggaagcca ggaatacagg ttttcttgat gatttgggtt ttaattttgt ttttattgca 3181 cctgacaaaa tacagttatc tgatggtccc tcaattatgt tattttaata aataaatta 3241 aattt
```

Figure 5B-3

RAF1 – SEQ ID NO:2

Length: 648 AA [This is the length of the unprocessed precursor]  Molecular weight: 73052 Da [This is the MW of the unprocessed precursor]  CRC64: EF821B5349711BC3 [This is a checksum on the sequence]

```
         10         20         30         40         50         60
 MEHIQGAWKT ISNGFGFKDA VFDGSSCISP TIVQQFGYQR RASDDGKLTD PSKTSNTIRV 70         80         90        100        110        120
 FLPNKQRTVV NVRNGMSLHD CLMKALKVRG LQPECCAVFR LLHEHKGKKA RLDWNTDAAS 130        140        150        160        170        180
 LIGEELQVDF LDHVPLTTHN FARKTFLKLA FCDICQKFLL NGFRCQTCGY KFHEHCSTKV 190        200        210        220        230        240
 PTMCVDWSNI RQLLLFPNST IGDSGVPALP SLTMRRMRES VSRMPVSSQH RYSTPHAFTF 250        260        270        280        290        300
 NTSSPSSEGS LSQRQRSTST PNVHMVSTTL PVDSRMIEDA IRSHSESASP SALSSSPNNL 310        320        330        340        350        360
 SPTGWSQPKT PVPAQRERAP VSGTQEKNKI RPRGQRDSSY YWEIEASEVM LSTRIGSGSF 370        380        390        400        410        420
 GTVYKGKWHG DVAVKILKVV DPTPEQFQAF RNEVAVLRKT RHVNILLFMG YMTKDNLAIV 430        440        450        460        470        480
 TQWCEGSSLY KHLHVQETKF QMFQLIDIAR QTAQGMDYLH AKNIIHRDMK SNNIFLHEGL 490        500        510        520        530        540
 TVKIGDFGLA TVKSRWSGSQ QVEQPTGSVL WMAPEVIRMQ DNNPFSFQSD VYSYGIVLYE 550        560        570        580        590        600
 LMTGELPYSH INNRDQIIFM VGRGYASPDL SKLYKNCPKA MKRLVADCVK KVKEERPLFP 610        620        630        640
 QILSSIELLQ HSLPKINRSA SEPSLHRAAH TEDINACTLT TSPRLPVF
```

Figure 5C

RAF1 (Genomic) - SEQ ID NO:5

| Gene | RAF1 | Variant 1 |
|---|---|---|
| DNA : | 80.31 Kb | NT_022517 |
| mRNA : | 2981 bp | NM_002880 |
| CDS : | 1947 bp | NP_002871 |

| NON CODANT MRNA | CDS | initiator and stop codon | genomic and intronic adjacent sequences | allelic variation |

EXON 1    103 bp    (SEQ ID NO: 108)
atcttagatggcggggagtaagaggaaaacgattgtgaggcgggaacggctttc
tgctgcctttttgggccccgaaaagggtcagctggccgggctttggggcgcg
tgcctgaggcgcggagcgcgtttgctacgatgcgggggctgctcggggctcc
gtcccctgggctggggacgcgCCGAATGTGACCGCCTCCCGCTCCCTCACCCG
CCGCGGGGAGGAGGAGCGGGCGAGAAGCTGCCGCCGAACGACAGGACGTTGGG
GCGGCCTGGCTCCCTCAGgtaggtggcacgaccgggtcgtggatgccggggga
gccgggcggcggggctgagggatcggcttccagggcgaccgggcctgggtggc
gctgatggagcggccccgcggctgcggcagagggcttgggccaggccgttg
tcaccctggggtagcgttgggcggggccccggagtccg EXON 2    233 bp    (SEQ ID NO: 109)
Tcctcatctatgaaatatttaatggaagtgtactattaaagaaacttttcttt
gctgatgaatgcaggaggtatcattaaaaaaaccacatagtgctattttcataa
ttactctttatgtattgtgttcttgggttgaatacttttgttctagagttaca
attatttgtgtttcttaccagGTTTAAGAATTGTTTAAGCTGCATCAATGGAG
CACATACAGGGAGCTTGGAAGACGATCAGCAATGGTTTTGGATTCAAAGATGC
CGTGTTTGATGGCTCCAGCTGCATCTCTCCTACAATAGTTCAGCAGTTTGGCT
ATCAGCGCCGGGCATCAGATGATGGCAAACTCACAGATCCTTCTAAGACAAGC
AACACTATCCGTGTTTTCTTGCCGAACAAGCAAAGAACAGTGgtatgtgaaca
ttctacttaggaaatttagctatttatctgcctgtggagcacattaaggatca
tgttcaacttaaagacaggcaaaatattcattgtcatttagggtctttatttt
ttttttctaactgcagatttatttttatattgctgttccttccacacccc
ctatttttc

Figure 6A-1

EXON 3  113 bp (SEQ ID NO: 110)
tacagatgtctcacactccattcaagtactttcctattgctggacattcaggt
tgtttcgtatatgtgtgtgtgcgtgggccatcacaagcaatacagactggtgc
atttatttctgtgcccacctttccaaggggtgctgcagcctgtgttggtccta
aaggtggtcctttgtttgtag**GTCAATGTGCGAAATGGAATGAGCTTGCATGA
CTGCCTTATGAAAGCACTCAAGGTGAGGGGCCTGCAACCAGAGTGCTGTGCAG
TGTTCAGACTTCTCCACGAACACAAAGG**gtaagagctcaaaagtcaattgact
tcttcagactagtaaggatcttctagcttcaaatagctatgtttgtattaaat
tgtactagcttcctatagaatattgtatatttctacctttctttataaaga
gataattcagaaaataggtattaagaaattgaaattattgcttggaca EXON 4  103 bp (SEQ ID NO: 111)
aacttgctgtgtggccttgagcaaattaccttcttagagtcccagttttctta
ttttcagatagaataatacctacttcataggtttgttgtatgaattaaata
aattattgttgtatggattaaataaagttgtgtttatatggcatgtgataaat
ggtagctgttgttatttctattgaactttgatcttgtttaaacatttcatgtt
tttttaaatcctttctag**TAAAAAAGCACGCTTAGATTGGAATACTGATGCT
GCGTCTTTGATTGGAGAAGAACTTCAAGTAGATTTCCTGGATCATGTTCCCCT
CACAACACACAACTTT**gtaagttgcagatctcttctctttctggcatgttgag
ggctttgccaggcataacagagatttctcaggtaatatgcgtatgtatatata
tatatagttggattgtttaaagttcttatgctgttgtttacagtaaggcaat
ttagatttcattagtcagagatatactctaatttgtg EXON 5  158 bp (SEQ ID NO: 112)
Tacagtaaggcaatttagatttcattagtcagagatatactctaatttgtgat
tatgaattctgtacatgctggaagtatgattcattttgtaaaacttttttgg
aggccaagaaatgaagttgtcttttgtcatcttttatttattcagcataattt
acacctgtgttcttgttgtag**GCTCGGAAGACGTTCCTGAAGCTTGCCTTCTG
TGACATCTGTCAGAAATTCCTGCTCAATGGATTTCGATGTCAGACTTGTGGCT
ACAAATTTCATGAGCACTGTAGCACCAAAGTACCTACTATGTGTGTGGACTGG
AGTAACATCAGACAACTCTT**gtaaggcattgttcttttatccaaggaagatag
cgatgaggagtatacatacttaaagggtatttgttgtagattttgactgaca
ggtctggattctagactcatttaatgaattgtgatccagaaactactttagaa
acagtgataattctgaaactagctaggtttggtggcattca

Figure 6A-2

EXON 6  99 bp (SEQ ID NO: 113)
ctgtatgtttattggcaggtcagtattattcacattcaataatcattcaaatc
cagttatttggaatattgttccctttattctaggtaatgtaaaacagttgagg
aaaatgtgactgggaaaagttcagttttagtagctctgagtttgcaaagcaa
ggcatgctgattgtctctgtaagattactgcaagcctaaaaccagtctttcc
ctgcttttgtttag**ATTGTTTCCAAATTCCACTATTGGTGATAGTGGAGTCCC
AGCACTACCTTCTTTGACTATGCGTCGTATGCGAGAGTCTGTTTCCAGGATGC
CTGTTAG**gtaattttttacctatagcttttcttttagaaagttatttggggtg
gtggggttggaagcttgaagacaaaaaataagagtttcttcgcattccctcct
ctctacgtggaaacccttgctgcttctgtggaacttgatactggtggtacag
aaaaggtagaaatttctgtttatggacc EXON 7  154 bp (SEQ ID NO: 114)
aagcacctagacttaagataattttagatgtcacacatttgaaagaatcaaa
catttgtcaaaggttgtacaggtagagtttgcccttaagcatcttacttagt
caaatatgtacttgaaagacttcaccagtatgaaagcctaagtgccaatcatg
gaatttctttctcctcctag**TTCTCAGCACAGATATTCTACACCTCACGCCT
TCACCTTTAACACCTCCAGTCCCTCATCTGAAGGTTCCCTCTCCCAGAGGCAG
AGGTCGACATCCACACCTAATGTCCACATGGTCAGCACCACCCTGCCTGTGGA
CAGCAGGATGATTGAG**gtaatagggcaccttgggggtggtaatgtcagtcaat
taatgggtgaggttgatacttatttcagagttttgggtttcaaatctgatca
aggaatgttgcaacactttctcaggtctctggacttttacagtttattttata
tccataatatcttcagactggctgaatagtctggtta EXON 8  28 bp (SEQ ID NO: 115)
Gccactgatatttgctgaatttaatcaaggaacgttgattagagtatgtttag
gatttctatggttttagaggttttataatctatttgttcttgcacatcct
cctcctctttttccctccccagagaaaatcttttgtgtaggagttgacc
agctttccttttctgtttcagGATGCAATTCGAAGTCACAGCGAATCAGgtac
ttttccatagtcatttagccaacaataatgggcttttttctttatgcggtgt
atcttctgttggcttatccttgtgtggcttctgtttgtcttgtctattaagcc
tcaccttcagccctgtccagtagcccaacaatctgagcccaacaggctggtc
acagccgaaaaccccg

Figure 6A-3

EXON 9   128 bp (SEQ ID NO: 116)
tcttttgtgtgtaggagttgaccagctttcctttctgtttcaggatgcaatt
cgaagtcacagcgaatcaggtacttttccatagtcatttagccaacaataatg
ggcttttttctttatgcggtgtatcttctgttggcttaccttgtgtggctt
ctgtttgtcttgtctattaag**CCTCACCTTCAGCCCTGTCCAGTAGCCCCAAC
AATCTGAGCCCAACAGGCTGGTCACAGCCGAAAACCCCGTGCCAGCACAAAG
AGAGCGGGCACCAGTATCTGGGACCCAGGAGAAAAACAAAATT**gtgagtatag
acaacagtacctcctgccaattagggttcagtaagaaaaacctcgttggaaat
tagaatacttaaacttattttgggagaagattctaataaaatacattcaatga
aggagattataaatgttactgtcattttggcacacttgcatcagacagtttg
ccagtgctata EXON 10   118 bp (SEQ ID NO: 117)
agtttgccagtgctataactaaaatggtatttctcaaaagacaaaaattggaa
gtatggttaatatgtttatctttaaaagatatggaaacagatgacatgggttg
atcctttgatgccctcattatcaaagattattaccattgcatggagtataat
aatgatctctacttgtttcag**AGGCCTCGTGGACAGAGAGATTCAAGCTATTA
TTGGGAAATAGAAGCCAGTGAAGTGATGCTGTCCACTCGGATTGGGTCAGGCT
CTTTTGGAACTGTTTATAAGGGTAAATGGCACG**gtaagcttggggccctcct
ttactaactgcagggctttggtgtgaagtcaagttcagcccaggggccagg
aggaggagaggactgagtgctcctgggcttatagcagtactctcccttacata
cttgattatacctgaagattgaacttaattcttttagactaagttcttataa
a EXON 11   85 bp (SEQ ID NO: 118)
Tagcctagacaacagagtgagaccctgtctcaaaaaaaaaaaaaaaattggaa
atttgccgtatctgtgtaggtatgtgattctttggataaatgattcactgtat
cttcctcaaaactaggttatttgaaagactgagatcattcaactgattgcact
gactgccaactaattttgcag**GAGATGTTGCAGTAAAGATCCTAAAGGTTGTC
GACCCAACCCCAGAGCAATTCCAGGCCTTCAGGAATGAGGTGGCTGTTCTGCG**
gtgagtagaaagctggcggtccagtccctctggagtgctggagtggggagtac
aaggactgtagagttagtggactgtgccgcaggttgggacgggcaggcagtta
ggactcactgtggagtttctgtggttggatgctcctcccttgagagcaaaggg
atgtttcctttagtttatgtg

Figure 6A-4

EXON 12  177 bp (SEQ ID NO: 119)
gcttctctttgctcagaatgccacccgggttatcagccgtgccatgtgtttgt
ttttgggactgggggtggtgttgggactgggggtggtgtcgacagcacagaac
ccactgtccacgggaaagcacagtagacctccctgagcacttcctcctcct
ctcctctcttcccctcccctcccag**caaaacacggcatgtgaacattctgct
tttcatggggtacatgacaaaggacaacctggcaattgtgacccagtggtgcg
agggcagcagcctctacaaacacctgcatgtccaggagaccaagtttcagatg
ttccagctaattgacattgcccggcagacggctcagggaatgga**gtgagtaga
tggtctgatgcctctctgggacccaggcatcaaatttgtccctaaattggaac
caggatcaggaaaagccttctagtccattaagcgattctgtatatctttgca
caagcctctggcctgggctggaggggccaattatcaggaatgagttgttcagg
ttccagctgggt EXON 13  47 bp (SEQ ID NO: 120)
gtggcctcaccttcaggtaagcagtgatgtgaaccaggctgaacagcacaggg
tctatccctgtgtgtaacactccttggagccaggccttcagtggctttacttc
ttagctgtagtttaaaactgctttctactcatgccctcaaacttatttttaa
taatttcttttccttcacag**CTATTTGCATGCAAAGAACATCATCCATAGAG
ACATGAAATCCAACA**gtatcctttggttgttgagttcatttgactgctggtt
ctaaatttagggaaacagaagggaggctttctatcacaagtggctctcggtgc
cagggatatcttttaaggaagaggcagaggacaggaaaacagaaaagtca
gaaaattagtaggcttggcctgtccctcagcagctt EXON 14  119 bp (SEQ ID NO: 121)
Ctggaagaaggtgcatttcaaaagcactttaaagaacttcagaaaccttagga
agttcagtgcagagaggctgtgacagaggtaaggtggagagattaccgtgtta
taaagaactttgggatatttttcaaaattaacctgaccattcttttgaaacca
gagtccttaacaagcattgag**ATATATTTCTCCATGAAGGCTTAACAGTGAAA
ATTGGAGATTTTGGTTTGGCAACAGTAAAGTCACGCTGGAGTGGTTCTCAGCA
GGTTGAACAACCTACTGGCTCTGTCCTCTGGATG**gtgagaatctgggctccca
ccagcagtctctggtatagggcaaaaggaatgccttggagatttatgtgcaaa
cttaaagcgtttctgtacatttccccgaaatccacatgaccctagtgacagc
cagcctcagggcaattgtagattttcttgaggaagctgttgatcagaaccact
gt

Figure 6A-5

EXON 15  132 bp (SEQ ID NO: 122)
caaggattcctgagctgttttaaccagtgcctgagttggagtcctttggggga
aaagctatgtggggactgaagaatggactcattcataactaatgaaagggaca
gcctggcccctagatgtctgtgaggcctgtcatatggtgataaatgcactttt
gtcatatggtgatacatgtag**GCCCCAGAGGTGATCCGAATGCAGGATAACAA
CCCATTCAGTTTCCAGTCGGATGTCTACTCCTATGGCATCGTATTGTATGAAC
TGATGACGGGGGAGCTTCCTTATTCTCACATCAACAACCGAGATCAG**gtaagt
ctgtgctggtgcgaaaggacccaactcgtgggagccctgggcctccgccagc
ctaagcagctagagggttaggacttgttattatctgttgttcattcacccccc
attagctcagctgttttctttcccttagatcatcttcatggtgggccgaggat
atgcctcccagatc EXON 16  135 bp (SEQ ID NO: 123)
Ggggagcttccttattctcacatcaacaaccgagatcaggtaagtctgtgct
ggtgcgaaaggacccaactcgtgggagccctgggcctccgccagcctaagca
gctagagggttaggacttgttattatctgttgttcattcacccccattagct
cagctgttttctttccttag**ATCATCTTCATGGTGGGCCGAGGATATGCCTC
CCCAGATCTTAGTAAGCTATATAAGAACTGCCCCAAAGCAATGAAGAGGCTGG
TAGCTGACTGTGTGAAGAAAGTAAAGGAAGAGAGGCCTCTTTTTCCCCAG**gta
aggctcagggctgctagaatgtgattaaagcatgggttggttcgtaaagatgg
caatataaggtgggagtgttttgttttgttttatagggagggacccaggtcc
tctacaagatggtgggggcagggtacatcctgtgtctttgagacacagctaa
tgagagcattcttgggct

Figure 6A-6

EXON 17 1049 bp (SEQ ID NO: 124)
agggctgctagaatgtgattaaagcatgggttggttcgtaaagatggcaatat
aaggtgggagtgttttgttttgttttatagggaggggacccaggtcctctaca
agatggtgggggcagggtacatcctgtgtctttgagacacagctaatgagag
cattcttgggctttgtttcag**ATCCTGTCTTCCATTGAGCTGCTCCAACACTC
TCTACCGAAGATCAACCGGAGCGCTTCCGAGCCATCCTTGCATCGGGCAGCCC
ACACTGAGGATATCAATGCTTGCACGCTGACCACGTCCCCGAGGCTGCCTGTC
TTCTAG**TTGACTTTGCACCTGTCTTCAGGCTGCCAGGGGAGGAGGAGAAGCCA
GCAGGCACCACTTTTCTGCTCCCTTTCTCCAGAGGCAGAACACATGTTTTCAG
AGAAGCTGCTGCTAAGGACCTTCTAGACTGCTCACAGGGCCTTAACTTCATGT
TGCCTTCTTTTCTATCCCTTTGGGCCCTGGGAGAAGGAAGCCATTTGCAGTGC
TGGTGTGTCCTGCTCCCTCCCCACATTCCCCATGCTCAAGGCCCAGCCTTCTG
TAGATGCGCAAGTGGATGTTGATGGTAGTACAAAAAGCAGGGGCCCAGCCCCA
GCTGTTGGCTACATGAGTATTTAGAGGAAGTAAGGTAGCAGGCAGTCCAGCCC
TGATGTGGAGACACATGGGATTTTGGAAATCAGCTTCTGGAGGAATGCATGTC
ACAGGCGGGACTTTCTTCAGAGAGTGGTGCAGCGCCAGACATTTTGCACATAA
GGCACCAAACAGCCCAGGACTGCCGAGACTCTGGCCGCCCGAAGGAGCCTGCT
TTGGTACTATGGAACTTTTCTTAGGGGACACGTCCTCCTTTCACAGCTTCTAA
GGTGTCCAGTGCATTGGGATGGTTTTCCAGGCAAGGCACTCGGCCAATCCGCA
TCTCAGCCCTCTCAGGGAGCAGTCTTCCATCATGCTGAATTTTGTCTTCCAGG
AGCTGCCCCTATGGGGCGGGGCCGCAGGGCCAGCCTTGTTTCTCTAACAAACA
AACAAACAAACAGCCTTGTTTCTCTAGTCACATCATGTGTATACAAGGAAGCC
AGGAATACAGGTTTTCTTGATGATTTGGGTTTTAATTTGTTTTTATTGCACC
TGACAAAATACAGTTATCTGATGGTCCCTCAATTATGTTATTTTAATAAAATA
AATTAAATTTaggtgtaatggctggctgttacctccttttaaagtaattctga
gctcacaacttgaatgcccatttgttcacctcttcaggagcagaattcaag
aacaggaaatgtgcccagagcctaggctgggaatgaatttgtaatttaaccct
tgtactctttgtaaacctctactgaagagtt

Figure 6A-7

SOS1 (SEQ ID NO:3)

```
1    atgcaggcgc agcagctgcc ctacgagttt ttcagcgaag agaacgcgcc caagtggcgg
61   ggactactgg tgcctgcgct gaaaaaggtc caggggcaag ttcatcctac tctcgagtct
121  aatgatgatg ctcttcagta tgttgaagaa ttaattttgc aattattaaa tatgctatgc
181  caagctcagc ccgaagtgc ttcagatgta gaggaacgtg ttcaaaaaag tttccctcat
241  ccaattgata atgggcaat agctgatgcc caatcagcta tgaaaagag gaagcgaaga
301  aaccctttat ctctcccagt agaaaaaatt catcctttat taaggaggt cctaggttat
361  aaaattgacc accaggtttc tgtttacata gtagcagtct tagaatacat ttctgcagac
421  attttaaagc tggttgggaa ttatgtaaga aatatacggc attatgaaat tacaaaacaa
481  gatattaaag tggcaatgtg tgctgacaag gtattgatgg atatgtttca tcaagatgta
541  gaagatatta atatattatc tttaactgac gaagagcctt ccacctcagg agaacaaact
601  tactatgatt tggtaaaagc atttatggca gaaattcgac aatatataag ggaactaaat
661  ctaattataa agtttttag agagccctt gtctccaatt caaaattgtt ttcagctaat
721  gatgtagaaa atatatttag tcgcatagta gatatacatg aacttagtgt aaagttactg
781  ggccatatag aagatacagt agaaatgaca gatgaaggca gtccccatcc actagtagga
841  agctgctttg aagacttagc agaggaactg gcatttgatc catatgaatc gtatgctcga
901  gatattttgc gacctggttt tcatgatcgt ttccttagtc agttatcaaa gcctggggca
961  gcactttatt tgcagtcaat aggcgaaggt ttcaaagaag ctgttcaata tgttttaccc
1021 aggctgcttc tggcccctgt ttaccactgt ctccattact ttgaactttt gaagcagtta
1081 gaagaaaaaa gtgaagatca agaagacaag gaatgtttaa acaagcaat aacagctttg
1141 cttaatgttc agagtggtat ggaaaaaata tgttctaaaa gtcttgcaaa acgaagactg
1201 agtgaatctg catgtcggtt ttatagtcag caaatgaagg ggaaacaact agcaatcaag
1261 aagatgaacg agattcagaa gaatattgat ggttgggagg gaaaagacat ggacagtgt
1321 tgtaatgaat ttataatgga aggaactctt acacgtgtag agccaaaaca tgagagacac
1381 atatttctct tgatggctt aatgatttgc tgtaaatcaa atcatgggca gccaagactt
```

Figure 6B-1

```
1441 cctggtgcta gcaatgcaga atatcgtctt aaagaaaagt tttttatgcg aaaggtacaa 1501 attaatgata aagatgacac caatgaatac aagcatgctt ttgaaataat tttaaaagat 1561 gaaaatagtg ttatattttc tgccaagtca gctgaagaga aaaacaattg gatggcagca 1621 ttgatatctt tacagtaccg gagtacactg gaaaggatgc ttgatgtaac aatgctacag 1681 gaagagaaag aggagcagat gaggctgcct agtgctgatg tttatagatt tgcagagcct 1741 gactctgaag agaatattat atttgaagag aacatgcagc ccaaggctgg aattccaatt 1801 atcaaagcag gaactgttat taaacttata gagaggctta cgtaccatat gtacgcagat 1861 cccaattttg ttcggacatt tcttacaaca tacagatcct tttgcaaacc tcaagaacta 1921 ctgagtctta aatagaaag gtttgaaatt ccagagcctg agccaacaga agctgatcgc 1981 atagctatag agaatggaga tcaaccttg agtgcagaac tgaaaagatt tagaaaagaa 2041 tatatacagc ctgtgcaact gcgagtatta aatgtatgtc ggcactgggt agagcaccac 2101 ttctatgatt ttgaaagaga tgcatatctt ttgcaacgaa tggaagaatt tattggaaca 2161 gtaagaggta aagcaatgaa aaatggggtt gaatccatca ctaaaataat ccaaaggaaa 2221 aaaattgcaa gagacaatgg accaggtcat aatattacat ttcagagttc acctcccaca 2281 gttgagtggc atataagcag acctgggcac atagagactt tgacctgct caccttacac 2341 ccaatagaaa ttgctcgaca actcacttta cttgaatcag atctataccg agctgtacag 2401 ccatcagaat tagttggaag tgtgtggaca aaagaagaca aagaaattaa ctctcctaat 2461 cttctgaaaa tgattcgaca taccaccaac ctcactctgt ggtttgagaa atgtattgta 2521 gaaactgaaa atttagaaga aagagtagct gtggtgagtc gaattattga gattctacaa 2581 gtctttcaag agttgaacaa ctttaatggt gtccttgagg ttgtcagtgc tatgaattca 2641 tcacctgttt acagactaga ccacacattt gagcaaatac caagtcgcca gaagaaaatt 2701 ttagaagaag ctcatgaatt gagtgaagat cactataaga aatatttggc aaaactcagg 2761 tctattaatc caccatgtgt gcctttcttt ggaatttatc tcactaatat cttgaaaaca 2821 gaagaaggca accctgaggt cctaaaaaga catggaaaag agcttataaa ctttagcaaa
```

Figure 6B-2

```
2881 aggaggaaag tagcagaaat aacaggagag atccagcagt accaaaatca gccttactgt
2941 ttacgagtag aatcagatat caaaaggttc tttgaaaact tgaatccgat gggaaatagc
3001 atggagaagg aatttacaga ttatctttc aacaaatccc tagaaataga accacgaaac
3061 cctaagcctc tcccaagatt tccaaaaaaa tatagctatc cctaaaatc tcctggtgtt
3121 cgtccatcaa acccaagacc aggtaccatg aggcatccca cacctctgca gcaggagcca
3181 aggaaaatta gttatagtag gatccctgaa agtgaaacag aaagtacagc atctgcacca
3241 aattctccaa gaacaccgtt aacacctccg cctgcttctg gtgcttccag taccacagat
3301 gtttgcagtg tatttgattc cgatcattcg agccctttc actcaagcaa tgataccgtc
3361 tttatccaag ttactctgcc ccatggccca agatctgctt ctgtatcatc tataagttta
3421 accaaaggca ctgatgaagt gcctgtccct cctcctgttc ctccacgaag acgaccagaa
3481 tctgccccag cagaatcttc accatctaag attatgtcta agcatttgga cagtccccca
3541 gccattcctc ctaggcaacc cacatcaaaa gcctattcac cacgatattc aatatcagac
3601 cggacctcta tctcagaccc tcctgaaagc cctcccttat taccaccacg agaacctgtg
3661 aggacacctg atgttttctc aagctcacca ctacatctcc aacctccccc tttgggcaaa
3721 aaaagtgacc atggcaatgc cttcttccca aacagcccct ccccctttac accacctcct
3781 cctcaaacac cttctcctca cggcacaaga aggcatctgc catcaccacc attgacacaa
3841 gaagtggacc ttcattccat tgctgggccg cctgttcctc cacgacaaag cacttctcaa
3901 catatcccta aactccctcc aaaaacttac aaaagggagc acacacaccc atccatgcac
3961 agagatggac caccactgtt ggagaatgcc cattcttcct ga
```

Figure 6B-3

SOS1 – SEQ ID NO:4

Length: 1333 AA [This is the length of the unprocessed precursor] Molecular weight: 152464 Da [This is the MW of the unprocessed precursor] CRC64: C6B99CCA11A8DE45 [This is a checksum on the sequence]

```
           10         20         30         40         50         60
    MQAQQLPYEF FSEENAPKWR GLLVPALKKV QGQVHPTLES NDDALQYVEE LILQLLNMLC 70         80         90        100        110        120
    QAQPRSASDV EERVQKSFPH PIDKWAIADA QSAIEKRKRR NPLSLPVEKI HPLLKEVLGY 130        140        150        160        170        180
    KIDHQVSVYI VAVLEYISAD ILKLVGNYVR NIRHYEITKQ DIKVAMCADK VLMDMFHQDV 190        200        210        220        230        240
    EDINILSLID EEPSTSGEQT YYDLVKAFMA EIRQYIRELN LIIKVFREPF VSNSKLFSAN 250        260        270        280        290        300
    DVENIFSRIV DIHELSVKLL GHIEDIVEMT DEGSPHPLVG SCFEDLAEEL AFDPYESYAR 310        320        330        340        350        360
    DILRPGFHDR FLSQLSKPGA ALYLQSIGEG FKEAVQYVLP RLLLAPVYHC LHYFELLKQL 370        380        390        400        410        420
    EEKSEDQEDK ECLKQAIIAL LNVQSGMEKI CSKSLAKRRL SESACRFYSQ QMKGKQLAIK 430        440        450        460        470        480
    KMNEIQKNID GWEGKDIGQC CNEFIMEGTL TRVGAKHERH IFLFDGLMIC CKSNHGQPRL 490        500        510        520        530        540
    PGASNAEYRL KEKFFMRKVQ INDKDDTNEY KHAFEIILKD ENSVIFSAKS AEEKNNWMAA 550        560        570        580        590        600
    LISLQYRSIL ERMLDVTMLQ EEKEEQMRLP SADVYRFAEP DSEENIIFEE NMQPKAGIPI 610        620        630        640        650        660
    IKAGTVIKLI ERLTYHMYAD PNFVRIFLTT YRSFCKPQEL LSLIIERFEI PEPEPTEADR 670        680        690        700        710        720
    IAIENGDQPL SAELKRFRKE YIQPVQLRVL NVCRHWVEHH FYDFERDAYL LQRMEEFIGT
```

Figure 6C-1

```
          730        740        750        760        770        780
VRGKAMKKWV ESITKIIQRK KIARDNGPGH NITFQSSPPT VEWHISRPGH IETFDLLTLH 790        800        810        820        830        840
PIEIARQLTL LESDLYRAVQ PSELVGSVWT KEDKEINSPN LLKMIRHTTN LTLWFEKCIV 850        860        870        880        890        900
ETENLEERVA VVSRIIEILQ VFQELNNFNG VLEVVSAMNS SPVYRLDHTF EQIPSRQKKI 910        920        930        940        950        960
LEEAHELSED HYKKYLAKLR SINPPCVPFF GIYLTNILKT EEGNPEVLKR HGKELINFSK 970        980        990       1000       1010       1020
RRKVAEITGE IQQYQNQPYC LRVESDIKRF FENLNPMGNS MEKEFTDYLF NKSLEIEPRN 1030       1040       1050       1060       1070       1080
PKPLPRFPKK YSYPLKSPGV RPSNPRPGTM RHPTPLQQEP RKISYSRIPE SETESTASAP 1090       1100       1110       1120       1130       1140
NSPRTPLTPP PASGASSTTD VCSVFDSDHS SPFHSSNDTV FIQVTLPHGP RSASVSSISL 1150       1160       1170       1180       1190       1200
TKGTDEVPVP PPVPPRRRPE SAPAESSPSK IMSKHLDSPP AIPPRQPTSK AYSPRYSISD 1210       1220       1230       1240       1250       1260
RTSISDPPES PPLLPPREPV RTPDVFSSSP LHLQPPPLGK KSDHGNAFFP NSPSPFTPPP 1270       1280       1290       1300       1310       1320
PQTPSPHGTR RHLPSPPLTQ EVDLHSIAGP PVPPRQSTSQ HIPKLPPKTY KREHTHPSMH

1330
RDGPPLLENA HSS
```

COMPOSITIONS AND METHODS FOR DETECTING NOONAN SYNDROME

STATEMENT REGARDING FEDERALLY SPONSORED RESEARCH

This invention was made with government support under Grant Nos. HL71207, HD001294 and HL074728, HL066681 awarded by the National Institutes of Health, and Contract Nos. DE-AC02-05CH11231, DE-AC52-07NA27344, and DE-AC02-06NA25396 awarded by the Department of Energy. The government has certain rights in the invention.

This application is the U.S. National Stage of International Patent Application Serial No. PCT/US07/85005, filed Nov. 16, 2007, which claims priority from U.S. Provisional Application Ser. No. 60/866,204, filed Nov. 16, 2006, both of which are hereby incorporated by reference in their entireties.

TECHNICAL FIELD

The present disclosure relates to diagnostic and therapeutic applications for Noonan Syndrome and, more specifically, to diagnostic and therapeutic applications based on certain mutations in RAS-specific guanine nucleotide exchange factor gene SOS1 or its expression product thereof, or certain mutations in serine/threonine protein kinase gene RAF1 or its expression product thereof.

BACKGROUND

Noonan syndrome (NS) is a developmental disorder characterized by short stature, facial dysmorphia, congenital heart defects (e.g., most commonly pulmonic stenosis and hypertrophic cardiomyopathy) and skeletal anomalies (Noonan, *Am. J. Dis. Child.* 116:373-80, 1968; Allanson, *J. Med. Genet.* 24:9-13, 1987). Other frequently associated disorders include a webbed neck, chest deformities, cryptorchidism, mental retardation, and bleeding diatheses. NS is a relatively common syndrome with an estimated incidence of 1:1000 to 1:2500 live births.

Increased RAS-mitogen-activated protein kinase (MAPK) signaling due to PTPN11 and KRAS mutations cause 50% of NS (Carta et al., *Am J Hum Genet* 79:129-35, 2006; Fragale et al., *Hum. Mutat.* 23, 267-77, 2004; Schubbert et al., *Nat Genet* 38:331-6, 2006; Tartaglia et al., *Am. J. Hum. Genet.* 70:1555-63, 2002; Tartaglia et al. *Nat. Genet.* 29:465-8, 2001). PTPN11, the first NS-associated gene identified (Tartaglia et al., 2001; see also U.S. Pat. Pub. No. 2003/0125289), encodes the non-membranous protein tyrosine phosphatase, SHP-2, that primarily serves positive regulatory roles in signal transduction, particularly via the receptor tyrosine kinase (RTK)-mediated RAS-MAPK pathway. Most mutations perturb the switch between the basally inactive and phosphotyrosine-bound active conformations of SHP-2, shifting the equilibrium towards the latter Fragale et al., 2004; Tartaglia et al., 2001; Keilhack et al., *J. Biol. Chem.* 280:30984-93, 2005; Tartaglia et al., *Am. J. Hum. Genet.* 78:279-90, 2006).

The clinical diagnosis of NS depends on recognition of the symptoms by a knowledgeable doctor. Nevertheless, substantial phenotypic variations, including mild or subtle cases, make the diagnosis difficult. Furthermore, the facial characteristics become less apparent with progressing age, so NS will sometimes remain undiagnosed. A genetic test for diagnosing Noonan syndrome involves detecting mutations in PTPN11 and KRAS, but PTPN11 and KRAS mutations account for only 50% of patients suspected of having NS. Therefore, there remains a need to identify other specific gene(s) involved in Noonan syndrome—such identification would aid in the diagnosis (in particular, early diagnosis) and treatment of a broader population of patients afflicted with NS.

SUMMARY

The present disclosure provides methods of diagnosing and treating Noonan syndrome (NS). By identifying mutations in serine/threonine protein kinase gene RAF1 in subjects with Noonan syndrome or in RAS-specific guanine nucleotide exchange factor gene SOS1, the inventors provide tools for developing genetically-based diagnostic and therapeutic applications.

In one aspect, this disclosure provides a method for diagnosing Noonan syndrome in a human subject suspected of having NS, which method comprises detecting a mutation in a RAF1 nucleic acid molecule in the subject. In certain embodiments, a mutation results in increased RAF1 activity or expression as compared to a control. The mutation can be a missense mutation, a deletion, an insertion, or a combination thereof. In other embodiments, a mutation is in a coding region of a RAF1 nucleic acid molecule, and results in a RAF1 variant polypeptide, such as a polypeptide having an amino acid substitution. In certain embodiments, a mutation in a RAF1 polypeptide is in a conserved region 2 (CR2) domain, such as amino acid substitutions at the following residues of SEQ ID NO:2: an R to S substitution at position 256; an S to L substitution at position 257; an S to F substitution at position 259; a T to R substitution at position 260; a P to S substitution at position 261; a P to R substitution at position 261; and a P to L substitution at position 261. In further embodiments, a mutation in a RAF1 polypeptide is in a CR3 domain, such as amino acid substitutions at the following residues of SEQ ID NO:2: a D to N substitution at position 486; a D to G substitution at position 486; a T to I substitution at position 491; and a T to R substitution at position 491. In still further embodiments, a mutation in a RAF1 polypeptide is in a carboxy-terminal domain, such as amino acid substitutions at the following residues of SEQ ID NO:2: an S to T substitution at position 612; and an L to V substitution at position 613.

In related embodiments, RAF1 nucleic acid molecule mutations may include nucleotide substitutions of SEQ ID NO:1 in RAF1 exon 7, exon 14, or exon 16. In certain embodiments, RAF1 nucleic acid molecule mutations in the region encoding a CR2 domain may include nucleotide substitutions at the following nucleotides of SEQ ID NO:1: a G to C substitution at position 1161; a G to T substitution at position 1161; a C to T substitution at position 1163; a C to T substitution at position 1169; a C to G substitution at position 1172; a C to T substitution at position 1174; and a C to T substitution at position 1175. In further embodiments, a mutation in a RAF1 nucleic acid molecule in the region encoding a CR3 domain may include nucleotide substitutions at the following nucleotides of SEQ ID NO:1: a G to A substitution at position 1849; an A to G substitution at position 1850; a C to T substitution at position 1865; and a C to G substitution at position 1865. In still further embodiments, a mutation in a RAF1 nucleic acid molecule in the region encoding the carboxy-terminal may include nucleotide substitutions at the following nucleotides of SEQ ID NO:1: a T to A substitution at position 2227; and a C to G substitution at position 2230.

In another aspect, this disclosure provides a method for diagnosing Noonan syndrome in a human subject suspected of having NS, which method comprises detecting a mutation in a Son of Sevenless homolog 1 (SOS1) nucleic acid molecule in the subject. In certain embodiments, a mutation results in increased SOS1 activity or expression as compared to a control. The mutation can be a missense mutation, a deletion, an insertion, or a combination thereof. In other embodiments, a mutation is in a coding region of an SOS1 nucleic acid molecule, and results in a SOS1 variant polypeptide. In one embodiment, a mutation in an SOS1 polypeptide is in an amino acid involved in autoinhibition activity wherein the autoinhibition activity is reduced as compared to wild-type SOS1 (e.g., SOS1 polypeptide of SEQ ID NO:4). In certain embodiments, a mutation in an SOS1 polypeptide is in a Pleckstrin Homology (PH) domain, such as amino acid substitutions at the following residues of SEQ ID NO:4: a W to R substitution at position 432; an E to K substitution at position 433; and a C to Y substitution at position 441. In further embodiments, a mutation in an SOS1 polypeptide is in a linker between a PH domain and a RAS exchanger motif (Rem) domain, such as amino acid substitutions at the following residues of SEQ ID NO:4: an S to R substitution at position 548; an L to P substitution at position 550; an R to G substitution at position 552; an R to K substitution at position 552; and an R to S substitution at position 552. In still further embodiments, a mutation in an SOS1 polypeptide is at an amino acid that forms part of an interacting region between a Dbl homology (DH) and a Rem domain, such as amino acid substitutions at the following residues of SEQ ID NO:4: a M to R substitution at position 269; a W to L substitution at position 729; and an I to F substitution at position 733. In another embodiment, a mutation in an SOS1 polypeptide is in a histone folds domain, such as an E to K substitution at position 108 of SEQ ID NO:4. In still another embodiment, a mutation in an SOS1 polypeptide is in a Rem domain, such as a Y to H substitution at position 702 of SEQ ID NO:4. In yet another embodiment, a mutation in an SOS1 polypeptide is in a Cdc25 homology domain, such as an E to K substitution at position 846 of SEQ ID NO:4; or a Q to R substitution at position 977 of SEQ ID NO:4. In a further embodiment, a mutation in an SOS1 polypeptide is in the carboxy-terminal, such as an H to R substitution at position 1320 of SEQ ID NO:4. In one embodiment, an SOS1 polypeptide mutation at P655 of SEQ ID NO:4 is a polymorphism and does not correlate with NS. In yet a further embodiment, a mutant SOS1 polypeptide further comprises a deletion at position 432-433 wherein the amino acids W432 and E433 are deleted. Such an embodiment is exemplified by an R to S substitution at position 552 in combination with a W432-E433 deletion.

In related embodiments, SOS1 nucleic acid molecule mutations may include nucleotide substitutions of SEQ ID NO:1 in SOS1 exon 4, exon 7, exon 11, exon 14, exon 15, or exon 17. In certain embodiments, SOS1 nucleic acid molecule mutations in the region encoding a PH domain may include nucleotide substitutions at the following nucleotides of SEQ ID NO:3: a T to C substitution at position 1294; a G to A substitution at position 1297; and a G to A substitution at position 1322. In further embodiments, a mutation in a SOS1 nucleic acid molecule in the region encoding a PH-Rem domain linker may include nucleotide substitutions at the following nucleotides of SEQ ID NO:3: an A to C substitution at position 1642; a T to C substitution at position 1649; an A to G substitution at position 1654; a G to A substitution at position 1655; and a G to C substitution at position 1656. In still further embodiments, a mutation in a SOS1 nucleic acid molecule that encodes an amino acid that forms part of an interacting region between a DH and a Rem domain may include nucleotide substitutions at the following nucleotides of SEQ ID NO:3: a T to G substitution at position 806; a G to T substitution at position 2186; and an A to T substitution at position 2197. In another embodiment, a mutation in an SOS1 nucleic acid molecule is in a region encoding a histone folds domain, such as a G to A substitution at position 322 of SEQ ID NO:3. In still another embodiment, a mutation in an SOS1 nucleic acid molecule is in a region encoding a Rem domain, such as a T to C substitution at position 2104 of SEQ ID NO:3. In yet another embodiment, a mutation in a SOS1 nucleic acid molecule is in a region encoding a Cdc25 homology domain, such as a G to A substitution at position 2536 of SEQ ID NO:3; an A to T substitution at position 2930 of SEQ ID NO:3; or an A to G substitution at position 2930 of SEQ ID NO:3. In a further embodiment, a mutation in an SOS1 nucleic acid molecule is in a region encoding the carboxy-terminus, such as an A to G substitution at position 3959 of SEQ ID NO:3. In particular embodiments, an SOS1 nucleic acid molecule mutation at C1964 of SEQ ID NO:3 or A2930 of SEQ ID NO:3, does not correlate with NS.

In a further aspect, this disclosure provides a method for diagnosing Noonan syndrome in a human subject suspected of having NS, which method comprises assessing the level of activity of a RAF1 or SOS1 signal transduction pathway in a human subject suspected of having NS and comparing it to the level of activity in a control subject, wherein increased activity of the pathway in the subject suspected of having NS compared to the control subject is indicative of Noonan syndrome. The level of activity of the pathway can, for example, be assessed by assessing an increase in the level of activity or expression of a RAF1 or SOS1 polypeptide. Alternatively, the level of activity of the pathway can be assessed by measuring an increase in the level of activity or expression of an ERK protein, such as, e.g., ERK2. The level of activity or expression of the ERK protein may be assessed by assessing kinase activity, as described herein.

In still a further aspect, this disclosure provides a kit for diagnosing Noonan syndrome in a human subject suspected of having NS, comprising an oligonucleotide that specifically hybridizes to or adjacent to a site of mutation of a RAF1 nucleic acid sequence that results in increased activity of a RAF1 or polypeptide encoded by such a mutated nucleic acid sequence, and instructions for use. The site of RAF1 mutations may, for example, be found at nucleotide 1161, 1163, 1169, 1172, 1174, 1175, 1849, 1850, 1865, 2227, or 2230 of SEQ ID NO:1. In a further embodiment, the kit comprises at least one probe comprising the site of mutation. In another embodiment, the kit comprises a first oligonucleotide primer comprising at least 15 consecutive nucleotides of SEQ ID NO:5, and a second oligonucleotide primer comprising at least 15 consecutive nucleotides of a sequence complementary to SEQ ID NO:5. In still another embodiment, the kit comprises a first oligonucleotide primer comprising at least about 10 and up to about 30 consecutive nucleotides of SEQ ID NO:5, and a second oligonucleotide primer comprising at least about 10 and up to about 30 consecutive nucleotides of a sequence complementary to SEQ ID NO:5.

In yet a further aspect, this disclosure provides a kit for diagnosing Noonan syndrome in a human subject suspected of having NS, comprising an oligonucleotide that specifically hybridizes to or adjacent to a site of mutation of an SOS1 nucleic acid sequence that results in increased activity of an SOS1 polypeptide encoded by such a mutated nucleic acid sequence, and instructions for use. The site of SOS1 mutations may, for example, be found at nucleotide 322, 806, 1294, 1297, 1322, 1642, 1649, 1654, 1655, 1656, 2104, 2186, 2197, 2536, 2930, and 3959 of SEQ ID NO:3. In a further embodiment, the kit comprises at least one probe comprising the site of mutation. In another embodiment, the kit comprises a first oligonucleotide primer comprising at least 15 consecutive nucleotides of SEQ ID NO:6, and a second oligonucleotide primer comprising at least 15 consecutive nucleotides of a sequence complementary to SEQ ID NO:6. In still another embodiment, the kit comprises a first oligonucleotide primer comprising at least about 10 and up to about 30 consecutive nucleotides of SEQ ID NO:6, and a second oligonucleotide primer comprising at least about 10 and up to about 30 consecutive nucleotides of a sequence complementary to SEQ ID NO:6.

In yet a further aspect, this disclosure further provides a kit for diagnosing Noonan syndrome in a human subject suspected of having NS, comprising an antibody that specifically recognizes a mutation in a RAF1 or SOS1 polypeptide, and instructions for use. In certain embodiments, the mutation results in RAF1 or SOS1 polypeptide variant having an increased activity as compared to a wild-type RAF1 having an amino acid sequence of SEQ ID NO:2 or to a wild-type SOS1 having an amino acid sequence of SEQ ID NO:4, respectively. In certain embodiments, an antibody specifically binds to a RAF1 or SOS1 polypeptide variant, wherein the RAF1 or SOS1 polypeptide variant is as described herein.

In another aspect, this disclosure also provides for a method for diagnosing Noonan syndrome in a subject, which method comprises assessing the level of expression or activity of a RAF1 or SOS1 polypeptide variant in a human subject suspected of having NS and comparing to the level of expression or activity in a control subject, wherein an increased expression or basal activity of the RAF1 polypeptide in the subject suspected of having NS compared to the control subject is indicative of Noonan syndrome. The level of expression may, for example, be assessed by determining the amount of mRNA that encodes a RAF1 or SOS1 polypeptide in a biological sample or by determining the concentration of RAF1 or SOS1 polypeptide in a biological sample. The level of activity may, for example, be assessed by determining the level of RAF1 or SOS1 activity in the subject suspected of having NS.

This disclosure further provides a method for treating Noonan syndrome in a patient, which method comprises administering to the patient in need of such treatment an effective amount of an agent that modulates the expression or activity of a RAF1 or SOS1 variant polypeptide. In certain embodiments, the therapeutic agent is provided with a pharmaceutically acceptable carrier or diluent. In some embodiments, although not necessarily, the therapeutic agent is a wild-type RAF1 or SOS1 polypeptide comprising the amino acid sequence of SEQ ID NO:2 or SEQ ID NO:4, respectively. In one embodiment, the agent is a RAF1 antisense nucleic acid, preferably an antisense nucleic acid hybridizing to a segment of SEQ ID NO:1 comprising at least one nucleotide substitution as described herein. In one embodiment, the agent is a SOS1 antisense nucleic acid, preferably an antisense nucleic acid hybridizing to a segment of SEQ ID NO:3 comprising at least one nucleotide substitution as described herein.

In a specific embodiment, an agent inhibits RAF1 or SOS1 activity by blocking a RAF1 or SOS1 polypeptide variant activity, such as blocking upregulated RAS-MAPK signaling. For example, the agent can be an anti-RAF1 or an anti-SOS1 inhibitory antibody. Such an antibody could specifically recognize a RAF1 or SOS1 amino acid sequence comprising a mutation as described herein.

In a further aspect, this disclosure provides for an isolated RAF1 or SOS1 polypeptide variant comprising a mutation resulting in increased level of RAF1 or SOS1 activity. In particular embodiments, the isolated RAF1 or SOS1 polypeptide variants comprise an amino acid substitution as described herein.

This disclosure also provides an isolated nucleic acid encoding any of the RAF1 or SOS1 polypeptide variants described herein, as well as isolated oligonucleotides that specifically hybridize to such nucleic acids. This disclosure further provides for an isolated cell comprising a vector, which vector comprises a nucleic acid encoding any RAF1 or SOS1 polypeptide variant described herein, the nucleic acid operatively associated with an expression control sequence. In certain embodiments, the cell can be, for example, a prokaryotic cell or a eukaryotic cell.

Figure 1:
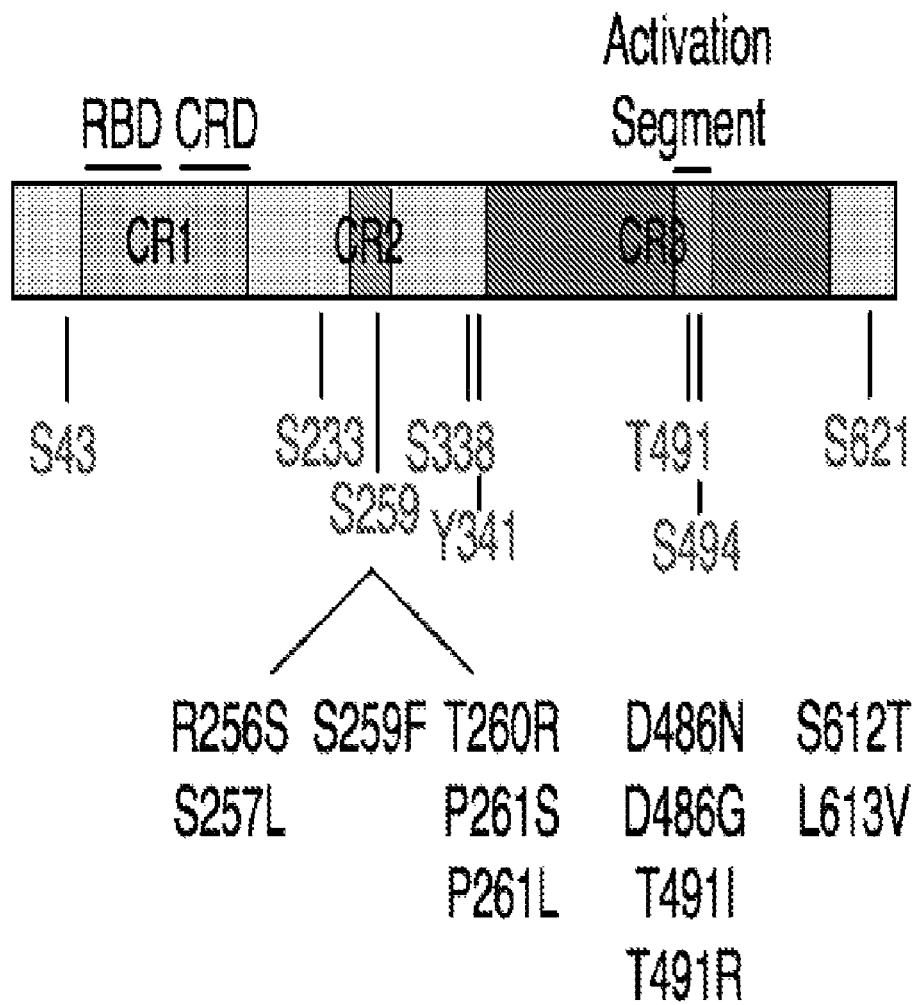
FIG. 1 is a schematic drawing showing the functional domains of the RAF1 polypeptide, including three Conserved Region domains (CR1, CR2, CR3) and a carboxy-terminal domain, are shown below. Above the schematic, the location of a Ras binding domain (RBD) and a cysteine-rich domain (CRD) within CR1 is shown, and the location of an Activation Segment within CR3 is shown. The first tier below the schematic shows the serines (S), threonine (T), and tyrosine (Y) that can be phosphorylated. The second tier below the schematic indicates the location of residues altered in Noonan syndrome.

Results for the mutants were compared to WT using one-tailed T-tests. Significant differences of p<0.01 are indicated with **.

FIGS. 5A to 5C show (A) messenger RNA, (B) genomic, and (C) protein sequences of RAF1.

FIGS. 6A to 6C show (A) messenger RNA, (B) genomic, and (C) protein sequences of SOS1.

DETAILED DESCRIPTION

The present disclosure is, in part, based on the identification of mutations in RAS-specific guanine nucleotide exchange factor gene SOS1, which are causative for or closely associated with Noonan Syndrome (NS). In another aspect, the present disclosure pertains to mutations in serine/threonine protein kinase gene RAF1, which are causative for or closely associated with Noonan Syndrome (NS). In particular, the instant disclosure provides mutant SOS1 or RAF1 coding and non-coding nucleotide sequences associated with NS. The disclosure further provides SOS1 or RAF1 polypeptides that are encoded by such variant nucleic acids or comprise one or more amino acid residue substitutions, insertions, or deletions. In certain embodiments, the SOS1 or RAF1 polypeptide variants are characterized by a gain-of-function, i.e., an increase activity over basal levels; or by higher SOS1 or RAF1 expression levels, as compared to controls.

This disclosure also provides antibodies that specifically bind to these variant SOS1 or RAF1 polypeptides, as well as nucleic acids which may be used in the methods of this disclosure to detect a variant SOS1 or RAF1 nucleic acid. For example, in one embodiment, this disclosure provides oligonucleotides sequences which may be used, e.g., to detect a mutation in a SOS1 or RAF1 nucleic acid sequence, or to amplify a SOS1 or RAF1 nucleic acid molecule (for example, a specific locus on a SOS1 or RAF1 gene) having or suspected of having a mutation that correlates to or is indicative of NS.

Methods are also provided, as part of the present disclosure, in which nucleic acids, polypeptides and antibodies described herein are used to diagnose or treat NS. For example, this disclosure provides methods to evaluate individuals suspected of having NS (e.g., clinically showing phenotypic signs of NS) by detecting a variant SOS1 or RAF1 nucleic acid molecule or SOS1 or RAF1 polypeptide, respectively, such as one of the variants described herein, that statistically correlate to NS. This disclosure further provides methods to evaluate individuals suspected of having NS by detecting an increased level of activity in the SOS1 or RAF1 signaling pathway, for example, by comparing SOS1 or RAF1 or ERK2 activity to controls. In addition, this disclosure provides therapeutic methods for treating NS by administering a compound that modulates (e.g., enhances or inhibits) the expression or activity of either an SOS1 or a RAF1 nucleic acid molecule (e.g., a SOS1 or RAF1 gene) or an SOS1 or a RAF1 gene product (e.g., an SOS1 or RAF1 polypeptide). In one preferred embodiment, the compound modulates the activity of a variant SOS1 or RAF1 nucleic acid molecule or expression product thereof, such as one of the gain-of-function variants described herein.

By way of background and as set forth above, 50% of NS cases are a result of mutations in PTPN11 and KRAS genes (Carta et al., 2006; Tartaglia et al., 2001; U.S. Pat. Pub. No. 2003/0125289). Because other genetic causes of NS are not as prevalent as PTPN11 mutations, there are not as many or as extensive familial cohorts to examine for correlation of mutations to NS, as well as a way to examine penetrance of such mutations. Accordingly, in addition to the more rare familial cases of non-PTPN11/KRAS NS, parental genotypes were used to verify sporadic cases of NS. In particular, the instant disclosure describes the analysis of nucleic acid sequences that encode polypeptides with distinct roles in RAS-MAPK signaling—in particular, RAF1 and SOS1. Example 1 describes mutation screening in a cohort of human subjects, in which bi-directional sequencing of all RAF1 coding exons and their flanking intronic boundaries revealed mutations that form three identifiable clusters: one in conserved region 2 (CR2); one in conserved region 3 (CR3); and one at the carboxy-terminal domain. As used herein, "carboxy-terminal domain" refers to the final 50-75 amino acids nearest the carboxy-terminus of a polypeptide. Similar sequencing analysis of SOS1 revealed mutations that form three identifiable clusters: one in the Pleckstrin Homology (PH) domain; one in the linker between the PH domain and the (Rem) domain; and one at sites that form interacting regions between the Dbl homology (DH) and RAS exchanger motif (Rem) domain (i.e., functional mutations). These clustered sequence changes in RAF1 and SOS1 were absent in control individuals. Example 2 describes activity analysis of the RAF1 and SOS1 protein mutants. Example 3 describes the identification of additional mutations and further characterization of the role of the identified mutations in Noonan syndrome. Taken together, these findings establish RAF1 and SOS1 as NS disease genes.

Prior to setting forth this disclosure in more detail, it may be helpful to an understanding thereof to provide definitions of certain terms to be used herein.

Any concentration ranges recited herein are to be understood to include concentrations of any integer within that range and fractions thereof, such as one tenth and one hundredth of an integer, unless otherwise indicated. Also, any number range recited herein relating to any physical feature (such as number of nucleotides or amino acids), or size or thickness is to be understood to include any integer within the recited range, unless otherwise indicated. It should be understood that the terms "a" and "an" as used herein refer to "one or more" of the enumerated components. As used herein, the term "about" or "consisting essentially of" means±15% of a particular value, range or structure. As used herein, the terms "include" and "comprise" are used synonymously. The use of the alternative (e.g., "or") should be understood to mean either one, both or any combination thereof of the alternatives.

As used herein, "autoinhibition" refers to proteins or polypeptides that have autoinhibitory domains that negatively regulate the function of other domains via intramolecular or intermolecular interactions. Autoinhibition can be inhibited or reduced or counteracted by mutations, proteolysis, post-translational modifications, other proteins, small molecules, and the like. For example, SOS1 is guanine nucleotide exchange factor, which has a catalytic site and an allosteric site, and its activity is regulated by autoinhibition. The basal catalytic output of SOS1 is autoinhibited by two other SOS1 domains—Dbl homology (DH) domain and Pleckstrin homology (PH) domain—that form a DH-PH unit that mediates a blockade of the allosteric site, as described further herein. In another example, RAF1 is autoinhibited when the amino-terminal portion of RAF1 interacts with and inactivates the kinase domain at the carboxy-terminus. This autoinhibited conformation is stabilized by 14-3-3 protein dimers that bind to phosphorylated Ser259 and Ser621 of RAF1. In certain embodiments, autoinhibition of RAF1 or SOS1 is reduced or inhibited or counteracted by mutations as described herein.

(a) Noonan Syndrome (NS)

As used herein, the term "Noonan syndrome" or "NS" refers to disorders and diseases described under Accession No. OMIM 163950 (see the Online Mendelian Inheritance in Man (OMIM) database at the NCBI website, as of Nov. 13, 2006) and which are correlated to, associated with, or caused by a mutation in an SOS1 or RAF1 nucleic acid molecule, or a variant SOS1 or RAF1 polypeptide. Thus, the present disclosure takes into consideration that NS and its related disorders share some phenotypical features, but are genetically heterogeneous. In a preferred embodiment, NS has a mutation in an SOS1 or RAF1 nucleic acid molecule that encodes a gain-of-function variant SOS1 or RAF1 polypeptide, respectively. NS may be correlated to, associated with, or caused by a familial form or a sporadic form, such as by mutations in an SOS1 or RAF1 nucleic acid molecule as described herein.

The phenotypic features of NS have been well described and a clinical scoring system devised. See, Mendez and Opitz, *Am. J. Med. Genet.* 21:493-506, 1985; Noonan, *Clin. Pediatr.* (Phila) 33:548-555, 1994; Sharland et al., *Arch. Dis. Child* 67:178-183, 1992; Duncan et al., *Am. J. Med. Genet.* 10:37-50, 1981). But, the phenotypic features of NS can be quite varied and are similar to other disorders, such as cardio-facio-cutaneous (CFC) syndrome, LEOPARD syndrome, etc. In addition, phenotypic heterogeneity within syndromes, phenotypic overlap between syndromes, and age-related penetrance of certain features makes precise diagnosis difficult at certain ages, particularly in infants.

For purposes of clinical diagnosis, a "person suspected of having NS," as used herein, refers to those persons having NS disorders as described under Accession No. OMIM 163950 (previously referred to as male Turner and female pseudo-Turner Syndrome, as well as Turner phenotype with normal karyotype; see OMIM No. 163950), as well as disorders similar, or related, to NS. Exemplary NS-related disorders include the Watson (OMIM No. 193520) and LEOPARD (OMIM No. 151100) Syndromes, essentially clinically indistinguishable from NS (Mendez and Opitz, *Am. J. Med. Genet.* 21:493-506, 1985); Costello Syndrome (OMIM No. 218040; Costello, *Am. J. Med. Genet.* 62:199-201, 1996; Aoki et al., *Nature Genet.* 37:1038-40, 2005); cardiofaciocutaneous (CFC) syndrome (OMIM No. 115150; Reynolds et al., *Am. J. Med. Genet.* 25:413-27, 1986; Wieczorek et al., *Clin. Genet.* 52:37-46, 1997; Niihori et al., *Nature Genet.* 38:294-96, 2006; Rodriguez-Viciana et al., *Science* 311:1287-90, 2006); Noonan syndrome with multiple giant-cell lesions (OMIM No. 163955; Tartaglia et al., *Am. J. Hum. Genet.* 70:1555-63, 2002) and/or Noonan syndrome with multiple café-au-lait spots (also known as LEOPARD syndrome, MIM 151100; Digilio et al., *Am. J. Hum. Genet.* 71:389-94, 2002; Legius et al., *J. Med. Genet.* 39:571-4, 2002); valvular sclerosis (Snellen et al., *Circulation* 38(1 Suppl):93-101, 1968); and idiopathic short stature (Attie, *Curr. Opin. Pediatr.* 12:400-4, 2000). In view of the heterogeneous phenotypes and symptoms of NS, the present disclosure provides a molecular genetic tool for verifying a preliminary clinical diagnosis of NS and, thus, provides a method for distinguishing NS from the other phenotypically-related diseases or disorders.

The subject to whom the diagnostic or therapeutic applications of this disclosure are directed may be any human or animal, more particularly a mammal, preferably a primate or a rodent, and including monkeys, dogs, cats, horses, cows, pigs, sheep, goats, rabbits, guinea pigs, hamsters, mice and rats. In a preferred embodiment, the person suspected of having NS is a human. In other embodiments, the subject may be of any age (e.g., an adult, a child, an infant), which includes prenatal diagnostics and therapeutics interventions.

(b) RAF1

RAF1, also known as CRAF, KRAF, and MIL, is a member of the family of serine/threonine protein kinases (Wellbrock et al., Nat. Rev. Mol. Cell Biol. 5:875-85, 2004). By way of background, mammalian genomes contain three related RAF genes, which encode ARAF, BRAF, and RAF1 (also known as CRAF), respectively. BRAF, which is archetypal, has the highest MEK (ERK kinase) activity and relatively simpler regulation (Wellbrock et al., 2004). In contrast, ARAF and RAF1 have complex regulation, which may include activation by BRAF. Complete loss of Raf1 in mice is embryonic lethal, although cells appear to have intact Ras-Mapk signaling (Huser et al., Embo J 20:1940-51, 2001; Mikula et al., Embo J. 20:1952-62, 2001). To date, mutations in RAF1 have not been observed in human disease (OMIM No. 164760, at the NCBI website; see also Catalogue of Somatic Mutations in Cancer at the Wellcome Trust Sanger Institute website.

As used herein, the term "*RAF1*" in italicized form refers to a nucleic acid sequence (genomic, mRNA, cDNA, etc.), whereas the non-italicized form refers to a polypeptide or protein sequence.

In one aspect of the present disclosure, the RAF1 gene organization and intron boundary sequences are identified based on known genomic (found within GenBank Accession No. NT_022517; i.e., at 12,600,108 bp-12,680,678 bp from pter on chromosome 3 (3p25.2)—SEQ ID NO:5) and cDNA sequences (Genbank Accession No. NM_002880; nucleotide and amino acid sequences represented herein as SEQ ID NOS:1 and 2, respectively). In the context of the present disclosure, a RAF1 gene encompasses a nucleic acid molecule of human origin, comprising a coding nucleotide sequence set forth in SEQ ID NO:1, or homologs thereof, including allelic variants and orthologs.

"RAF1 variant" nucleic acid molecules are RAF1 genomic DNA, cDNA, or mRNA comprising at least one mutation, preferably a nucleotide substitution. The nucleotide substitution may be in a coding or non-coding region. In certain embodiments, RAF1 variants are those encoding RAF1 variants having increased RAF1 activity (i.e., "gain-of-function" variants), or those that result in the expression of higher levels of RAF1 as compared to a control.

The RAF1 protein encompasses a RAF1 protein of human origin having the amino acid sequence set forth in SEQ ID NO:2, or homologs thereof, including orthologs thereof. FIG. 1 shows the organization of the functional domains of the RAF1 polypeptide, a 73 KDa multidomain polypeptide. A RAF1 polypeptide comprises three Conserved Region domains (CR1, CR2, CR3) and a carboxy-terminal domain. The CR1 includes as cysteine-rich domain (CRD) and a Ras-binding domain (RBD), and the CR3 domain includes a kinase activation segment (see FIG. 1). "RAF1 variants" refers to RAF1 proteins or polypeptides comprising at least one mutation. A RAF1 variant can be a function-conservative variant, including gain-of-function-variants, i.e., variants capable of increased RAF1 activity, such as higher serine/threonine protein kinase activity. An increase in RAF1 activity includes, for example, increased serine/threonine protein kinase activity, prolonged activity of RAF1, or a higher proportion of RAF1 remaining in an active state (e.g., dephosphorylated). This may be assessed either by direct measurement of RAF1 activity or by measuring the activity of components regulated by RAF1 activity (see Example 2). In certain embodiments, RAF1 has mutations that result in an amino acid substitution, such as those described in FIG. 1 and Table 1.

Basal level of RAF1 activity is dependent on the conformation of the protein. RAF1 is highly regulated with numerous serine (S or Ser) and threonine (T or Thr) residues that can be phosphorylated, resulting in activation or inactivation (Wellbrock et al., 2004; Dougherty et al., *Mol. Cell* 17:215-24, 2005). The amino-terminal portion of RAF1 is thought to interact with and inactivate the kinase domain at the carboxy-terminus when RAF1 is in an inactive conformation. This conformation is stabilized by 14-3-3 protein dimers that bind to phosphorylated Ser259 and Ser621 (Muslin et al., *Cell* 84:889-97, 1996). The consensus 14-3-3 recognition sequence is R-S-X-$S^P$-X-P (Id.). Also, phosphorylation of Ser621 and subsequent 14-3-3 binding may be involved in RAF1 activation. Dephosphorylation of Ser259, which is mediated by protein phosphatase-2A (PP2A), facilitates binding of RAS-GTP at the membrane and subsequent propagation of the signal through the RAS-MAPK cascade via RAF1's MEK kinase activity. Without wishing to be bound to any specific theory, it appears that mutations associated with NS are in RAF1 amino acids that would favor an active confirmation—for example, Arg256, Ser257, Ser259, and Pro261 are all invariant residues within the 14-3-3 recognition motif of RAF1 and all were identified as mutations that correlate with or are a cause of NS (see Example 1).

An "increased activity" of RAF1 in a subject suspected of having NS or a biological sample from such a subject refers to a higher total RAF1 activity in the subject or biological sample in comparison with a control, e.g., a healthy subject or a standard sample. In certain embodiments, the RAF1 activity is at least about 10% to about 50% of a control, preferably at least about 100% to at least about 150% higher in the subject or sample than in the control. As provided by the instant disclosure, the increased activity may result from increased basal RAF1 activity, prolonged stimulation of a downstream component (e.g., ERK2 activity or RAS signaling) of an RAF1-associated pathway, and a higher RAF1 expression level. A higher RAF1 expression level may result from, for example, a mutation in a non-coding region of an RAF1 nucleic acid sequence or a mutation in a coding or non-coding gene involved in RAF1 transcription or translation. The expression level of RAF1 can be determined, for example, by comparing RAF1 mRNA or levels of RAF1 protein in a subject suspected of having NS as compared to a control.

(c) SOS1

SOS1, also known as Son of Sevenless homolog 1, SOS-1, GF-1, GGF-1, GINGF, and HGF, is a member of the family of RAS-specific guanine nucleotide exchange factors and is widely expressed along with SOS2 (Bowtell et al., *Proc. Nat'l. Acad. Sci. USA* 89:6511-5, 1992). By way of background, one step in the activation of the RAS-MAPK pathway is the ligand-dependent conversion of RAS-GDP to RAS-GTP. In the context of receptor tyrosine kinase (RTK) signaling, this reaction is catalyzed by the RAS-specific guanine nucleotide exchange factor (GEF) Son of Sevenless (SOS) (Nimnual and Bar-Sagi, *Sci STKE* 2002, PE36, 2002). Structural studies of SOS1, one of two human SOS proteins (the other being SOS2), indicate that basally the protein is auto-inhibited due to complex regulatory intra- and inter-molecular interactions (Corbalan-Garcia et al., *Mol. Cell Biol.* 18:880-6, 1998; Sondermann et al., *Proc. Nat'l. Acad. Sci. USA* 102, 16632-7, 2005; Sondermann et al., *Cell* 119:393-405, 2004). Following RTK stimulation, SOS1 is recruited to the plasma membrane where it acquires a catalytically active conformation through an as-yet ill-defined mechanism.

As used herein, the term "SOS1" in italicized form refers to a nucleic acid sequence (genomic, mRNA, cDNA, etc.), whereas the non-italicized form refers to a polypeptide or protein sequence.

In one aspect of the present disclosure, the SOS1 gene organization and intron boundary sequences are identified based on known genomic (found within GenBank Accession No. NT_022184; i.e., at 39,066,469 bp-39,201,067 bp from pter on chromosome 2 (2p22.1)—SEQ ID NO:6) and cDNA sequences (Genbank Accession No. NM_005633; nucleotide and amino acid sequences represented herein as SEQ ID NOS:3 and 4, respectively). In the context of the present disclosure, an SOS1 gene encompasses a nucleic acid molecule of human origin, comprising a coding nucleotide sequence set forth in SEQ ID NO:3, or homologs thereof, including allelic variants and orthologs.

Figure 2A:
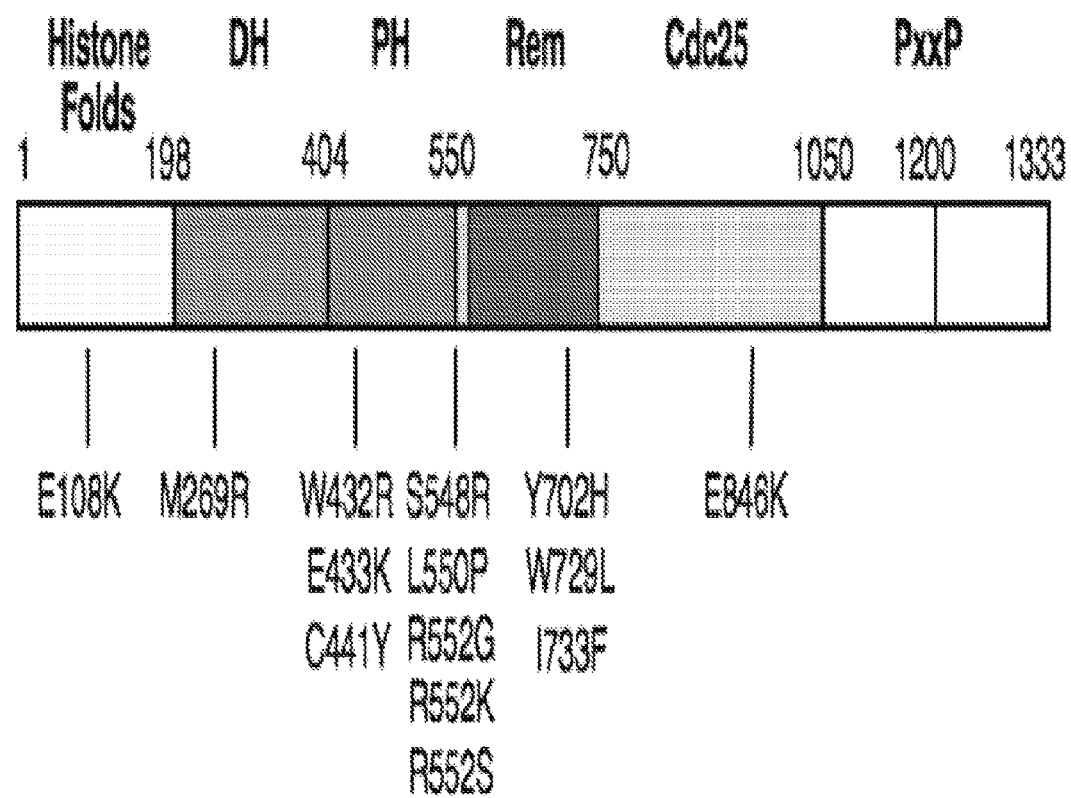
FIGS. 2A and 2B show a two-dimensional SOS1 domain structure and location of residues altered in Noonan syndrome, and the location of mutated residues on a three-dimensional illustration of SOS1. (A) The predicted amino acid substitutions from the 14 SOS1 missense mutations are positioned below the cartoon of the SOS1 protein with its functional domains indicated above. Abbreviations: DH, Dbl homology domain; PH, Pleckstrin homology domain; Rem, RAS exchanger motif. (B) The functional domains are shown as follows: DH; PH; PH-Rem helical linker; Rem; Cdc25. Residues affected by mutations are indicated with their lateral chains and numbered.

The SOS1 protein encompasses an SOS1 protein of human origin having the amino acid sequence set forth in SEQ ID NO:4, or homologs thereof, including orthologs thereof. FIG. 2A shows the organization of the functional domains of the SOS1 polypeptide, a 150 KDa multidomain polypeptide. An SOS1 polypeptide comprises a histone folds domain, a Dbl Homology (DH) domain, a Pleckstrin Homology (PH) domain, a RAS exchanger motif (Rem), a PH-Rem helical linker, a CDC25 homology (Cdc25) domain, and a praline rich Grbs binding domain (PxxP).

"SOS1 variant" nucleic acid molecules are SOS1 genomic DNA, cDNA, or mRNA comprising at least one mutation, preferably a nucleotide substitution. The nucleotide substitution may be in a coding or non-coding region. In certain embodiments, SOS1 variants are those encoding SOS1 variants having increased SOS1 activity (i.e., "gain-of-function" variants), or those that result in the expression of higher levels of SOS1 as compared to a control.

Figure 2B:
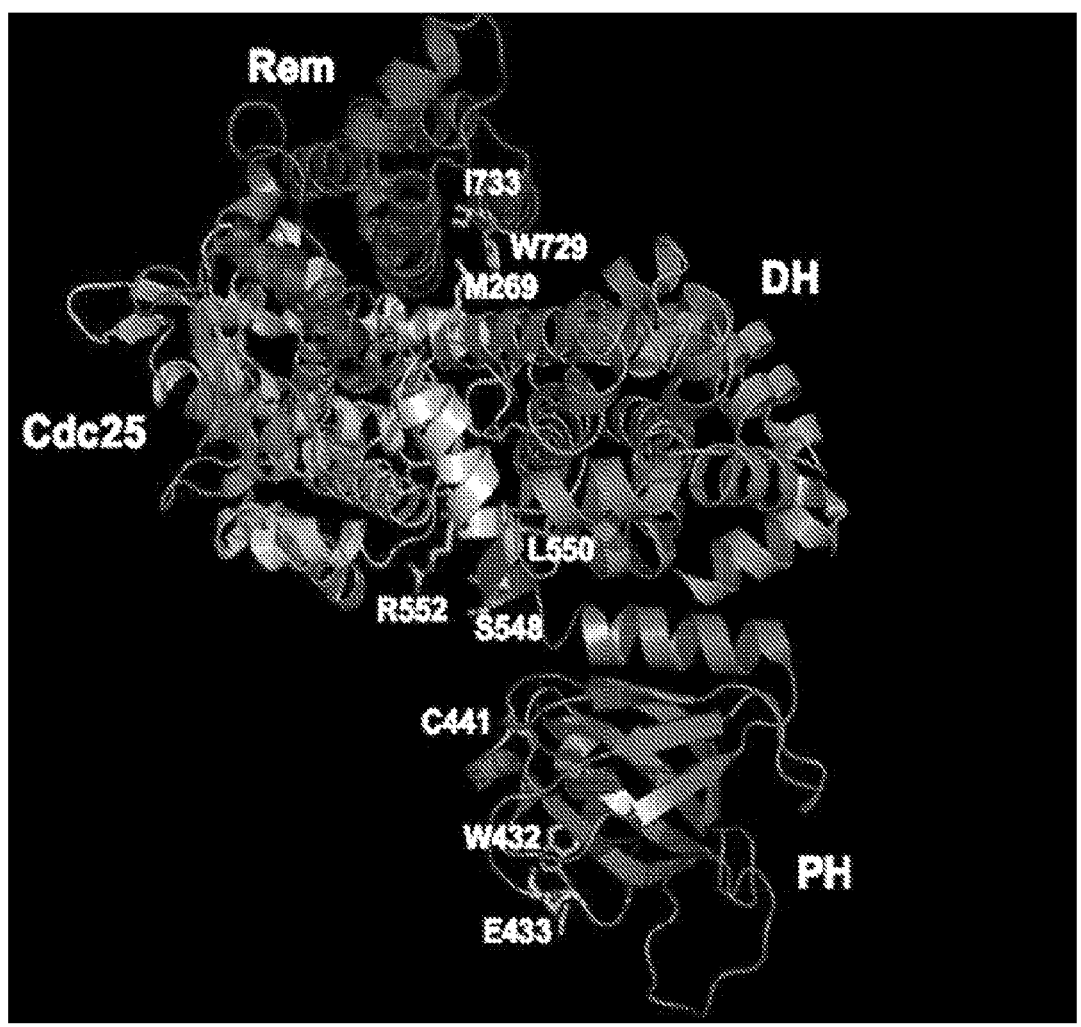

"SOS1 variants" are SOS1 proteins or polypeptides comprising at least one mutation. The SOS1 variants can be function-conservative variants, including gain-of-function-variants, i.e., variants capable of increased SOS1 activity, such as higher guanine nucleotide exchange activity or reduced autoinhibition activity. An increase in SOS1 activity includes, for example, increased guanine nucleotide exchange activity, prolonged activity of SOS1, or a higher proportion of SOS1 remaining in an active state (e.g., reduced autoinhibition activity). This may be assessed either by direct measurement of SOS1 activity or by measuring the activity of components regulated by SOS1 activity (see, Example 4). In certain embodiments, SOS1 has mutations that result in an amino acid substitution, such as those described in FIG. 2 and Table 2.

Basal level of SOS1 activity is dependent on the conformation of the protein. The GEF activity of SOS1 is principally controlled by two regulatory determinants; a catalytic site that forms a stable interaction with nucleotide-free RAS, and an allosteric site that potentiates exchange activity through the binding of nucleotide-bound RAS (Margarit et al., *Cell* 112:685-95, 2003). Whereas the former is located entirely within the Cdc25 domain, the allosteric site is bracketed by the Cdc25 domain and Rem domains. Basally, the catalytic output of SOS1 is constrained by the DH-PH unit (Corbalan-Garcia et al., 1998), and structural data indicate that this autoinhibitory effect is exerted through DH-PH-mediated blockade of the allosteric site (Sondermann et al., 2004). Without wishing to be bound to any specific theory, it appears that the SOS1 mutations observed in Noonan syndrome are in residues that contribute to autoinhibition, either by stabilizing the interaction of the histone folds with the PH-Rem linker or interaction of the DH domain with the Rem domain, so it is believed that the predominant pathogenetic mechanism may be a release of autoinhibition followed by an enhanced GEF activity and, as a consequence, increased RAS-GTP levels (see Example 2).

An "increased activity" of SOS1 in a subject suspected of having NS or a biological sample from such a subject refers to a higher total SOS1 activity in the subject or biological sample in comparison with a control, e.g., a healthy subject or a standard sample. In certain embodiments, the SOS1 activity is at least about 10% to about 50% higher in the subject or sample than in a control, and preferably at least about 100% to at least about 150% higher in the subject or sample than in a control. As provided by the instant disclosure, the increased activity may result from increased basal SOS1 activity, prolonged stimulation of a downstream component (e.g., ERK2 activity or RAS signaling) of an SOS1-associated pathway, and a higher SOS1 expression level. A higher SOS1 expression level may result from, for example, a mutation in a non-coding region of an SOS1 nucleic acid sequence or a mutation in a coding or non-coding gene involved in SOS1 transcription or translation. The expression level of SOS1 can be determined, for example, by comparing SOS1 mRNA or levels of SOS1 protein in a subject suspected of having NS as compared to a control.

(d) RAS-MAPK Signaling Pathway

As set forth above, RAF1 and SOS1 participate in the RAS-MAPK signaling cascade. In certain embodiments, a "RAF1 signaling pathway" or "SOS1 signaling pathway" refers to a RAS-MAP kinase pathway (ERK1/2). Briefly, transmission of stimulatory signals from Ras to nuclear targets involves regulation of the family of kinases known as MAPKs ("mitogen-activated protein kinases") or ERKs ("extracellular signal regulated kinases"). This pathway includes, but is not limited to, components such as RAF1, SOS1, and ERK2. Additional components of this pathway have been identified and described (see, e.g., Lee and McCubrey, *Leukemia* 16:486-507, 2002).

An "up regulation" or "increased activity" of a RAF1 or an SOS1 signaling pathway such as the RAS-MAPK pathway herein means a detectable change in signaling flux or output of the pathway that could also result from a gain-of-function RAF1 or SOS1 mutant. In certain embodiments, examples of output signals include an increased RAF1 or SOS1 activity, or increased ERK2 kinase activity. See Example 2 and FIG. 4.

(e) Molecular Biology Terms

In accordance with the present disclosure there may be employed conventional molecular biology, microbiology, and recombinant DNA techniques within the skill of the art. Such techniques are explained fully in the literature. See, e.g., Sambrook, Fritsch & Maniatis, *Molecular Cloning: A Laboratory Manual*, Second Edition (1989) Cold Spring Harbor Laboratory Press, Cold Spring Harbor, N.Y. (herein "Sambrook et al., 1989"); *DNA Cloning: A Practical Approach*, Volumes I and II (D. N. Glover ed. 1985); *Oligonucleotide Synthesis* (M. J. Gait ed. 1984); *Nucleic Acid Hybridization* (B. D. Hames & S. J. Higgins eds. (1985)); *Transcription And Translation* (B. D. Hames & S. J. Higgins, eds. (1984)); *Animal Cell Culture* (R. I. Freshney, ed. (1986)); *Immobilized Cells And Enzymes* (IRL Press, (1986)); B. Perbal, *A Practical Guide To Molecular Cloning* (1984); F. M. Ausubel et al. (eds.), *Current Protocols in Molecular Biology*, John Wiley & Sons, Inc. (1994).

The terms "polypeptide" and "protein" may be used herein interchangeably to refer to the gene product (or corresponding synthetic product) of a RAF1 or SOS1 nucleic acid molecule. The term "protein" may also refer specifically to the polypeptide as expressed in cells.

A "RAF1 gene" or "SOS1 gene," as used herein, refers to a portion of a DNA molecule that includes a RAF1 or an SOS1 polypeptide coding sequence, respectively, operably linked to one or more expression control sequences. Thus, a gene includes both transcribed and untranscribed regions. The transcribed region may include introns, which are spliced out of the mRNA, and 5'- and 3'-untranslated (UTR) sequences along with protein coding sequences. In one embodiment, the gene can be a genomic or partial genomic sequence, in that it contains one or more introns. In another embodiment, the term gene may refer to a cDNA molecule (i.e., the coding sequence lacking introns). In yet another embodiment, the term gene may refer to expression control sequences, such as the promoter or the enhancer sequence.

A "promoter sequence" is a nucleic acid regulatory region capable of binding RNA polymerase and initiating transcription of a downstream (3' direction) coding sequence. For purposes of the present disclosure, the promoter sequence is bounded at its 3' terminus by the transcription initiation site and extends upstream (5' direction) to include the minimum number of bases or elements necessary to initiate transcription at levels detectable above background. Within the promoter sequence will be found a transcription initiation site (conveniently defined for example, by mapping with nuclease S1), as well as protein binding domains (consensus sequences) responsible for the binding of RNA polymerase.

"Sequence-conservative variants" of a polynucleotide sequence are those in which a change of one or more nucleotides in a given codon position results in no alteration in the amino acid encoded at that position.

"Function-conservative variants" are those in which a given amino acid residue in a protein or enzyme has been changed without altering the overall conformation and function of the polypeptide, including replacement of an amino acid with one having similar properties (such as, for example, polarity, hydrogen bonding potential, acidic, basic, hydrophobic, aromatic, and the like). Amino acids with similar properties are well known in the art. For example, arginine, histidine and lysine are hydrophilic-basic amino acids and may be interchangeable. Similarly, isoleucine, a hydrophobic amino acid, may be replaced with leucine, methionine or valine. Such changes are expected to have little or no effect on the apparent molecular weight or isoelectric point of the protein or polypeptide.

Amino acids other than those indicated as conserved may differ in a protein or enzyme so that the percent protein or amino acid sequence identity between any two proteins of similar function may vary and may be, for example, from about 70% to about 99% as determined according to an alignment scheme, such as by the Cluster Method, wherein percent identity between sequences is based on the MEGALIGN algorithm. A "variant" also includes a polypeptide or enzyme that has at least about 60% amino acid identity as determined by BLAST or FASTA algorithms, preferably at least about 75%, most preferably at least about 85%, and even more preferably at least about 90%, and still more preferably at least about 95%, and which has the same or substantially similar properties or functions as the native or parent protein or enzyme to which it is compared. In certain embodiments, a variant is a "gain-of-function" variant, meaning a polypeptide variant in which the change of at least one given amino acid residue in a protein or enzyme improves a specific function of the polypeptide, including protein activity. The change in amino acid residue can be replacement of an amino acid with one having similar properties (such as, for example, polarity, hydrogen bonding potential, acidic, basic, hydrophobic, aromatic, and the like) or different properties, or may be due to a deletion or insertion or a combination thereof.

As used herein, the term "homologous" in all its grammatical forms and spelling variations refers to the relationship between proteins that possess a "common evolutionary origin," including proteins from superfamilies (e.g., the immunoglobulin superfamily) and homologous proteins from different species (e.g., myosin light chain, etc.) (Reeck et al., Cell 50:667, 1987). Such proteins (and their encoding genes) have sequence homology, as reflected by their sequence similarity, whether in terms of percent identity or the presence of specific amino acids or motifs at conserved positions.

Accordingly, the term "sequence similarity" or "sequence identity" in all their grammatical forms refers to the degree of identity or correspondence between nucleic acid or amino acid sequences of proteins that may or may not share a common evolutionary origin (see Reeck et al., supra). However, in common usage and in the instant application, the term "homologous," when modified with an adverb such as "highly," may refer to sequence similarity and does not necessarily relate to a common evolutionary origin.

In a specific embodiment, two DNA sequences are "substantially homologous" or "substantially identical" when at least about 80%, and most preferably at least about 90 or at least about 95%) of the nucleotides match over the defined length of the DNA sequences, as determined by sequence comparison algorithms, such as BLAST, FASTA, DNA Strider, etc. An example of such a sequence is an allelic or species variant of a RAF1 or SOS1 nucleic acid molecule. Sequences that are substantially homologous can be identified by comparing the sequences using standard software available in sequence data banks, or in a Southern hybridization experiment under, for example, stringent conditions as defined for that particular system.

Similarly, in a particular embodiment, two amino acid sequences are "substantially homologous" or "substantially identical" when greater than about 80% of the amino acids are identical, or greater than about 90% or about 95% are similar (functionally identical). In certain embodiments, the similar or homologous sequences are identified by alignment using, for example, the GCG (Genetics Computer Group, Program Manual for the GCG Package, Version 7, Madison, Wis.) pileup program using the default parameters, or using any of the programs described herein (BLAST, FASTA, etc.).

A nucleic acid molecule is "hybridizable" to another nucleic acid molecule, such as a cDNA, genomic DNA, or RNA, when a single stranded form of the nucleic acid molecule can anneal to the other nucleic acid molecule under the appropriate conditions of temperature and solution ionic strength (see Sambrook et al.). The conditions of temperature and ionic strength determine the "stringency" of the hybridization. For preliminary screening for homologous nucleic acids, low stringency hybridization conditions, corresponding to a $T_m$ (melting temperature) of 55° C., can be used, e.g., 5×SSC, 0.1% SDS, 0.25% milk, and no formamide; or 30% formamide, 5×SSC, 0.5% SDS). Moderate stringency hybridization conditions correspond to a higher $T_m$, e.g., 40% formamide, with 5× or 6×SCC. High stringency hybridization conditions correspond to the highest $T_m$, e.g., 50% formamide, 5× or 6×SCC. SCC is a 0.15M NaCl, 0.015M Na-citrate. Hybridization requires that the two nucleic acids contain complementary sequences, although depending on the stringency of the hybridization, mismatches between bases are possible. The appropriate stringency for hybridizing nucleic acids depends on the length of the nucleic acids and the degree of complementation, variables well known in the art. The greater the degree of similarity or homology between two nucleotide sequences, the greater the value of $T_m$ for hybrids of nucleic acids having those sequences. The relative stability (corresponding to higher $T_m$) of nucleic acid hybridizations decreases in the following order: RNA:RNA, DNA: RNA, DNA:DNA. For hybrids of greater than 100 nucleotides in length, equations for calculating $T_m$ have been derived (see Sambrook et al., supra, 9.50-9.51). For hybridization with shorter nucleic acids, i.e., oligonucleotides, the position of mismatches becomes more important, and the length of the oligonucleotide determines its specificity (see Sambrook et al., supra, 11.7-11.8). A minimum length for a hybridizable nucleic acid is at least about 10 nucleotides; preferably at least about 15 nucleotides; and more preferably the length is at least about 20 nucleotides.

In a specific embodiment, the term "standard hybridization conditions" refers to a $T_m$ of 55° C., and utilizes conditions as set forth above. In a preferred embodiment, the $T_m$ is 60° C.; in a more preferred embodiment, the $T_m$ is 65° C. In a specific embodiment, "high stringency" refers to hybridization or washing conditions at 68° C. in 0.2×SSC, at 42° C. in 50% formamide, 4×SSC, or under conditions that afford levels of hybridization equivalent to those observed under either of these two conditions.

The terms "mutant" and "mutation" mean any detectable change in genetic material, e.g., DNA, or any process, mechanism, or result of such a change. When compared to a control material, such change may be referred to as a "variant" or an "abnormality". This includes gene mutations, in which the structure (e.g., DNA or RNA sequence) of a gene is altered, arising from any mutation process, and any expression product (e.g., protein or enzyme) expressed by such a modified gene or DNA sequence. The term "variant" may also be used to indicate a modified or altered gene, DNA sequence, enzyme, cell, etc., i.e., any kind of mutant.

"Amplification" of DNA as used herein encompasses the use of polymerase chain reaction (PCR) to increase the concentration of a particular DNA sequence within a mixture of DNA sequences. For a description of PCR, see Saiki et al., Science 239:487, 1988.

"Sequencing" of a nucleic acid includes chemical or enzymatic sequencing. "Chemical sequencing" of DNA denotes methods such as that of Maxam and Gilbert (Maxam-Gilbert sequencing, Maxam and Gilbert, Proc. Nat'l. Acad. Sci. USA 74:560, 1977), in which DNA is randomly cleaved using individual base-specific reactions. "Enzymatic sequencing" of DNA denotes methods such as that of Sanger (Sanger et al., Proc. Nat'l. Acad. Sci. USA 74:5463, 1977), in which a single-stranded DNA is copied and randomly terminated using DNA polymerase, including variations thereof, which are well-known in the art. Preferably, oligonucleotide sequencing is conducted using automatic, computerized equipment in a high-throughput setting, for example, microarray technology, as described herein. Such high-throughput equipment are commercially available, and techniques well known in the art.

The term "polymorphism" refers, generally, to the coexistence of more than one form of a gene (e.g., more than one allele) within a population of individuals and is not necessarily associated or correlated with a disorder or disease. The different alleles may differ at one or more positions of their nucleic acid sequences, which are referred to herein as "polymorphic locuses". When used herein to describe polypeptides that are encoded by different alleles of a gene, the term "polymorphic locus" also refers to the positions in an amino acid sequence that differ among variant polypeptides encoded by different alleles. Polymorphisms include "single nucleotide polymorphisms" (SNPs), referring to a polymorphic site occupied by a single nucleotide, which is the site of variation between allelic sequences. Typically, the polymorphic site of an SNP is flanked by highly conserved sequences (e.g., sequences that vary in less than 1/100 and, more preferably, in less than 1/1000 individuals in a population). The polymorphic locus of an SNP may be a single base deletion, a single base insertion, or a single base substitution. Single base substitutions are particularly preferred.

As used herein, "sequence-specific oligonucleotides" refers to related sets of oligonucleotides that can be used to detect variations or mutations in a RAF1 or SOS1 gene.

A "probe" refers to a nucleic acid or oligonucleotide that forms a hybrid structure with a sequence in a target region due to complementarity of at least one sequence in the probe with a sequence in the target protein.

As used herein, the term "oligonucleotide" refers to a nucleic acid, generally of at least 10, preferably at least 15, and more preferably at least 20 nucleotides, preferably no more than 100 nucleotides, that is hybridizable to a genomic DNA molecule, a cDNA molecule, or an mRNA molecule encoding a gene, mRNA, cDNA, or other nucleic acid of interest. Oligonucleotides can be labeled, e.g., with $^{32}$P-nucleotides or nucleotides to which a label, such as biotin, has been covalently conjugated. In one embodiment, a labeled oligonucleotide can be used as a probe to detect the presence of a nucleic acid. In another embodiment, oligonucleotides (one or both of which may be labeled) can be used as PCR primers, either for cloning full length or a fragment of RAF1 or SOS1, or to detect the presence of nucleic acids encoding RAF1 or SOS1, respectively. In a further embodiment, an oligonucleotide of this disclosure can form a triple helix with a RAF1 or SOS1 nucleic acid molecule. In still another embodiment, a library of oligonucleotides arranged on a solid support, such as a silicon wafer or chip, can be used to detect various mutations of interest. Generally, oligonucleotides are prepared synthetically, preferably on a nucleic acid synthesizer. Accordingly, oligonucleotides can be prepared with non-naturally occurring phosphoester analog bonds, such as thioester bonds, etc.

Representative examples of synthetic oligonucleotides envisioned for this disclosure include oligonucleotides that contain phosphorothioates, phosphotriesters, methyl phosphonates, short chain alkyl, or cycloalkyl intersugar linkages or short chain heteroatomic or heterocyclic intersugar linkages. Most preferred are those with $CH_2$—NH—O—$CH_2$, $CH_2$—N($CH$)$_3$—O—$CH_2$, $CH_2$—O—N($CH$)$_3$—$CH_2$, $CH_2$—N($CH$)$_3$—N($CH$)$_3$—$CH_2$ and O—N($CH$)$_3$—$CH_2$—$CH_2$ backbones (where the phosphodiester is O—$PO_2$—O—$CH_2$). U.S. Pat. No. 5,677,437 describes heteroaromatic oligonucleoside linkages. Nitrogen linkers or groups containing nitrogen can also be used to prepare oligonucleotide mimics (U.S. Pat. Nos. 5,792,844 and 5,783,682). U.S. Pat. No. 5,637,684 describes phosphoramidate and phosphorothioamidate oligomeric compounds. Also envisioned are oligonucleotides having morpholino backbone structures (U.S. Pat. No. 5,034,506). In other embodiments, such as the peptide-nucleic acid (PNA) backbone, the phosphodiester backbone of the oligonucleotide may be replaced with a polyamide backbone, the bases being bound directly or indirectly to the aza nitrogen atoms of the polyamide backbone (Nielsen et al., *Science* 254:1497, 1991). Other synthetic oligonucleotides may contain substituted sugar moieties comprising one of the following at the 2' position: OH, SH, $SCH_3$, F, OCN, $O(CH_2)_nNH_2$ or $O(CH_2)_nCH_3$ where n is from 1 to about 10; $C_1$ to $C_{10}$ lower alkyl, substituted lower alkyl, alkaryl or aralkyl; Cl; Br; CN; $CF_3$; $OCF_3$; O—; S—, or N-alkyl; O-, S-, or N-alkenyl; $SOCH_3$; $SO_2CH_3$; $ONO_2$; $NO_2$; $N_3$; $NH_2$; heterocycloalkyl; heterocycloalkaryl; aminoalkylamino; polyalkylamino; substituted silyl; a fluorescein moiety; an RNA cleaving group; a reporter group; an intercalator; a group for improving the pharmacokinetic properties of an oligonucleotide; or a group for improving the pharmacodynamic properties of an oligonucleotide, and other substituents having similar properties. Oligonucleotides may also have sugar mimetics such as cyclobutyls or other carbocyclics in place of the pentofuranosyl group. Nucleotide units having nucleosides other than adenosine, cytidine, guanosine, thymidine and uridine, such as inosine, may be used in an oligonucleotide molecule.

The present disclosure provides antisense nucleic acids (including ribozymes), which may be used to inhibit expression of a RAF1 or SOS1 variant. An "antisense nucleic acid" or a "small interfering RNA" (siRNA) is a single stranded nucleic acid molecule which, on hybridizing under cytoplasmic conditions with complementary bases in an RNA or DNA molecule, inhibits the latter's role. If the RNA is a messenger RNA transcript, the antisense or siRNA nucleic acid is a countertranscript or mRNA-interfering complementary nucleic acid. As presently used, "antisense" broadly includes RNA-RNA interactions, RNA-DNA interactions, ribozymes and RNase-H mediated arrest. Antisense nucleic acid molecules can be encoded by a recombinant gene for expression in a cell (e.g., U.S. Pat. No. 5,814,500; U.S. Pat. No. 5,811,234), or alternatively they can be prepared synthetically (e.g., U.S. Pat. No. 5,780,607). Synthetic oligonucleotides are suitable for antisense use.

The terms "vector", "cloning vector" and "expression vector" mean the vehicle by which a DNA or RNA sequence (e.g., a RAF1 or SOS1 encoding nucleic acid sequence) can be introduced into a host cell under conditions and for a time sufficient to allow expression of the introduced sequence (e.g., transcription and translation). Vectors include plasmids, phages, viruses, yeast artificial chromosomes, or the like.

The term "linkage" refers to the tendency of genes, alleles, loci or genetic markers to be inherited together as a result of their location on the same chromosome. Linkage may be measured, e.g., by the percent recombination between two genes, alleles, loci or genetic markers.

Expression of RAF1 and SOS1 Polypeptides

A nucleic acid molecule that encodes RAF1 or SOS1, or that encodes an antigenic fragment, derivative or analog of RAF1 or SOS1, or a functionally active derivative of RAF1 or SOS1 (including a chimeric protein) may be inserted into an appropriate expression vector, i.e., a vector which contains the necessary elements for the transcription and translation of the inserted protein-coding sequence. Thus, a nucleic acid encoding a RAF1 or SOS1 polypeptide variant of this disclosure can be operably linked to a promoter in an expression vector of this disclosure. Both cDNA and genomic sequences can be cloned and expressed under control of such regulatory sequences. Such vectors can be used to express functional or functionally inactivated RAF1 or SOS1 polypeptides. In particular, the RAF1 or SOS1 nucleic acids which may be cloned and expressed according to these methods include wild-type RAF1 or SOS1 nucleic acid molecules, as well as mutant or variant RAF1 or SOS1 nucleic acid molecules. These variants include, for example, a RAF1 or SOS1 nucleic acid having one or more of the mutations or polymorphisms set forth in Tables 1 and 2, respectively. In addition, nucleic acids that encode a variant RAF1 or SOS1 polypeptide, such as a variant RAF1 or SOS1 polypeptide comprising one or more of the amino acid substitutions listed in Tables 1 and 2, respectively, may be cloned and expressed according to the methods described here.

The necessary transcriptional and translational signals can be provided on a recombinant expression vector. Potential host-vector systems include mammalian cell systems transfected with expression plasmids or infected with virus (e.g., vaccinia virus, adenovirus, adeno-associated virus, herpes virus, etc.); insect cell systems infected with virus (e.g., baculovirus); microorganisms such as yeast containing yeast vectors; or bacteria transformed with bacteriophage, DNA, plasmid DNA, or cosmid DNA. The expression elements of vectors vary in their strengths and specificities. Depending on the host-vector system utilized, any one of a number of suitable transcription and translation elements may be used.

Expression of a RAF1 or SOS1 polypeptide may be controlled by any promoter or enhancer element known in the art, but these regulatory elements must be functional in the host selected for expression. Promoters that may be used to control RAF1 or SOS1 gene expression include a cytomegalovirus (CMV) promoter (U.S. Pat. Nos. 5,385,839 and 5,168,062), an SV40 early promoter region (Benoist and Chambon, Nature 290:304-10, 1981), a promoter contained in the 3' long terminal repeat of Rous sarcoma virus (Yamamoto et al., Cell 22:787-97, 1980), a herpes thymidine kinase promoter (Wagner et al., Proc. Nat'l. Acad. Sci. U.S.A. 78:1441-5, 1981), regulatory sequences of the metallothionein gene (Brinster et al., Nature 296:39-42, 1982); prokaryotic expression vectors such as the β-lactamase promoter (Villa-Komaroff et al., Proc. Nat'l. Acad. Sci. U.S.A. 75:3727-31, 1978), or the tac promoter (DeBoer et al., Proc. Nat'l. Acad. Sci. U.S.A. 80:21-25, 1983); see also "Useful proteins from recombinant bacteria" in Scientific American 242:74-94, 1980. Still other useful promoter elements which may be used include promoter elements from yeast or other fungi such as the Gal 4 promoter, the ADC (alcohol dehydrogenase) promoter, PGK (phosphoglycerol kinase) promoter, alkaline phosphatase promoter; and transcriptional control regions that exhibit hematopoietic tissue specificity, in particular: beta-globin gene control region which is active in myeloid cells (Mogram et al., Nature 315:338-340, 1985; Kollias et al., Cell 46:89-94, 1986), hematopoietic stem cell differentiation factor promoters, erythropoietin receptor promoter (Maouche et al., Blood 15:2557, 1991), etc.

Soluble forms of the protein can be obtained by collecting culture fluid, or solubilizing-inclusion bodies, e.g., by treatment with detergent, and if desired sonication or other mechanical processes, as described above. The solubilized or soluble protein can be isolated using various techniques, such as polyacrylamide gel electrophoresis (PAGE), isoelectric focusing, 2 dimensional gel electrophoresis, chromatography (e.g., ion exchange, affinity, immunoaffinity, and sizing column chromatography), centrifugation, differential solubility, immunoprecipitation, or by any other standard technique for the purification of proteins.

A wide variety of host/expression vector combinations may be employed in expressing the DNA sequences of this disclosure. Useful expression vectors, for example, may consist of segments of chromosomal, non chromosomal and synthetic DNA sequences. Suitable vectors include derivatives of SV40 and known bacterial plasmids, e.g., E. coli plasmids col El, pCR1, pBR322, pMal-C2, pET, pGEX (Smith et al., Gene 67:31-40, 1988), pCR2.1 and pcDNA 3.1+(Invitrogen, Carlsbad, Calif.), pMB9 and their derivatives, plasmids such as RP4; phage DNAs, e.g., the numerous derivatives of phage 1, e.g., NM989, and other phage DNA, e.g., M13 and filamentous single stranded phage DNA; yeast plasmids such as the 2m plasmid or derivatives thereof; vectors useful in eukaryotic cells, such as vectors useful in insect or mammalian cells; vectors derived from combinations of plasmids and phage DNAs, such as plasmids that have been modified to employ phage DNA or other expression control sequences; and the like.

In certain embodiments, vectors can be viral vectors, such as lentiviruses, retroviruses, herpes viruses, adenoviruses, adeno-associated viruses, vaccinia virus, baculovirus, and other recombinant viruses with desirable cellular tropism. Thus, a gene encoding a functional or mutant RAF1 or SOS1 polypeptide or domain fragment thereof can be introduced in vivo, ex vivo, or in vitro using a viral vector or through direct introduction of a nucleic acid molecule. Expression in targeted tissues can be effected by targeting the transgenic vector to specific cells, such as with a viral vector or a receptor ligand, or by using a tissue-specific promoter, or both. Targeted gene delivery is described in International Patent Publication WO 95/28494, published October 1995.

Viral vectors commonly used for in vivo or ex vivo targeting and therapy procedures (see below), as well as in vitro expression, are DNA-based vectors and retroviral vectors. Methods for constructing and using viral vectors are known in the art (see, e.g., Miller and Rosman, BioTechniques 1992, 7:980-990). Preferably, the viral vectors are replication defective, that is, they are unable to replicate autonomously in the target cell. In general, the genomes of the replication defective viral vectors which are used within the scope of the present disclosure lack at least one region which is necessary for the replication of the virus in the infected cell. These regions can either be eliminated (in whole or in part), or can be rendered non-functional by any technique known to a person skilled in the art. These techniques include the total removal, substitution (by other sequences, in particular by the inserted nucleic acid), partial deletion or addition of one or more bases to an essential (for replication) region. Such techniques may be performed in vitro (on the isolated DNA) or in situ, using the techniques of genetic manipulation or by treatment with mutagenic agents. Preferably, the replication defective virus retains the sequences of its genome which are necessary for encapsidating the viral particles.

DNA viral vectors include an attenuated or defective DNA virus, such as but not limited to herpes simplex virus (HSV), papillomavirus, Epstein Barr virus (EBV), adenovirus, adeno-associated virus (AAV), baculovirus, and the like. RNA viral vectors include, for example, retroviruses, lentiviruses, and alphaviruses (e.g., Sindbis virus and Venezuelan Equine Encephalitis virus), and the like. Defective viruses, which entirely or almost entirely lack viral genes, are preferred. Defective virus is not infective after introduction into a cell. Use of defective viral vectors allows for administration to cells in a specific, localized area, without concern that the vector can infect other cells. Thus, a specific tissue can be specifically targeted. Examples of particular vectors include, but are not limited to, a defective herpes virus 1 (HSV1) vector (Kaplitt et al., Molec. Cell. Neurosci. 2:320-330, 1991), defective herpes virus vector lacking a glyco-protein L gene (Patent Publication RD 371005 A), or other defective herpes virus vectors (International Patent Publication No. WO 94/21807, published Sep. 29, 1994; International Patent Publication No. WO 92/05263, published Apr. 2, 1994); an attenuated adenovirus vector, such as the vector described by Stratford-Perricaudet et al., (J. Clin. Invest. 90:626-30, 1992; see also La Salle et al., Science 259:988-90, 1993); and a defective adeno-associated virus vector (Samulski et al., J. Virol. 61:3096-3101, 1987; Samulski et al., J. Virol. 63:3822-8, 1989; Lebkowski et al., Mol. Cell. Biol. 8:3988-96, 1988).

Various companies produce viral vectors commercially, including but by no means limited to Avigen, Inc. (Alameda, Calif.; AAV vectors), Cell Genesys (Foster City, Calif.; retroviral, adenoviral, AAV vectors, and lentiviral vectors), Clontech (retroviral and baculoviral vectors), Genovo, Inc. (Sharon Hill, Pa.; adenoviral and AAV vectors), Genvec (adenoviral vectors), IntroGene (Leiden, Netherlands; adenoviral vectors), Molecular Medicine (retroviral, adenoviral, AAV, and herpes viral vectors), Norgen (adenoviral vectors), Oxford BioMedica (Oxford, United Kingdom; lentiviral vectors), Transgene (Strasbourg, France; adenoviral, vaccinia, retroviral, and lentiviral vectors) and Invitrogen (Carlsbad, Calif.).

In another embodiment, the vector can be introduced in vivo by lipofection, as naked DNA, or with other transfection facilitating agents (peptides, polymers, etc.). Synthetic cationic lipids can be used to prepare liposomes for in vivo transfection of a gene encoding a marker (Felgner et al., *Proc. Nat'l. Acad. Sci. U.S.A.* 1987, 84:7413-7417; Feigner and Ringold, *Science* 337:387-88, 1989; Mackey et al., *Proc. Nat'l Acad. Sci. U.S.A.* 85:8027-31, 1988; Ulmer et al., *Science* 259:1745-48, 1993). Useful lipid compounds and compositions for transfer of nucleic acids are described in International Patent Publications WO 95/18863 and WO 96/17823, and in U.S. Pat. No. 5,459,127. Lipids may be chemically coupled to other molecules for the purpose of targeting (see Mackey et al., *Proc. Nat'l. Acad. Sci. U.S.A.* 85:8027-31, 1988). Targeted peptides, and proteins such as antibodies, or non-peptide molecules could be coupled to liposomes chemically. Other molecules are also useful for facilitating transfection of a nucleic acid in vivo, such as a cationic oligopeptide (e.g., International Patent Publication WO 95/21931), peptides derived from DNA binding proteins (e.g., International Patent Publication WO 96/25508), or a cationic polymer (e.g., International Patent Publication WO 95/21931).

It is also possible to introduce the vector in vivo as a naked DNA plasmid. Naked DNA vectors for gene therapy can be introduced into the desired host cells by methods known in the art; e.g., electroporation, microinjection, cell fusion, DEAE dextran, calcium phosphate precipitation, use of a gene gun, or use of a DNA vector transporter (see, e.g., Wu et al., *J. Biol. Chem.* 1992, 267:963-967; Wu and Wu, *J. Biol. Chem.* 1988, 263:14621-14624; Hartmut et al., Canadian Patent Application No. 2,012,311, filed Mar. 15, 1990; Williams et al., *Proc. Nat'l. Acad. Sci. U.S.A.* 1991, 88:2726-2730). Receptor-mediated DNA delivery approaches can also be used (Curiel et al., *Hum. Gene Ther.* 1992, 3:147-154; Wu and Wu, *J. Biol. Chem.* 1987, 262:4429-4432). U.S. Pat. Nos. 5,580,859 and 5,589,466 disclose delivery of exogenous DNA sequences, free of transfection facilitating agents, in a mammal. Recently, a relatively low voltage, high efficiency in vivo DNA transfer technique, termed electrotransfer, has been described (Mir et al., *C.P. Acad. Sci.* 1998, 321:893; WO 99/01157; WO 99/01158; WO 99/01175).

Preferably, for in viva administration, an appropriate immunosuppressive treatment is employed in conjunction with the viral vector, e.g., adenovirus vector, to avoid immuno-deactivation of the viral vector and transfected cells. For example, immunosuppressive cytokines, such as interleukin-12 (IL-12), interferon-7 (IFN-γ), or anti-CD4 antibody, can be administered to block humoral or cellular immune responses to the viral vectors (see, e.g., Wilson, *Nat. Med.* 1:887-9, 1995). In that regard, it is advantageous to employ a viral vector that is engineered to express a minimal number of antigens.

Diagnostic Methods

According to the present disclosure, mutated forms of RAF1 and SOS1 can be detected to diagnose a subject suspected of having Noonan syndrome. For example, detection of RAF1 or SOS1 mutants that encode RAF1 or SOS1 polypeptide variants, respectively, can function as a "genetic diagnostic" to verify a preliminary clinical diagnosis based on known phenotypic NS characteristics.

Accordingly, diagnostic methods may comprise, for example, detecting a mutation in a RAF1 or SOS1 nucleic acid molecule, wherein the mutation results in increased RAF1 or SOS1 polypeptide activity, respectively. In certain embodiments, mutations may affect a coding region, such as conserved region 1 (CR1), CR2, CR3, or the carboxy-terminus of RAF1. In other embodiments, mutations may affect an SOS1 coding region, such as a Pleckstrin Homology-Ras Exchanger motif (PH-Rem) linker, PH domain, or amino acids involved in associating Dbl Homology (DH) domain with the Rem domain. The mutations may be a missense mutation, preferably a missense mutation resulting in a nucleic acid substitution, or a deletion, or a combination thereof. In certain embodiments, the mutation results in one or more of the amino acid substitutions set forth in Table 1 or Table 2.

The diagnostic methods of this disclosure also encompass detecting a mutation in a RAF1 or SOS1 polypeptide, in particular a mutation that results in increased activity of the RAF1 or SOS1 polypeptide. In one embodiment, the RAF1 or SOS1 mutation is an amino acid substitution. In certain embodiments, the RAF1 mutation is in the CR1, CR2, CR3, or the carboxy-terminus domain, including domains involved in 14-3-3 protein binding. In certain related embodiments, amino acid substitutions of RAF1 are set forth in Table 1. In other embodiments, the SOS1 mutation is in a PH-Rem linker, a PH domain, or amino acids involved in associating a DH domain with a Rem domain. In further related embodiments, amino acid substitutions of SOS1 are set forth in Table 2.

In another embodiment, the diagnosis of Noonan syndrome in a subject suspected of having NS comprises assessing the level of activity or expression of RAF1 or SOS1 protein and comparing it to the level of activity or expression in a control subject, wherein an increased activity or expression of the RAF1 or SOS1 protein in the subject compared to the control subject is indicative of Noonan syndrome.

The level of expression of RAF1 or SOS1 may be assessed by determining the amount of mRNA that encodes the RAF1 or SOS1 protein, respectively, in a biological sample, or by determining the concentration of RAF1 or SOS1 protein in a biological sample. The level of RAF1 or SOS1 protein or activity may be assessed by determining the level of serine/threonine protein kinase activity or guanine nucleotide exchange activity, respectively, in a sample or subject, and the level of activity in a RAF1 or SOS1 signaling pathway may be assessed by determining the pathway signaling flux, e.g., by measuring RAF1 or SOS1 or ERK activity in a sample or subject, as described herein.

This disclosure also provides kits for performing these diagnostic methods. In one embodiment of this disclosure, a kit is provided for diagnosing Noonan syndrome in a human suspected of having NS, comprising an oligonucleotide that specifically hybridizes to a site harboring a mutation of a RAF1 or SOS1 nucleic acid molecule, or hybridizes to an adjacent site, wherein the mutation results in increased basal activity of the RAF1 or SOS1 protein. In certain embodiments, a RAF1 mutation may comprise a nucleotide substitution at nucleotide 1161, 1163, 1169, 1172, 1174, 1175, 1849, 1850, 1865, 2227, or 2230 of SEQ ID NO:1 (see Table 1), as described herein. In certain other embodiments, an SOS1 mutation may comprise a nucleotide substitution at nucleotide 322, 806, 1294, 1297, 1322, 1642, 1649, 1654, 1655, 1656, 2104, 2186, 2197, 2536, 2930, 3959 of SEQ ID NO:3 (see Table 2), as described herein. A further subject of this disclosure is a kit for diagnosing Noonan syndrome in a human suspected of having NS, comprising an antibody that specifically recognizes a variant form of a RAF1 or SOS1 polypeptide, which variants have an increased basal activity of RAF1 or SOS1 polypeptide, respectively.

As used herein, the term "diagnosis" refers to the identification of the disease at any stage of its development, and also includes the determination of a predisposition of a subject to develop the disease. In certain aspects, this disclosure permits genetic counseling of prospective parents and in utero genetic testing for Noonan syndrome. Families with one affected parent or with advanced paternal age are of particular concern. The diagnostic method of this disclosure also allows confirmation of a questionable NS diagnosis based on phenotype (appearance and symptomology). The diagnostic method of this disclosure may also be envisioned in the case of fetal abnormalities whose cause may not be obvious, or in the case of fetal loss, to evaluate viability of future pregnancies.

The term "biological sample" refers to any cell source from which a nucleic acid molecule may be obtained. Exemplary cell sources available in clinical practice include blood cells, buccal cells, cervicovaginal cells, epithelial cells from urine, fetal cells, or any cells present in tissue obtained by biopsy. Cells may also be obtained from body fluids, including without limitation blood, plasma, serum, lymph, milk, cerebrospinal fluid, saliva, sweat, urine, feces, and tissue exudates (e.g., pus) at a site of infection or inflammation. For prenatal testing, genetic material can be obtained from fetal cells, e.g., from amniotic fluid (through amniocentesis), chronic villi, blood, or any tissue of a pregnant woman. DNA is extracted using any of the numerous methods that are standard in the art. It will be understood that the particular method used to extract DNA will depend on the nature of the source. Generally, the minimum amount of DNA to be extracted for use in the present disclosure is about 25 pg (corresponding to about 5 cell equivalents of a genome size of $4 \times 10^9$ base pairs). Various methods for detecting such mutated forms of a RAF1 or SOS1 polypeptide are described herein.

The present disclosure further contemplates detecting abnormalities, i.e., mutations in a RAF1 or SOS1 nucleic acid sequence, that result in an increased basal activity of an encoded RAF1 or SOS1 polypeptide, respectively; result in a constitutively active polypeptide; provide prolonged and increased RAF1 or SOS1 polypeptide activity; or increase the level of expressed RAF1 or SOS1 polypeptide.

Mutations may include an insertion, a truncation, a deletion, a nonsense mutation, a frameshift mutation, a splice-site mutation, or a missense mutation. Such mutations can occur in the coding region of a RAF1 or SOS1 nucleic acid sequence, more particularly in any of the identified structural or functional domains, as well as in the untranslated regions, such as a promoter or enhancer region. In certain embodiments, RAF1 nucleic acid molecule mutations are nucleotide substitutions of SEQ ID NO:1 in RAF1 exon 7, exon 14, or exon 16. In other embodiments, SOS1 nucleic acid molecule mutations are nucleotide substitutions of SEQ ID NO:3 in SOS1 exon 4, exon 7, exon 11, exon 14, exon 15, or exon 17. In preferred embodiments, RAF1 or SOS1 mutations result in amino acid substitutions, such as those listed in Table 1 and Table 2, respectively.

Nucleic Acid Based Assays

According to this disclosure, mutated forms of RAF1 or SOS1 nucleic acids, i.e., in the RAF1 or SOS1 DNA or their transcripts, respectively, as well as deregulated expression, e.g., overexpression of RAF1 or SOS1 or other components of a RAF1 or SOS1 signaling pathway (e.g., ERK2) can be detected by a variety of suitable methods.

Standard methods for analyzing the nucleic acid contained in a biological sample and for diagnosing a genetic disorder can be employed, and many strategies for genotypic analysis are known to those of skill in the art.

In one embodiment, the detection of mutations in the RAF1 or SOS1 gene encompasses the use of nucleic acid sequences, such as specific oligonucleotides, to detect mutations in RAF1 or SOS1 genomic DNA or mRNA in a biological sample. Such oligonucleotides may be specifically hybridized at a site of mutation or at a region adjacent to the site of mutation present in a RAF1 or SOS1 nucleic acid molecule. One may also employ primers that permit amplification of all or part of a RAF1 or SOS1 nucleic acid molecule. Alternatively, or in combination with such techniques, oligonucleotide sequencing described herein or known to the skilled artisan can be applied to detect RAF1 or SOS1 mutations.

One skilled in the art may use hybridization probes in solution and in embodiments employing solid-phase procedures. In embodiments involving solid-phase procedures, the test nucleic acid is adsorbed or otherwise affixed to a selected matrix or surface. The fixed, single-stranded nucleic acid is then subjected to specific hybridization with selected probes.

In another embodiment, one skilled in the art may use oligonucleotide primers in an amplification technique, such as PCR or reverse-PCR ("reverse polymerase chain reaction"), to specifically amplify the target DNA or mRNA, respectively, which is potentially present in the biological sample.

In certain embodiments, the instant disclosure provides oligonucleotides, such as primers that permit amplification of SOS1 exons. Exemplary SOS1 primers include the following sequences:

```
Exon 1 (SOS1):
Forward primer:
5'- TCCACGGCTGGTACCTGTGTC -3'      (SEQ ID NO: 7)

Reverse primer:
5'- ACCGAGAGCCAGCCGTATGAG -3'      (SEQ ID NO: 8)

Exon 2 (SOS1):
Forward primer:
5'- GGTGGTCTCAAACTCCTGACC -3'      (SEQ ID NO: 9)

Reverse primer:
5'- ACTTCTGTTCCCAAGCATTCTGG -3'    (SEQ ID NO: 10)

Exon 3 (SOS1):
Forward primer:
5'- ATTATACCACATGTGAAAAGCTC -3'    (SEQ ID NO: 11)

Reverse primer:
5'- TTCTCACCACATAAATCTCTGG -3'     (SEQ ID NO: 12)

Exon 4 (SOS1):
Forward primer:
5'- AAATGTTGTTGGTAAGCACAGGC -3'    (SEQ ID NO: 13)

Reverse primer:
5'- TCCCTACTATTAGGTTACTGGAG -3'    (SEQ ID NO: 14)

Exon 5 (SOS1):
Forward primer:
5'- AACTTTATTCAGAGAACTTAGAGC -3'   (SEQ ID NO: 15)

Reverse primer:
5'- GGTCATGCAAATTTCACAACAC -3'     (SEQ ID NO: 16)
```

Exon 6 (SOS1):
Forward primer:
5'- CACTGACCTAGAGAAATGTATTTGC -3'  (SEQ ID NO: 17)

Reverse primer:
5'- TAGCTGGAAAGAAGTAAGACTCTC -3'  (SEQ ID NO: 18)

Exon 7/8 (SOS1):
Forward primer:
5'- AATTGTGCTCGCATAGTCGTGC -3'  (SEQ ID NO: 19)

Reverse primer:
5'- CTAATGTGCAGGGTACTCACAC -3'  (SEQ ID NO: 20)

Exon 9 (SOS1):
Forward primer:
5'- CTTAACACTGCTAATCTTGGTC -3'  (SEQ ID NO: 21)

Reverse primer:
5'- CTTCATTGTTTACTTGAGGAGG -3'  (SEQ ID NO: 22)

Exon 10 (SOS1):
A.
Forward primer:
5'- CACTTTCCCTTACTTACATGAGCTC -3'  (SEQ ID NO: 23)

Reverse primer:
5'- CTGTAAAGATATCAATGCTGCCA -3'  (SEQ ID NO: 24)

B.
Forward primer:
5'- GATGACACCAATGAATACAAGC -3'  (SEQ ID NO: 25)

Reverse primer:
5'- CATGCAGGAAAGAAAATCAGT -3'  (SEQ ID NO: 26)

Exon 11 (SOS1):
Forward primer:
5'- AAGTCCAAAGCCTTCTACTTGG -3'  (SEQ ID NO: 27)

Reverse primer:
5'- TGAAAAGGATCTTAGCTCAATCTC -3'  (SEQ ID NO: 28)

Exon 12 (SOS1):
Forward primer:
5'- GTTTACACTGATATGCATATCTTCAG -3'  (SEQ ID NO: 29)

Reverse primer:
5'- CTAATTTTATTGTCACCCCTCTCC -3'  (SEQ ID NO: 30)

Exon 13 (SOS1):
Forward primer:
5'- CTGATAAGATTAATTTGGTAAGAG -3'  (SEQ ID NO: 31)

Reverse primer:
5'- TATAAACATCTTACATTACTGAGC -3'  (SEQ ID NO: 32)

Exon 14 (SOS1):
Forward primer:
5'- CAAAGATACATTCAGGTGTCATCC -3'  (SEQ ID NO: 33)

Reverse primer:
5'- GTCTTATGAAAACCCTATAAGGCAG -3'  (SEQ ID NO: 34)

Exon 15 (SOS1):
Forward primer:
5'- TATAAGAGGAAAGTTCATATGAGAG -3'  (SEQ ID NO: 35)

Reverse primer:
5'- GAAATTCATAACATAGCTGACAGC -3'  (SEQ ID NO: 36)

Exon 16 (SOS1):
Forward primer:
5'- GCCTTCCTTCTATCAGTCACCC -3'  (SEQ ID NO: 37)

Reverse primer:
5'- TAGCTTAGGCTGGGACCTGTG -3'  (SEQ ID NO: 38)

Exon 17 (SOS1):
Forward primer:
5'- TGTATTTGGGCGTTTCTGTTAGCC -3'  (SEQ ID NO: 39)

Reverse primer:
5'- GATCAAACAAGTATTTTCTGCTGGC -3'  (SEQ ID NO: 40)

Exon 18 (SOS1):
Forward primer:
5'- GATGGTACAGTGTAATATACCCAC -3'  (SEQ ID NO: 41)

Reverse primer:
5'- CTTCTCCATGCTATTTCCCATCG -3'  (SEQ ID NO: 42)

Exon 19 (SOS1):
Forward primer:
5'- CCAAAATCAGCCTTACTGTTTACG -3'  (SEQ ID NO: 43)

Reverse primer:
5'- CACATATGGTAGTAATGACATCACC -3'  (SEQ ID NO: 44)

Exon 20 (SOS1):
Forward primer:
5'- TATATTAGCTGAATTTTACCAGGC -3'  (SEQ ID NO: 45)

Reverse primer:
5'- ACTTAACTACAAGTTCACACATAC -3'  (SEQ ID NO: 46)

Exon 21 (SOS1):
Forward primer:
5'- ATGAAATCAAGTAAAGCTAAAAGG -3'  (SEQ ID NO: 47)

Reverse primer:
5'- CTAAAGATAGCACAAGTGAAGG -3'  (SEQ ID NO: 48)

Exon 22 (SOS1):
Forward primer:
5'- ATTGGTTTATTGAACAGCTTTTGG -3'  (SEQ ID NO: 49)

Reverse primer:
5'- AGTGAGAACTAAACTAGACAGC -3'  (SEQ ID NO: 50)

Exon 23 (SOS1):
A.
Forward primer:
5'- ACACTTAGCATCCTGCCAATAGC -3'  (SEQ ID NO: 51)

Reverse primer:
5'- CTGTTTGGGAAGAAGGCATTGC -3'  (SEQ ID NO: 52)

B.
Forward primer:
5'- TCAAGCTCACCACTACATCTCC -3'  (SEQ ID NO: 53)

Reverse primer:
5'- GTTCTCATTTTAACTCCTCAGTGC -3'  (SEQ ID NO: 54)

In certain other embodiments, the instant disclosure provides oligonucleotides, such as primers that permit amplification of RAF1 exons. Exemplary RAF1 primers include the following sequences:

Exon 2 (RAF1):
Forward primer:
5'- TCTTTGCTGATGAATGCAGGAG -3'  (SEQ ID NO: 55)

Reverse primer:
5'- AATGACAATGAATATTTTGCCTGTC -3'  (SEQ ID NO: 56)

Exon 3 (RAF1):
Forward primer:
5'- CATCACAAGCAATACAGACTGG -3'  (SEQ ID NO: 57)

Reverse primer:
5'- AACTTTTCAAGAGAATGTCCAAGC -3'  (SEQ ID NO: 58)

Exon 4 (RAF1):
Forward primer:
5'- AACTTGCTGTGTGGCCTTGAG -3'       (SEQ ID NO: 59)

Reverse primer:
5'- TGAGAAATCTCTGTTATGCCTGG -3'     (SEQ ID NO: 60)

Exon 5 (RAF1):
Forward primer:
5'- GTACATGCTGGAAGTATGATTC -3'      (SEQ ID NO: 61)

Reverse primer:
5'- CCTGTCAGTCAAAATCTACAAC -3'      (SEQ ID NO: 62)

Exon 6 (RAF1):
Forward primer:
5'- CTGTATGTTTATTGGCAGGTCAG -3'     (SEQ ID NO: 63)

Reverse primer:
5'- CAGTATCAAGTTCCACAGAAGC -3'      (SEQ ID NO: 64)

Exon 7 (RAF1):
Forward primer:
5'- CCAGTATGAAAGCCTAAGTGC -3'       (SEQ ID NO: 65)

Reverse primer:
5'- CTGAAATAAGTATCAACCTCACC -3'     (SEQ ID NO: 66)

Exon 8/9 (RAF1):
Forward primer:
5'- ATCTTTTGTGTGTAGGAGTTGACC -3'    (SEQ ID NO: 67)

Reverse primer:
5'- TTCTTACTGAACCCTAATTGGCAG -3'    (SEQ ID NO: 68)

Exon 10 (RAF1):
Forward primer:
5'- CATGGGTTGATCCTTTGATGC -3'       (SEQ ID NO: 69)

Reverse primer:
5'- CTTGACTTCACACCAAAGCCC -3'       (SEQ ID NO: 70)

Exon 11 (RAF1):
Forward primer:
5'- CACTGTATCTTCCTCAAAACTAG -3'     (SEQ ID NO: 71)

Reverse primer:
5'- CAGTGAGTCCTAACTGCCTGC -3'       (SEQ ID NO: 72)

Exon 12 (RAF1):
Forward primer:
5'- GCTTCTCTTTGCTCAGAATGC -3'       (SEQ ID NO: 73)

Reverse primer:
5'- CTGATCCTGGTTCCAATTTAGG -3'      (SEQ ID NO: 74)

Exon 13 (RAF1):
Forward primer:
5'- GTGGCTTTACTTCTTAGCTGTAG -3'     (SEQ ID NO: 75)

Reverse primer:
5'- ACCGAGAGCCACTTGTGATAG -3'       (SEQ ID NO: 76)

Exon 14 (RAF1):
Forward primer:
5'- GACCATTCTTTTGAAACCAGAG -3'      (SEQ ID NO: 77)

Reverse primer:
5'- GCATTCCTTTTGCCCTATACC -3'       (SEQ ID NO: 78)

Exon 15 (RAF1):
Forward primer:
5'- CTAGATGTCTGTGAGGCCTGTC -3'      (SEQ ID NO: 79)

Reverse primer:
5'- CAAGTCCTAACCCTCTAGCTGC -3'      (SEQ ID NO: 80)

Exon 16 (RAF1):
Forward primer:
5'- CTAAGCAGCTAGAGGGTTAGGAC -3'     (SEQ ID NO: 81)

Reverse primer:
5'- CTCCCACCTTATATTGCCATC -3'       (SEQ ID NO: 82)

Exon 17 (RAF1):
Forward primer:
5'- GATGGCAATATAAGGTGGGAG -3'       (SEQ ID NO: 83)

Reverse primer:
5'- TCCTTAGCAGCAGCTTCTCTG -3'       (SEQ ID NO: 84)

The present disclosure also provides a method of in vitro diagnosis of NS in a human suspected of having NS, comprising the steps of:

(a) contacting a biological sample containing DNA with specific oligonucleotides for amplification of all or part of a RAF1 or SOS1 nucleic acid molecule;

(b) amplifying said DNA;

(c) detecting the amplification products;

(d) comparing the amplified products as obtained to the amplified products obtained with a normal control biological sample, and thereby detecting a possible abnormality in the RAF1 or SOS1 nucleic acid molecule.

The method of this disclosure can also be applied to the detection of an abnormality in the transcript of a RAF1 or SOS1 nucleic acid molecule, e.g., by amplifying the mRNAs contained in a biological sample, such as by RT-PCR.

Thus, another embodiment of the present disclosure is a method of in vitro diagnosis of NS in a human suspected of having NS, comprising the steps of:

(a) producing cDNA from mRNA contained in a biological sample;

(b) contacting said cDNA with specific oligonucleotides permitting the amplification of all or part of the transcript of the RAF1 or SOS1 gene, under conditions permitting a hybridization of the primers with said cDNA;

(c) amplifying said cDNA;

(d) detecting the amplification products;

(e) comparing the amplified products as obtained to the amplified products obtained with a normal control biological sample, and thereby detecting a possible abnormality in the transcript of the RAF1 or SOS1 gene.

For RNA analysis, a biological sample may be any cell source, as described herein, such as a biopsy tissue, from which RNA is isolated using standard methods well known to those of ordinary skill in the art, including guanidium thiocyanate-phenol-chloroform extraction (Chomocyznski et al., *Anal. Biochem.* 162:156, 1987). The isolated RNA is then subjected to coupled reverse transcription and amplification by polymerase chain reaction (RT-PCR), using specific oligonucleotide primers that are specific for a selected site. Conditions for primer annealing are chosen to ensure specific reverse transcription and amplification; thus, the appearance of an amplification product is diagnostic of the presence of a particular genetic variation. In another embodiment, RNA is reverse-transcribed and amplified, after which the amplified sequences are identified by, e.g., direct sequencing. In still another embodiment, RAF1 or SOS1 cDNA obtained from the respective RNAs can be cloned and sequenced to identify a mutation.

The RAF1 or SOS1 nucleic acids of this disclosure can also be used as probes, e.g., in therapeutic and diagnostic assays. For instance, the present disclosure provides a probe comprising a substantially purified oligonucleotide, which oligonucleotide comprises a region having a nucleotide sequence that is capable of hybridizing specifically to a region of a RAF1 or SOS1 nucleic acid sequence that differs from the wild-type sequence (SEQ ID NO:5 or 6, respectively), e.g., a mutant or polymorphic region. Such probes can then be used to specifically detect which mutation of a RAF1 or SOS1 nucleic acid sequence is present in a sample taken from a subject, particularly a subject suspected of having NS. A mutant or polymorphic region can be located in the promoter, exon, or intron sequences of the RAF1 or SOS1 gene.

For example, certain RAF1 or SOS1 probes of this disclosure include one or more of the nucleotide substitutions listed in Table 1 or Table 2, respectively, as well as the wild-type flanking regions (see, e.g., SEQ ID NOS:1, 3, 5 and 6). For each such probe, the complement of that probe is also included as a preferred probe of this disclosure. Particularly preferred probes of this disclosure have a number of nucleotides sufficient to allow specific hybridization to the target nucleotide sequence. Thus, probes of suitable lengths based on SEQ ID NO:1, 3, 5 or 6 and complementary to the mutant RAF1 or SOS1 sequences provided herein can be constructed and tested by the skilled artisan for an appropriate level of specificity depending on the application intended. Where the target nucleotide sequence is present in a large fragment of DNA, such as a genomic DNA fragment of several tens or hundreds of kilobases, the size of the probe may have to be longer to provide sufficiently specific hybridization, as compared to a probe which is used to detect a target sequence which is present in a shorter fragment of DNA. For example, in some diagnostic methods, a portion of a RAF1 or SOS1 nucleic acid sequence may first be amplified and thus isolated from the rest of the chromosomal DNA, and then hybridized to a probe. In such a situation, a shorter probe will likely provide sufficient specificity of hybridization. For example, a probe having a nucleotide sequence of about 10 nucleotides may be sufficient, although probes of about 15 to about 20 nucleotides are preferred.

In a preferred embodiment, the probe or primer further comprises a label attached thereto, which is capable of being detected. The label can, for example, be selected from radioisotopes, fluorescent compounds, enzymes, enzyme co-factors, and the like.

In another preferred embodiment of this disclosure, the isolated nucleic acid, which is used, e.g., as a probe or a primer, is modified to be more stable. Exemplary nucleic acid molecules that are modified include phosphoramidate, phosphothioate and methylphosphonate analogs of DNA (see also U.S. Pat. Nos. 5,176,996; 5,264,564; and 5,256,775).

In yet another embodiment, one may use HPLC or denaturing HPLC (DHPLC) techniques to analyze the RAF1 or SOS1 nucleic acids. DHPLC was developed when observing that, when HPLC analyses are carried out at a partially denaturing temperature, i.e., a temperature sufficient to denature a heteroduplex at the site of base pair mismatch, homoduplexes can be separated from heteroduplexes having the same base pair length (Hayward-Lester et al., Genome Research 5:494, 1995; Underhill et al., Proc. Nat'l. Acad. Sci. USA 93:193, 1996; Doris et al., DHPLC Workshop, 1997, Stanford University). Thus, the use of DHPLC was applied to mutation detection (Underhill et al., Genome Research 7:996, 1997; Liu et al., Nucleic Acid Res. 26; 1396, 1998). DHPLC can separate heteroduplexes that differ by as little as one base pair. "Matched Ion Polynucleotide Chromatography" (MIPC), or Denaturing "Matched Ion Polynucleotide Chromatography" (DMIPC) as described in U.S. Pat. Nos. 6,287,822 or 6,024,878, are separation methods that can also be useful in connection with the present disclosure.

Alternatively, one can use the DGGE method (Denaturing Gradient Gel Electrophoresis), or the SSCP method (Single Strand Conformation Polymorphism) for detecting an abnormality in a RAF1 or SOS1 nucleic acid molecule. DGGE is a method for resolving two DNA fragments of identical length on the basis of sequence differences as small as a single base pair change, using electrophoresis through a gel containing varying concentrations of denaturant (Guldberg et al., Nuc. Acids Res. 1994, 22:880). SSCP is a method for detecting sequence differences between two DNAs, comprising hybridization of the two species with subsequent mismatch detection by gel electrophoresis (Ravnik-Glavac et al., Hum. Mol. Genet. 3:801, 1994). "HOT cleavage", a method for detecting sequence differences between two DNAs, comprising hybridization of the two species with subsequent mismatch detection by chemical cleavage (Cotton, et al., Proc. Nat'l. Acad. Sci. USA 85:4397, 1988), can also be used. Such methods are preferably followed by direct sequencing. Advantageously, the RT-PCR method may be used for detecting abnormalities in a RAF1 or SOS1 transcript, as it allows one to visualize the consequences of a splicing mutation such as exon skipping or aberrant splicing due to the activation of a cryptic site. In certain embodiments, this method is followed by direct sequencing as well.

More recently developed techniques using microarrays, preferably microarray techniques allowing for high-throughput screening, can also be advantageously implemented for detecting an abnormality in a RAF1 or SOS1 nucleic acid molecule or for assaying expression of a RAF1 or SOS1 nucleic acid molecule or the gene of another component in the RAF1 or SOS1 pathway resulting in increased signaling, as described herein. Microarrays may be designed so that the same set of identical oligonucleotides is attached to at least two selected discrete regions of the array, so that one can easily compare a normal sample, contacted with one of the selected regions of the array, against a test sample, contacted with another of the selected regions. These arrays avoid the mixture of normal sample and test sample, using microfluidic conduits. Useful microarray techniques include those developed by Nanogen, Inc (San Diego, Calif.) and those developed by Affymetrix. However, all types of microarrays, also called "gene chips" or "DNA chips", may be adapted for the identification of mutations. Such microarrays are well known in the art (see, for example, the following: U.S. Pat. Nos. 6,045,996; 6,040,138; 6,027,880; 6,020,135; 5,968,740; 5,959,098; 5,945,334; 5,885,837; 5,874,219; 5,861,242; 5,843,655; 5,837,832; 5,677,195 and 5,593,839).

The solid support on which oligonucleotides are attached may be made from glass, silicon, plastic (e.g., polypropylene, nylon), polyacrylamide, nitrocellulose, or other materials. One method for attaching the nucleic acids to a surface is by printing on glass plates, as is described generally by Schena et al., Science 1995, 270:467-470. This method is especially useful for preparing microarrays of cDNA. See also DeRisi et al., Nature Genetics 14:457-460, 1996; Shalon et al., Genome Res. 1996, 6:639-645; and Schena et al., Proc. Natl. Acad. Sci. USA 1995, 93:10539-11286. Another method of making microarrays is by use of an inkjet printing process to bind genes or oligonucleotides directly on a solid phase, as described, e.g., in U.S. Pat. No. 5,965,352.

Other methods for making microarrays, e.g., by masking (Maskos and Southern, Nuc. Acids Res. 1992, 20:1679-1684), may also be used. In principal, any type of array, for example, dot blots on a nylon hybridization membrane (see Sambrook et al., Molecular Cloning A Laboratory Manual (2nd Ed.), Vol. 1-3, Cold Spring Harbor Laboratory, Cold Spring Harbor, N.Y., 1989) could be used, although, as will be recognized by those of skill in the art, very small arrays will be preferred because hybridization volumes will be smaller. For these assays nucleic acid hybridization and wash conditions are chosen so that the attached oligonucleotides "specifically bind" or "specifically hybridize" to at least a portion of a RAF1 or SOS1 nucleic acid molecule present in a target sample, i.e., the probe hybridizes, duplexes or binds to the RAF1 or SOS1 locus with a complementary nucleic acid sequence but does not hybridize to a site with a non-complementary nucleic acid sequence. As used herein, one polynucleotide sequence is considered complementary to another when, if the shorter of the polynucleotides is less than or equal to 25 bases, there are no mismatches using standard base-pairing rules or, if the shorter of the polynucleotides is longer than 25 bases, there is no more than a 5% mismatch. Preferably, the polynucleotides are perfectly complementary (no mismatches). It can easily be demonstrated that specific hybridization conditions result in specific hybridization by carrying out a hybridization assay including negative controls (see, e.g., Shalon et al., supra, and Chee et al., *Science* 274: 610-4, 1996).

A variety of methods are available for detection and analysis of a hybridization event. Depending on the reporter group (fluorophore, enzyme, radioisotope, etc.) used to label a DNA probe, detection and analysis are carried out fluorimetrically, calorimetrically or by autoradiography. By observing and measuring emitted radiation, such as fluorescent radiation or a particle emission, information may be obtained about hybridization events.

When fluorescently labeled probes are used, the fluorescence emissions at each site of transcript array can, preferably be detected by scanning confocal laser microscopy. In one embodiment, a separate scan, using the appropriate excitation line, is carried out for each of the two fluorophores used. Alternatively, a laser can be used that allows simultaneous specimen illumination at wavelengths specific to the two fluorophores and emissions from the two fluorophores can be analyzed simultaneously (see Shalon et al., *Genome Res.* 6:639-695, 1996).

Protein Based Assays

As an alternative to analyzing RAF1 or SOS1 nucleic acids, one can evaluate RAF1 or SOS1 on the basis of mutations in the polypeptide or on the basis of dysregulated production, e.g., overproduction of the protein. In addition, RAF1 or SOS1 activity and/or ERK kinase activity can be evaluated to determine increased activity of a RAF1 or SOS1 signaling pathway such as the RAS-MAPK pathway.

In preferred embodiments, RAF1 or SOS1 or ERK2 are detected by immunoassay. For example, Western blotting permits detection of a specific variant, or the presence or absence of RAF1 or SOS1 or ERK2. In particular, an immunoassay can detect a specific (wild-type or mutant) amino acid sequence in a RAF1 or SOS1 protein. Other immunoassay formats can also be used in place of Western blotting, as described below for the production of antibodies. One of these is ELISA assay.

In ELISA assays, an antibody against RAF1 or SOS1, an epitopic fragment of RAF1 or SOS1, or ERK2, is immobilized onto a selected surface, for example, a surface capable of binding proteins such as the wells of a polystyrene microtiter plate. After washing to remove incompletely adsorbed polypeptides, a nonspecific protein such as a solution of bovine serum albumin (BSA) may be bound to the selected surface. This allows for blocking of nonspecific adsorption sites on the immobilizing surface and thus reduces the background caused by nonspecific bindings of antisera onto the surface. The immobilizing surface is then contacted with a sample, to be tested in a manner conductive to immune complex (antigen/antibody) formation. This may include diluting the sample with diluents, such as solutions of BSA, bovine gamma globulin (BGG) and/or phosphate buffered saline (PBS)/Tween. The sample is then allowed to incubate for from 2 to 4 hours, at temperatures between about 25° to 37° C. Following incubation, the sample-contacted surface is washed to remove non-immunocomplexed material. The washing procedure may include washing with a solution, such as PBS/Tween or borate buffer. Following formation of specific immunocomplexes between the test sample and the bound antibody, and subsequent washing, the occurrence, and an even amount of immunocomplex formation may be determined by subjecting the immunocomplex to a second antibody against RAF1 or SOS1 or ERK2, which recognizes a different epitope on the proteins. To provide a method of detection, a second antibody may have an associated activity such as an enzymatic activity that will generate, for example, a color development upon incubating with an appropriate chromogenic substrate. Quantification may then be achieved by measuring the degree of color generation using, for example, a visible spectra spectrophotometer.

Typically the detection antibody is conjugated to an enzyme such as peroxidase and the protein is detected by the addition of a soluble chromophore peroxidase substrate such as tetramethylbenzidine followed by 1 M sulfuric acid. The test protein concentration is determined by comparison with standard curves. These protocols are detailed in Current Protocols in Molecular Biology, V. 2 Ch. 11 and Antibodies, a Laboratory Manual, Ed Harlow, David Lane, Cold Spring Harbor Laboratory (1988) pp 579-593.

Alternatively, a biochemical assay can be used to detect expression, or accumulation of RAF1 or SOS1 or ERK2, e.g., by detecting the presence or absence of a protein band in samples analyzed by polyacrylamide gel electrophoresis; by the presence or absence of a chromatographic peak in samples analyzed by any of the various methods of high performance liquid chromatography, including reverse phase, ion exchange, and gel permeation; by the presence or absence of RAF1 or SOS1 or ERK2 in analytical capillary electrophoresis chromatography, or any other quantitative or qualitative biochemical technique known in the art.

The immunoassays discussed above involve using antibodies directed against a RAF1 or SOS1 protein or fragments thereof. The production of such antibodies is described below. Production of anti-ERK2 antibodies, or other components of a RAF1 or SOS1 pathway, can be prepared in a similar manner.

Anti-RAF1 and Anti-SOS1 Antibodies

In certain embodiment, antibodies specific for RAF1 or SOS1 are provided, which include polyclonal, monoclonal, chimeric, humanized, human, single chain, Fab fragments, Fab expression library, and the like.

Various procedures known in the art may be used for the production of polyclonal antibodies to a RAF1 or SOS1 polypeptide, or derivative or analog thereof. For the production of a polyclonal antibody, various host animals can be immunized by injection with the antigenic polypeptide, including rabbits, mice, rats, sheep, goats, etc.

Any technique that provides for the production of antibody molecules by continuous cell lines in culture may be used for the preparation of monoclonal antibodies specific for a RAF1 or SOS1 polypeptide. These methods include the hybridoma technique originally developed by Kohler and Milstein (*Nature* 256:495-7, 1975), as well as the trioma technique, the human B-cell hybridoma technique (Kozbor et al., *Immunology Today* 4:72, 1983; Cote et al., *Proc. Nat'l. Acad. Sci. U.S.A.* 80:2026-2030, 1983), and the EBV-hybridoma technique to produce human monoclonal antibodies (Cole et al., in Monoclonal Antibodies and Cancer Therapy, Alan R. Liss, Inc., pp. 77-96, 1985). In an additional embodiment of this disclosure, monoclonal antibodies can be produced in germ-free animals (International Patent Publication No. WO 89/12690, published 28 Dec., 1989).

According to this disclosure, techniques described for the production of single chain antibodies (U.S. Pat. Nos. 5,476, 786 and 5,132,405 to Huston; U.S. Pat. No. 4,946,778) can be adapted to produce a RAF1 or SOS1 polypeptide-specific single chain antibodies. Indeed, these genes can be delivered for expression in vivo. An additional embodiment of this disclosure utilizes the techniques described for the construction of Fab expression libraries (Huse et al., *Science* 246: 1275-1281, 1989) to allow rapid and easy identification of monoclonal Fab fragments with the desired specificity for a RAF1 or SOS1 polypeptide, or its derivatives or analogs thereof.

Antibody fragments which contain the idiotype of the antibody molecule can be generated by known techniques. For example, such fragments include but are not limited to: the F(ab')$_2$ fragment which can be produced by pepsin digestion of the antibody molecule; the Fab' fragments which can be generated by reducing the disulfide bridges of the F(ab')$_2$ fragment, and the Fab fragments which can be generated by treating the antibody molecule with papain and a reducing agent.

In the production of antibodies, screening for the desired antibody can be accomplished by techniques known in the art, e.g., radioimmunoassay, ELISA (enzyme-linked immunosorbant assay), "sandwich" immunoassays, immunoradiometric assays, gel diffusion precipitin reactions, immunodiffusion assays, in situ immunoassays (using colloidal gold, enzyme or radioisotope labels, for example), western blots, precipitation reactions, agglutination assays (e.g., gel agglutination assays, hemagglutination assays), complement fixation assays, immunofluorescence assays, protein A assays, and immunoelectrophoresis assays, etc. In one embodiment, antibody binding is detected by detecting a label on the primary antibody. In another embodiment, the primary antibody is detected by detecting binding of a secondary antibody or reagent to the primary antibody. In a further embodiment, the secondary antibody is labeled. Many means are known in the art for detecting binding in an immunoassay and are within the scope of the present disclosure.

RAF1, SOS1 and ERK2 Activity Assays

As described herein, increased activity or level of a RAF1 or SOS1 polypeptide or other components in a RAF1 or SOS1 signaling pathway is indicative of NS. In one embodiment one may assess the activity of a RAF1 or SOS1 polypeptide in a human subject or biological sample taken from the subject suspected of having NS and compare with a control. An increased activity of a RAF1 or SOS1 polypeptide in the target subject or biological sample compared with the control is indicative of NS in the target subject.

The activity of a RAF1 or SOS1 polypeptide may be indirectly assayed by evaluating the level of expression, accumulation or activity of down-stream effectors, as described herein. In certain embodiments, down-stream effectors are MAP kinases, such as ERK1 or ERK2. The nucleic acid-based assays or protein-based assays as described herein may be readily adapted for such a purpose. Since RAF1 is a kinase and SOS1 has a Ras binding domain, the basal activity of RAF1 or SOS1 polypeptide in a subject suspected of having NS may be easily determined by assessing kinase activity of RAF1 variant polypeptides and by assessing Ras activation by SOS1 variant polypeptides.

In one embodiment, the level of phosphorylation of a peptide or protein is assessed by utilizing a binding partner, which should preferably be highly specific for the phospho-epitope on the target protein. It is preferred that the binding partner is an antibody. The antibody is preferably generated against a unique epitope of the substrate. In an alternative embodiment, the binding partner should be specific for the phosphorylated form of the target protein. The detection procedure used to assess the phosphorylation state of the protein may for instance employ an antibody or a peptide that recognizes and binds to phosphorylated serines, threonines or tyrosines. The detection antibody is preferably a polyclonal antibody, to maximize the signal, but may also be specific monoclonal antibodies which have been optimized for signal generation. An exemplary kinase and Ras activation assays are provided in the Examples.

ERK activity, in particular ERK2 activity, can be assessed by measuring kinase activity, i.e., transfer of phosphate from ATP to a second substrate. Many such assays are known in the art, and an exemplary ERK2 assay is provided in Example 2. Alternatively, immunoassays may be replaced by the detection of radiolabeled phosphate according to a standard technique. This involves incubating cells with the test substances and radiolabeled phosphate, lysing the cells, separating cellular protein components of the lysate using as SDS-polyacrylamide gel (SDS-PAGE) technique, in either one or two dimensions, and detecting the presence of phosphorylated proteins by exposing X-ray film.

The phosphorylation of a protein may also be conveniently detected by migration on a gel subject to electrophoresis, followed by western blotting. Phosphorylation is detected by a shift of the molecular weight of the protein occurs, a phosphorylated protein being heavier than the corresponding non-phosphorylated form.

Diagnostic Kits

The present disclosure further provides kits for the determination of the sequence within a RAF1 or SOS1 gene in an individual. In some embodiments, the kits comprise agent(s) for determining the RAF1 or SOS1 nucleic acid sequence at the variant positions, and may optionally include data for analysis of mutations. The means for sequence determination may comprise suitable nucleic acid-based and immunological reagents. In certain embodiments, the kits also comprise suitable buffers, control reagents where appropriate, and directions for determining the sequence at a variant position.

(a) Nucleic Acid Based Diagnostic Kits

This disclosure provides nucleic acid-based methods for detecting genetic variations of RAF1 or SOS1 in a biological sample. The sequence at particular positions in a RAF1 or SOS1 gene is determined by using any suitable means known in the art, including one or more of hybridization with specific probes for PCR amplification (e.g., primer pairs selected from SEQ ID NOS:3-32), restriction fragmentation, direct sequencing, SSCP, and other techniques known in the art. The present disclosure also provides kits suitable for nucleic acid-based diagnostic applications. In one embodiment, diagnostic kits include the following components:

(a) a probe nucleic acid molecule, wherein the probe nucleic acid molecule may be pre-labeled; alternatively, the probe nucleic acid molecule may be unlabeled and the ingredients for labeling may be included in the kit in separate containers; and (b) hybridization reagents, wherein the kit contains other suitably packaged reagents and materials needed for the particular hybridization protocol, including solid-phase matrices, if applicable, and standards.

In certain embodiments, the probe nucleic acid molecule is DNA.

In another embodiment, diagnostic kits include:

(a) Sequence determination primers: Sequencing primers may be pre-labeled or may contain an affinity purification or attachment moiety; and (b) Sequence determination reagents: The kit may also contain other suitably packaged reagents and materials needed for the particular sequencing protocol.

In one embodiment, the kit comprises a panel of sequencing primers, whose sequences correspond to sequences adjacent to variant positions on a RAF1 or SOS1 nucleic acid molecule.

(b) Antibody-Based Diagnostic Kits

This disclosure also provides antibody-based methods for detecting mutant (or wild type) RAF1 or SOS1 polypeptides in a biological sample. The methods comprise the steps of: (i) contacting a sample with one or more antibody, wherein each antibody is specific for a mutant (or wild type) RAF1 or SOS1 polypeptide under conditions in which a stable antigen-antibody complex can form; and (ii) detecting any antigen-antibody complex formed in step (i) using any suitable means known in the art, wherein the detection of a complex indicates the presence of a mutant (or wild type) RAF1 or SOS1 polypeptide.

Generally, immunoassays use either a labeled antibody or a labeled antigenic component (e.g., that competes with the antigen in the sample for binding to the antibody). Suitable labels include enzyme-based, fluorescent, chemiluminescent, radioactive, dye molecules, or the like. Assays that amplify the signals from the probe are also known, such as, for example, those that utilize biotin and avidin, and enzyme-labeled immunoassays, such as ELISA assays.

The present disclosure also provides kits suitable for antibody-based diagnostic applications. In certain embodiments, diagnostic kits include one or more of the following components: (i) RAF1 or SOS1 polypeptide-specific antibodies, wherein the antibodies may be pre-labeled; alternatively, the antibody may be unlabeled and the ingredients for labeling may be included in the kit in separate containers, or a secondary, labeled antibody is provided; and (ii) reaction components, wherein the kit optionally contains other suitably packaged reagents and materials needed for the particular immunoassay protocol, including solid-phase matrices, if applicable, and standards.

The kits referred to above may include instructions for conducting the test. Furthermore, in preferred embodiments, the diagnostic kits are adaptable to high-throughput or automated operation.

Therapeutics

The present disclosure further provides a method for the treatment of NS, which method comprises modulating activity of a RAF1 or SOS1 polypeptide in a subject or patient having a RAF1 or SOS1 mutation. In another embodiments, the instant disclosure provides a method in which a subject suspected of having NS is diagnosed with NS by detecting a mutation in a RAF1 or SOS1 nucleic acid molecule, wherein the RAF1 or SOS1 nucleic acid molecule encodes a RAF1 or SOS1 polypeptide of SEQ ID NO:2 or 4, respectively, having an amino acid substitution and reduced autoinhibition as described herein, and the NS is treated by administering an effective amount of an agent that modulates activity of the variant RAF1 or SOS1 polypeptide. In any of these embodiments, the method comprises administering to a patient in need of such treatment an effective amount of an agent that modulates RAF1 or SOS1 polypeptide expression or activity, with a pharmaceutically acceptable diluent or carrier. For example, the therapeutic agent may be a RAF1 or SOS1 antisense or small interfering nucleic acid molecule, or an anti-RAF1 or anti-SOS1 intracellular inhibitory antibody.

In another aspect, the present disclosure further provides a method for the treatment of hypertrophic cardiomyopathy (HCM) associated with NS. In certain embodiments, a subject having HCM associated with NS is treated with an agent that modulates or alters the activity of a RAF1 polypeptide in a subject having a mutation in a RAF1 nucleic acid molecule of SEQ ID NO:1, wherein the mutated RAF1 nucleic acid molecule encodes a RAF1 variant polypeptide having an amino acid substitution and reduced autoinhibition, as described herein. In particular embodiments, the instant disclosure provides a method in which a subject, who has HCM and is suspected of having NS, is diagnosed with NS by detecting a mutation in a RAF1 nucleic acid molecule, wherein the RAF1 nucleic acid molecule encodes a RAF1 polypeptide of SEQ ID NO:2 having an amino acid substitution and reduced autoinhibition as described herein, and the NS-associated HCM is treated by administering an effective amount of an agent that modulates activity of the variant RAF1 polypeptide. In any of these embodiments, an agent that modulates RAF1 polypeptide activity in a pharmaceutically acceptable diluent or carrier is administered to the subject in need thereof. For example, the therapeutic agent may be a RAF1 antisense or small interfering nucleic acid molecule or an anti-RAF1 intracellular inhibitory antibody.

A "subject" or "patient" is a human or an animal likely to develop NS or suspected of having NS, more particularly a mammal, preferably a human or a primate as described herein in connection with diagnostic applications. Prenatal treatment is also envisioned. In a preferred embodiment, the subject is human.

The term "treatment" means to therapeutically intervene in the development of a disease in a subject showing a symptom of this disease. The term "treatment" also encompasses prevention, which means to prophylactically interfere with a pathological mechanism that results in a disease.

The term "modulating RAF1 or SOS1 activity" in a subject means modifying it so that it is rendered as close as possible to the normal RAF1 or SOS1 activity of a control subject. In certain embodiments, modulating RAF1 or SOS1 activity encompasses inhibiting or blocking the activity of a RAF1 or SOS1 variant polypeptide in an NS patient. Preferred modulators block any of the functional domains of a variant RAF1 or SOS1 polypeptide as described herein. As used herein, modulating RAF1 or SOS1 activity also encompasses increasing or restoring autoinhibition activity.

The modulation activity may be achieved by various methods, as described herein. In one embodiment, a modulatory agent may be a substance that is known or has been identified to modulate, especially inhibit, whether fully or partially, variant RAF1 or SOS1 polypeptides with gain-of function activity. For example, this modulatory agent may be a candidate drug as identified by a screening method analyzing Ras-activation or Mek kinase activity. In other embodiments, a modulatory agent may also be an inhibitory antibody directed against variant RAF1 or SOS1 polypeptides with gain-of function activity. In a further embodiment, a modulatory agent may be an antisense or small interfering nucleic acid. A substance that modulates or inhibits RAF1 or SOS1 activity is advantageously formulated in a pharmaceutical composition, with a pharmaceutically acceptable carrier or diluent. This substance may then be called an active ingredient or therapeutic agent against NS. The pharmaceutical compositions may also include other biologically active compounds.

The term "therapeutically effective amount" as used herein means an amount or dose sufficient to modulate, e.g., decrease the level of variant RAF1 or SOS1 activity e.g., by about 10 percent, preferably by about 50 percent, and more preferably by about 90 percent. Preferably, a therapeutically effective amount can ameliorate or present a clinically significant deficit in the activity, function, and response of the subject. Alternatively, a therapeutically effective amount is sufficient to cause an improvement in a clinically identifiable condition in a subject. The concentration or amount of an active ingredient depends on the desired dosage and administration regimen, as discussed herein. Suitable dose ranges may include from about 0.01 mg/kg to about 100 mg/kg of body weight per day.

The phrase "pharmaceutically acceptable" refers to molecular entities and compositions that are physiologically tolerable and do not typically produce an allergic or similar untoward reaction, such as gastric upset, dizziness and the like, when administered to a human. Preferably, as used herein, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant, excipient, or vehicle with which the compound is administered. Such pharmaceutical carriers can be sterile liquids, such as water and oils, including those of petroleum, animal, vegetable or synthetic origin, such as peanut oil, soybean oil, mineral oil, sesame oil and the like. Water or aqueous solution saline solutions and aqueous dextrose and glycerol solutions are preferably employed as carriers, particularly for injectable solutions. Suitable pharmaceutical carriers are described in "Remington's Pharmaceutical Sciences" by E. W. Martin.

A composition comprising "A" (where "A" is a single protein, DNA molecule, vector, recombinant host cell, etc.) is substantially free of "B" (where "B" comprises one or more contaminating proteins, DNA molecules, vectors, etc.) when at least about 75% by weight of the proteins, DNA, vectors (depending on the category of species to which A and B belong) in the composition is "A". Preferably, "A" comprises at least about 90% by weight of the A+B species in the composition, most preferably at least about 99% by weight. It is also preferred that a composition, which is substantially free of contamination, contain only a single molecular weight species having the activity or characteristic of the species of interest.

According to this disclosure, the pharmaceutical composition of this disclosure can be introduced parenterally, transmucosally, e.g., orally (per os), nasally, or rectally, or transdermally. Parental routes include intravenous, intra-arteriole, intra-muscular, intradermal, subcutaneous, intraperitoneal, intraventricular, and intracranial administration. Targeting heart, e.g. by direct administration to heart muscle or cavities, may be advantageous.

The pharmaceutical compositions may be added to a retained physiological fluid such as blood or synovial fluid.

In another embodiment, the active ingredient can be delivered in a vesicle, in particular a liposome (see Langer, Science 249:1527-1533 (1990); Treat et al., in Liposomes in the Therapy of Infectious Disease and Cancer, Lopez-Berestein and Fidler (eds.), Liss: New York, pp. 353-365 (1989); Lopez-Berestein, ibid., pp. 317-327; see generally ibid.).

In yet another embodiment, the therapeutic compound can be delivered in a controlled release system. For example, a polypeptide may be administered using intravenous infusion with a continuous pump, in a polymer matrix such as polylactic/glutamic acid (PLGA), a pellet containing a mixture of cholesterol and the active ingredient (SilasticR™; Dow Corning, Midland, Mich.; see U.S. Pat. No. 5,554,601) implanted subcutaneously, an implantable osmotic pump, a transdermal patch, liposomes, or other modes of administration.

Screening Methods

A "test substance" is a chemically defined compound or mixture of compounds (as in the case of a natural extract or tissue culture supernatant), whose ability to modulate RAF1 or SOS1 activity may be defined by various assays. A "test substance" is also referred to as a "candidate drug" in the present description.

Test substances may be screened from large libraries of synthetic or natural compounds. Numerous means are currently used for random and directed synthesis of saccharide, peptide, and nucleic acid based compounds. Synthetic compound libraries are commercially available from Maybridge Chemical Co. (Trevillet, Cornwall, UK), Comgenex (Princeton, N.J.), Brandon Associates (Merrimack, N.H.), and Microsource (New Milford, Conn.). A rare chemical library is available from Aldrich (Milwaukee, Wis.). Alternatively, libraries of natural compounds in the form of bacterial, fungal, plant and animal extracts are available from, e.g., Pan Laboratories (Bothell, Wash.) or MycoSearch (NC), or are readily producible. Additionally, natural and synthetically produced libraries and compounds are readily modified through conventional chemical, physical, and biochemical means (Blondelle et al., TIBTech 1996, 14:60).

A modulatory effect may be determined by an in vitro method using a recombinant RAF1- or SOS1-reporter gene promoter activity system. Reporter genes for use in this disclosure encode detectable proteins, include, but are by no means limited to, chloramphenicol transferase (CAT), β-galactosidase (β-gal), luciferase, green fluorescent protein (GFP) and derivatives thereof, yellow fluorescent protein and derivatives thereof, alkaline phosphatase, other enzymes that can be adapted to produce a detectable product, and other gene products that can be detected, e.g., immunologically (by immunoassay).

A screen according to this disclosure involves detecting expression of the reporter gene by the host cell when contacted with a test substance. If there is no change in expression of the reporter gene, the test substance is not an effective modulator. If reporter gene expression is modified, in particular reduced or eliminated, the test substance has modulated, e.g., inhibited, RAF1- or SOS1-mediated gene expression, and is thus a candidate for development as an NS therapeutic.

The reporter gene assay system described here may be used in a high-throughput primary screen for antagonists, or it may be used as a secondary functional screen for candidate compounds identified by a different primary screen, e.g., a binding assay screen that identifies compounds that modulate RAF1 or SOS1 transcription activity.

Potential drugs may be identified by screening in high-throughput assays, including without limitation cell-based or cell-free assays. It will be appreciated by those skilled in the art that different types of assays can be used to detect different types of agents. Several methods of automated assays have been developed in recent years so as to permit screening of tens of thousands of compounds in a short period of time (see, e.g., U.S. Pat. Nos. 5,585,277, 5,679,582, and 6,020,141). Such high-throughput screening methods are particularly preferred. Alternatively, simple reporter-gene based cell assays such as the one described here are also highly desirable.

Intact cells or whole animals expressing a gene encoding RAF1 or SOS1 can be used in screening methods to identify candidate drugs.

In one series of embodiments, a permanent cell line is established. Alternatively, cells are transiently programmed to express a RAF1 or SOS1 gene by introduction of appropriate DNA or mRNA.

Identification of candidate substances can be achieved using any suitable assay, including without limitation (i) assays that measure selective binding of test compounds to RAF1 or SOS1 (ii) assays that measure the ability of a test substance to modify (i.e., inhibit) a measurable activity or function of RAF1 or SOS1 and (iii) assays that measure the ability of a substance to modify (i.e., inhibit) the transcriptional activity of sequences derived from the promoter (i.e., regulatory) regions of a RAF1 or SOS1 gene.

Selected agents may be modified to enhance efficacy, stability, pharmaceutical compatibility, and the like. Structural identification of an agent may be used to identify, generate, or screen additional agents. For example, where peptide agents are identified, they may be modified in a variety of ways, e.g. to enhance their proteolytic stability.

Inhibitory Antibodies

The modulatory substance may also be an antibody that is directed against RAF1 or SOS1. Antibodies that block the activity of RAF1 or SOS1 may be produced and selected according to any standard method well-known by one skilled in the art, such as those described above in the context of diagnostic applications.

Intracellular antibodies (sometime referred to as "intrabodies") have been used to regulate the activity of intracellular proteins in a number of systems (see, Marasco, Gene Ther. 1997, 4:11; Chen et al., Hum. Gene Ther. 1994, 5:595), e.g., viral infections (Marasco et al., Hum. Gene Ther. 1998, 9:1627) and other infectious diseases (Rondon et al., Annu. Rev. Microbiol. 1997, 51:257), and oncogenes, such as p21 (Cardinale et al., FEBS Lett. 1998, 439:197-202; Cochet et al., Cancer Res. 1998, 58:1170-6), myb (Kasono et al., Biochem Biophys Res Commun. 1998, 251:124-30), erbB-2 (Graus-Porta et al., Mol Cell Biol. 1995, 15:1182-91), etc. This technology can be adapted to inhibit RAF1 or SOS1 activity by expression of an anti-RAF1 or anti-SOS1 intracellular antibody.

Antisense Therapy

In another embodiment, vectors comprising a sequence encoding an antisense nucleic acid according to this disclosure may be administered by any known methods, such as the methods for gene therapy available in the art. Exemplary methods are described below. For general reviews of the methods of gene therapy, see, Goldspiel et al., Clinical Pharmacy 1993, 12:488-505; Wu and Wu, Biotherapy 1991, 3:87-95; Tolstoshev, Ann. Rev. Pharmacol. Toxicol. 1993, 32:573-596; Mulligan, Science 1993, 260:926-932; and Morgan and Anderson, Ann. Rev. Biochem. 1993, 62:191-217; May, TIBTECH 1993, 11:155-215. Methods commonly known in the art of recombinant DNA technology that can be used are described in Ausubel et al., (eds.), 1993, Current Protocols in Molecular Biology, John Wiley & Sons, NY; Kriegler, 1990, Gene Transfer and Expression, A Laboratory Manual, Stockton Press, NY; and in Chapters 12 and 13, Dracopoli et al., (eds.), 1994, Current Protocols in Human Genetics, John Wiley & Sons, NY.

In one embodiment, a vector is used in which the coding sequences and any other desired sequences are flanked by regions that promote homologous recombination at a desired site in the genome, thus providing for expression of the construct from a nucleic acid molecule that has integrated into the genome (Koller and Smithies, *Proc. Nat'l. Acad. Sci. USA* 86:8932-35, 1989; Zijlstra et al., *Nature* 342:435-38, 1989).

Delivery of the vector into a patient may be either direct, in which case the patient is directly exposed to the vector or a delivery complex, or indirect, in which case, cells are first transformed with the vector in vitro, then transplanted into the patient. These two approaches are known, respectively, as in vivo and ex vivo gene therapy.

In a specific embodiment, the vector is directly administered in vivo, where it enters the cells of the organism and mediates expression of the construct. This can be accomplished by any of numerous methods known in the art and discussed above, e.g., by constructing it as part of an appropriate expression vector and administering it so that it becomes intracellular, e.g., by infection using a defective or attenuated retroviral or other viral vector (see, U.S. Pat. No. 4,980,286), or by direct injection of naked DNA, or by use of microparticle bombardment (e.g., a gene gun; Biolistic, Dupont); or coating with lipids or cell-surface receptors or transfecting agents, encapsulation in biopolymers (e.g., poly-∃-1-64-N-acetylglucosamine polysaccharide; see, U.S. Pat. No. 5,635,493), encapsulation in liposomes, microparticles, or microcapsules; by administering it in linkage to a peptide or other ligand known to enter the nucleus; or by administering it in linkage to a ligand subject to receptor-mediated endocytosis (see, e.g., Wu and Wu, *J. Biol. Chem.* 62:4429-32, 1987), etc. In another embodiment, a nucleic acid-ligand complex can be formed in which the ligand comprises a fusogenic viral peptide to disrupt endosomes, allowing the nucleic acid to avoid lysosomal degradation, or cationic 12-mer peptides, e.g., derived from antennapedia, that can be used to transfer therapeutic DNA into cells (Mi et al., *Mol. Therapy.* 2:339-47, 2000). In yet another embodiment, the nucleic acid can be targeted in vivo for cell specific uptake and expression, by targeting a specific receptor (see, e.g., PCT Publication Nos. WO 92/06180, WO 92/22635, WO 92/20316 and WO 93/14188).

Examples of practicing this disclosure are provided, and are understood to be exemplary only, and do not limit the scope of this disclosure or the appended claims. A person of ordinary skill in the art will appreciate that this disclosure can be practiced in many forms according to the claims and disclosures herein.

EXAMPLES

Example 1

Detection of Mutations in RAF1 and SOS1

High-Throughput Resequencing. A cohort of 96 human subjects with NS was assembled from whom genomic DNAs were obtained from peripheral blood leukocytes. Nearly all subjects were Caucasian and of European ancestry, with the majority being Italian. The subjects did not harbor a PTPN11 or a KRAS mutation based on scanning of the coding exons with DHPLC (Wave 2100 System, Transgenomic) and/or bidirectional DNA sequencing as previously described (Carta et al., *Am. J. Hum. Genet.* 79:129-135, 2006; Tartaglia et al., *Am. J. Hum. Genet.* 70:1555-63, 2002). For sporadic cases, which represented the vast majority of the subjects, we obtained both parental DNAs whenever possible. All non-anonymous samples were collected under Institutional Review Board-approved protocols and with informed consent.

We chose a cohort of this size with the assumption that RAF1 and SOS1 would account for at least 1% of NS (or 2% of PTPN11-/KRAS-negative NS). Based on Collins and Schwartz (*Am. J. Hum. Genet.* 71:1251-2, 2002), this powered the study to detect a mutation in an NS gene at approximately 80% with α=0.05. If the gene accounted for 5% of PTPN11-/KRAS-negative NS, then the power to detect it with a cohort of this size would exceed 95%.

A high throughput approach to the resequencing of RAF1 and SOS 1 was performed. The resequencing protocol was as follows: oligonucleotide primers (see Table A) for amplifying the RAF1 coding exons (n=17) and SOS1 coding exons (n=23) were designed to give a product size in the range of 200-700 bp with a minimum of 40 bp flanking the splice sites using the Exon Primer program (at the Helmholtz Center Munich's Institute for Human Genomics website), which is bundled with the UCSC Genome Browser (hg17 genome build: at the UCSC Genome Bioinformatics' website). M13F and M13R tags were added to the forward and reverse primers, respectively. Five nanograms of genomic DNA from each NS sample was amplified in an 8 µl PCR reaction using AmpliTaq Gold (Applied Biosystems) using PE 9700 machines and subsequently cleaned using a diluted version of the Exo-SAP based PCR product pre-sequencing kit (USB Corporation) dispensed by a nanoliter dispenser (Deerac Fluidics Equator). All PCR set-up procedures were performed in a 384-well format using a Biomek NX workstation following their optimization. Sequencing reactions were then performed using the M13 primers along with BigDye Terminator v3.1 Cycle Sequencing Kit (Applied Biosystems) and cleaned with BET before separation on an ABI 3730×1 DNA Analyzer. Base calling, quality assessment and assembly were carried out using the Phred, Phrap, Polyphred, Consed software suite (the laboratory of Phil Green website/phrap website). All sequence variants identified were verified by manual inspection of the chromatograms and putative causative mutations were verified using another independent sequencing reaction.

TABLE A

Primer Pairs and Annealing Temperatures Used to Amplify the SOS1 and RAF1 Coding Sequences and Sizes of PCR Products

| Exon | Primer Sequence Forward (SEQ ID NO) | Primer Sequence Reverse (SEQ ID NO) | Annealing Temp (° C.) | Product Length (bp) | DHPLC Temp (° C.) |
|---|---|---|---|---|---|
| (SOS1) | | | | | |
| 1 | 7 | 8 | 64* | 470 | 65.9 |
| 2 | 9 | 10 | 62 | 474 | 55.6 |
| 3 | 11 | 12 | 62 | 399 | 55.2, 56.4 |
| 4 | 13 | 14 | 62 | 428 | 55 |
| 5 | 15 | 16 | 58 | 356 | 53.2, 54.6, 56.5 |
| 6 | 17 | 18 | 62 | 438 | 54.9, 57.1 |
| 7/8 | 19 | 20 | 62 | 479 | 54.2, 56 |
| 9 | 21 | 22 | 58 | 438 | 55 |
| 10 (A) | 23 | 24 | 60 | 507 | 54.2, 56.1, 56.6 |
| 10 (B) | 25 | 26 | 60 | 412 | 52.8, 56.7, 57.9 |
| 11 | 27 | 28 | 58 | 293 | 54, 55 |
| 12 | 29 | 30 | 60 | 371 | 55.5, 57.6 |
| 13 | 31 | 32 | 58 | 321 | 55.4, 56.2 |
| 14 | 33 | 34 | 62 | 423 | 54.7, 58.1 |
| 15 | 35 | 36 | 58 | 290 | 56.6 |
| 16 | 37 | 38 | 62 | 535 | 53.9, 55.9 |
| 17 | 39 | 40 | 64 | 323 | 55.6 |
| 18 | 41 | 42 | 62 | 526 | 53.3, 56 |
| 19 | 43 | 44 | 62 | 421 | 54.3, 55.7 |
| 20 | 45 | 46 | 58 | 465 | 54.9, 58.6 |
| 21 | 47 | 48 | 58 | 419 | 56.3 |
| 22 | 49 | 50 | 58 | 337 | 55.6, 60.7 |
| 23 (A) | 51 | 52 | 62 | 356 | 53.8, 59.5 |
| 23 (B) (RAF1) | 53 | 54 | 62 | 421 | 59.2, 60.5 |
| 2 | 55 | 56 | 62 | 467 | 58.2, 59.5 |
| 3 | 57 | 58 | 62 | 407 | 58.5, 60.2 |
| 4 | 59 | 60 | 62 | 401 | 54, 58 |
| 5 | 61 | 62 | 62 | 363 | 57.5, 58.5, 59.3 |
| 6 | 63 | 64 | 62 | 468 | 57.4 |
| 7 | 65 | 66 | 62 | 270 | 59, 61.3 |
| 8/9 | 67 | 68 | 60 | 356 | 57.4, 60.2, 62.5 |
| 10 | 69 | 70 | 62 | 254 | 58.3, 59.5 |
| 11 | 71 | 72 | 64 | 283 | 58.6, 61.5 |
| 12 | 73 | 74 | 60 | 433 | 60.9 |
| 13 | 75 | 76 | 64 | 223 | 57.4 |
| 14 | 77 | 78 | 64 | 211 | 56.4, 57.2, 61.4 |
| 15 | 79 | 80 | 62 | 282 | 59.8 |
| 16 | 81 | 82 | 62 | 288 | 59.1 |
| 15/16 | 79 | 82 | 62 | 544 | 58.4, 58.8 |
| 17 | 83 | 84 | 60 | 400 | 60.3, 62.5 |

*5% DMSO

Informatics analysis of sequences to predict splice acceptor and donor sites as well as exonic splice enhancers was performed using programs available at the following websites: the NetGene2 server on the Center for Biological Sequence website, the fruitfly.org website, and the ESEfinder on the Zhang lab's Cold Spring Harbor website.

RAF1 Results: In analyzing the 17 RAF1 coding exons in this cohort, three non-synonymous sequencing variants in 7 samples were identified (Table 1). All affected residues were evolutionarily conserved, no change had been reported in a public SNP database, and none of the subjects with a RAF1 variant harbored an SOS1 mutation.

TABLE 1

RAF1 Missense mutations in subjects having NS*

| Exon | DNA Sequence Variant[†] | Amino Acid Substitution[‡] | RAF1 Domain | Observations | Confirmatory Method[¥] |
|---|---|---|---|---|---|
| 7 | 768G→C/T | R256S | CR2 | 1 | |
| 7 | 770C→T | S257L | CR2 | 7 | de novo |
| 7 | 776C→T | S259F | CR2 | 1 | Controls |
| 7 | 779C→G | T260R | CR2 | 1 | Controls |
| 7 | 781C→T | P261S | CR2 | 2 | Controls |
| 7 | 782C→G | P261R | CR2 | 1 | |
| 7 | 782C→T | P261L | CR2 | 1 | de novo |
| 14 | 1456G→A | D486N | CR3 | 1 | Controls |
| 14 | 1457A→G | D486G | CR3 | 1 | Controls |
| 14 | 1472C→T | T491I | CR3 | 1 | Controls |
| 14 | 1472C→G | T491R | CR3 | 1 | Controls |
| 16 | 1834T→A | S612T | C-Term | 1 | Controls |
| 16 | 1837C→G | L613V | C-Term | 1 | de novo |

*A total of 248 subjects suspected of having NS were examined (Cohort A, n = 96; Cohort B, n = 152). Also, 210 control individuals were examined for mutations.
[†]Nucleotides numbers are based on the coding region of RAF1, which begins at nucleotide 394 in SEQ ID NO: 1.
[‡]Amino acids are numbered based on SEQ ID NO: 2.
[¥]Examined parental sequence to verify de novo (sporadic) origin. Some of the population examined had no parental data available, but mutations did not appear in "Controls."

One RAF1 variant predicting the substitution of leucine for S257 was observed in five subjects, and a second resided nearby, altering P261. For the case harboring the L613V change, as well as the four cases with a S257L variant, both parental DNAs were available and analyzed. The relevant sequence change was not found in the parents in all cases. Paternity was confirmed in each case, which provided final proof that the identified variants were de novo mutations. The case harboring the P261 S was familial—this variant was found in the affected father. Since this coinheritance could have occurred by chance, 210 control individuals were analyzed. Failing to observe the P261S variant in the control population, this change was deemed to be a disease-causing mutation. The prevalence of RAF1 mutations in Cohort A was 7/96 or 7.3% (95% C.I.:3.0-14.5%) and 7/83 or 8.4% (3.5-16.6%) of NS without previously identified mutation. Both can be considered lower limits due to the incomplete coverage inherent with our high throughput approach.

SOS1 Results: In analyzing the SOS1 coding exons in this cohort, 33 sequencing variants, including 12 non-synonymous changes observed in 15 samples, were identified (Table 2). Strikingly, three variants, affecting six subjects, altered Arg552 and a fourth affected Leu550. Both residues are evolutionarily conserved.

TABLE 2

SOS1 Missense mutations in subjects having NS*

| Exon | DNA Sequence Variant[†] | Amino Acid Substitution[‡] | SOS1 Domain | Cohort (Observations) | Confirmatory Method[¥] |
|---|---|---|---|---|---|
| 4 | 322G→A | E108K | HF | B (2) | Controls |
| 7 | 806T→G | M269R | DH | B (1) | de novo |
| 11 | 1294T→C | W432R | PH | A (1) | Controls |
| 11 | 1297G→A | E433K | PH | A (1) | Controls |
| 11 | 1297G→A | E433K | PH | B (1) | Controls |
| 11 | 1322G→A | C441Y | PH | B (1) | de novo |
| 11 | 1642A→C | S548R | PH-Rem Linker | B (2) | de novo |
| 11 | 1649T→C | L550P | PH-Rem Linker | A (1) | Controls |
| 11 | 1654A→G | R552G | PH-Rem Linker | A (4) | de novo |
| 11 | 1654A→G | R552G | PH-Rem Linker | B (1) | de novo |
| 11 | 1655G→A | R552K | PH-Rem Linker | A (1) | de novo |
| 11 | 1656G→C | R552S | PH-Rem Linker | A (1) | de novo |
| 11 | 1656G→C | R552S | PH-Rem Linker | B (1) | de novo |
| 13 | 1964C→T | P655L | Rem | A (1) | Polymorph |
| 14 | 2104T→C | Y702H | Rem | A (1) | Controls |
| 15 | 2186G→T | W729L | Rem | A (1) | de novo |
| 15 | 2197A→T | I733F | Rem | A (1) | de novo |
| 17 | 2536G→A | E846K | Cdc25 | A (1) | Controls |
| 19 | 2930A→G | Q977R | Cdc25 | B (1) | Mut (?) |
| 24 | 3959A→G | H1320R | C-Term | A (1) | Mut (?) |

*A total of 129 subjects suspected of having NS were examined (Cohort A, n = 96; Cohort B, n = 33). Also, 155 control individuals were examined for mutations.
[†]Nucleotides are numbered based on SEQ ID NO: 3.
[‡]Amino acids are numbered based on SEQ ID NO: 4.
[¥]Examined parental sequence to verify de novo (sporadic) origin. Some of the population examined had no parental data available, but mutations did not appear in "Controls."
"Polymorph" is a variant found in one control and, therefore, is considered a polymorphism.
"Mut (?)" refers to variants not found in controls but found in an unaffected parent, which may be due either to a rare polymorphism or to incomplete penetrance.

Among the seven variants from sporadic cases for which both parental DNA samples were available, the relevant sequence change was not present in either parent in five; paternity was confirmed in each, providing final proof that these were de novo mutations (Table 2). For the two variants inherited from unaffected parents (P655L and H1320R), as well as two sporadic cases without parental samples (E433K and E846K) and three nonsynonymous variants cosegregating with disease in families with two to three affected individuals (W432R, L550P, and Y702H), only P655L was identified among the 155 control individuals. The H1320R change may be a rare polymorphism, but incomplete penetrance in the unaffected carrier cannot be ruled out (i.e., an NS mutation without a phenotype). The remaining five variants were deemed disease-causing mutations. The prevalence of SOS1 mutations in the cohort was 13/96 or 12.5% (95% C.I.: 7.4-22%), a lower limit due to the incomplete coverage inherent with our high throughput approach.

Example 2

RAF1 and SOS1 Mutant Polypeptide Activity

A. Analysis of Basal and Signal-Dependent MEK Kinase Activity by Mutated RAF1

To investigate the role of RAF1 on MEK kinase activity, RAF1 variants S257L and P261S identified in NS were expressed in Cos-1 cells. Briefly, Cos1 cells were transfected with FLAG-tagged RAF1 (5 µg DNA) using lipofectamine (Invitrogen). After 48 h of expression, cells were serum starved for 16 hours, washed twice with chilled PBS and lysed in 1 ml chilled RIPA buffer (50 mM Tris pH 8.0, 150 mM NaCl, 10 mM EDTA, 10% glycerol, 1% Triton X-100, 0.1% SDS, 1× protease inhibitor cocktail). The lysates containing 800 µg-1 mg protein were incubated with 4 µg of FLAG antibody overnight at about 4° C. Lysates were further incubated with 40 µl Protein G-Sepharose beads (Roche) for 1 hr at about 4° C. The bead-immune complexes were washed three times with chilled IP wash buffer (50 mM Tris pH 8.0, 150 mM NaCl, 0.2% tritonX, 1× protease inhibitor) and finally once with the RAF1 assay reaction buffer. Beads were incubated with inactive MEK1 (Raf1 kinase assay kit, Upstate) at 30° C. for 1 h with shaking. The reaction was stopped by adding SDS loading buffer, boiled for 5 min at 95° C., and the proteins were separated by SDS PAGE. Products were detected by western blot using phosphoMEK antibody (Upstate, 1:2000 dilution) and goat anti-rabbit IRDye680 secondary antibody (LI-COR, 1:10000). RAF1 was detected by FLAG antibody (Sigma, 1:2000 dilution) and goat anti-mouse IRDye800CW secondary antibody (LI-COR, 1:10000). Subsequently, protein bands were visualized using the Odyssey Infrared Imaging System (LI-COR). Relative MEK phosphorylation ratios were quantified using the Odyssey software, normalized to total RAF expression. Both RAF1 variants S257L and P261S had increased MEK kinase activity basally and in response to EGF stimulation as compared to wild type RAF1 (data not shown).

Previously, it was shown that Raf1 mutant S257L, the most common NS-associated RAF1 defect identified in this disclosure, had normal phosphorylation of Ser259, failed to bind protein 14-3-3, and had increased kinase activity (Light et al., Mol. Cell Biol. 22:4984-96, 2002). Using anti-pSer259 antibody, we found that S257L had normal phosphorylation of Ser259, but RAF1 variant P261S did not.

Finally, the 14-3-3 binding site at Ser621 of RAF1 will be eliminated and double mutants, S257L/S621A and P261S/S621A, examined for protein 14-3-3 binding. A lack of 14-3-3 binding will indicate that these two NS-associated RAF1 mutants have a gain-of-function through similar, but not identical, mechanisms because only the alteration of Pro261 will eliminate the kinase recognition at Ser 259. The Leu613 residue had not been identified as important for RAF1 regulation, while phosphorylation of Ser621 and subsequent 14-3-3 binding may be needed for RAF1 activation. The relevant kinase has not been identified, but the −8 position of Leu613 seems unlikely to alter recognition for that kinase or 14-3-3. The L613V mutant was expressed in Cos-1 cells and, as observed with the S257L and P261S mutants, the L613V RAF1 mutant had increased MEK kinase activity basally and following EGF stimulation (data not shown). A RAF1 S259A/L613V double mutant is expressed in Cos-1 cells and examined for protein 14-3-3 binding.

B. Analysis of Basal and Signal-Dependent Ras Activation by Mutated SOS1

To investigate the role of SOS1 on RAS activation, GST-RAF-RBD fusion proteins were expressed in *Escherichia coli* by induction with 0.5 mM of isopropyl-1-thio-β-D-galactopyranoside (IPTG) for 5 hours. The expressed fusion proteins were isolated from bacterial lysates by affinity chromatography with glutathione agarose beads for 1 h at about 4° C. Cos-1 cells were co-transfected with HA-tagged RAS and wild type (WT) or mutant SOS1. Twenty-four hours after transfection, cells were switched to serum-starvation medium (0% DMEM) for 16 h. Following stimulation with EGF (10 ng/ml) for the indicated intervals at about 37° C., cells were collected in RBD lysis buffer containing 25 mM Tris-HCl (pH7.4), 120 mM NaCl, 10 mM $MgCl_2$, 1 mM EDTA, 10% glycerol, 50 mM NaF, 10 mg/ml pepstatin, 1% aprotinin, 10 µg/ml leupeptin, 1 mM $Na_3VO_4$, 10 mM benzamidine, 10 µg/ml soybean trypsin inhibitor, 1% NP40, 0.25% sodium deoxycholic acid. For each condition, 400 µg of whole cell lysate was pre-cleared with 10 µl 50% GST for 5 min at about 4° C. The samples were then centrifuged and supernatants were transferred to Eppendorf tubes containing 20 µg GST-RAF-RBD immobilized beads. Samples were incubated for 1.5 h at about 4° C. The complexes were collected by centrifugation and washed six times with buffer containing 25 mM Tris-HCl (pH 7.4), 120 mM NaCl, 10 mM $MgCl_2$, 1 mM EDTA, 10% glycerol, 50 mM NaF, 1% NP40. Protein complexes were eluted with SDS sample buffer, separated by SDS-12.5% PAGE, and transferred to nitrocellulose membrane. The proteins were detected by western blot with anti-HA antibody (12CA5; 1:10,000) and goat anti-mouse HRP conjugated secondary antibody (Cappel; 1:10,000).

Figure 3A:
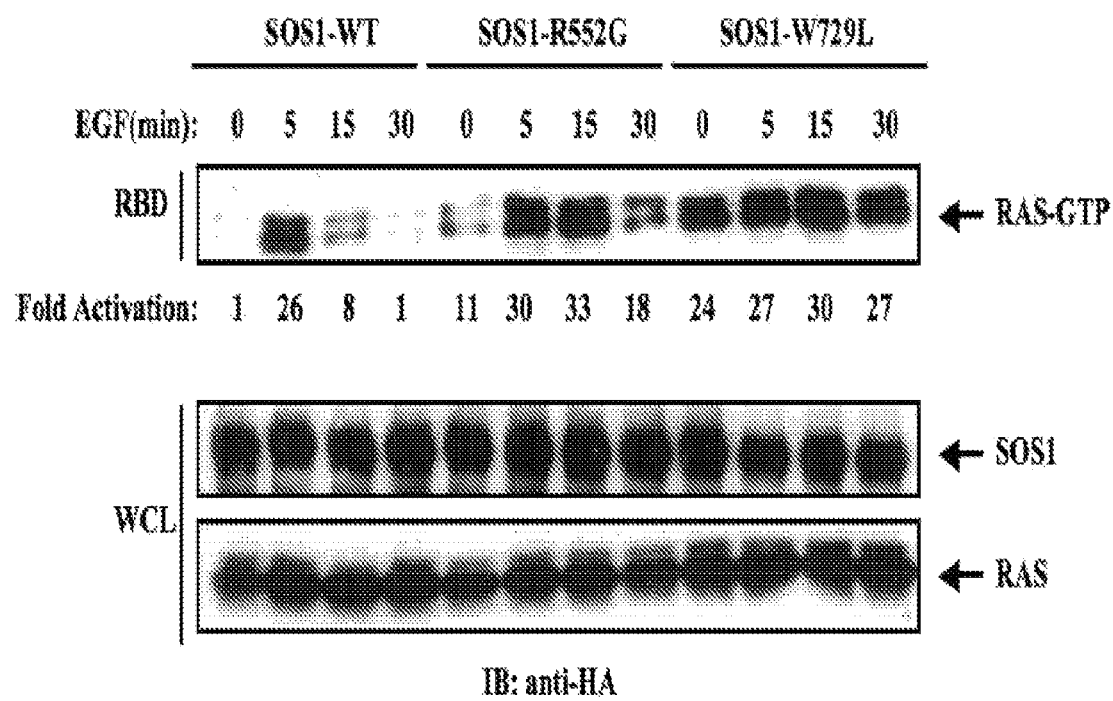
FIGS. 3A and 3B show RAS activation assays—full-length, HA-tagged wild-type SOS1 (WT), SOS1 variant R552G, and SOS1 variant W729L were individually expressed in Cos-1 cells with HA-RAS. Binding of RAS to RAF-RBD was assayed to assess RAS activation in serum-starved cells (0 min) and after 5, 15 and 30 min of EGF stimulation. (A) Total RAS and SOS1 proteins in the whole cell lysates (WCL), shown in the lower two panels, and activated RAS, upper panel, were detected immunologically with anti-HA. All fold activation ratios were compared to SOS-WT at 0 min. (B) Relative fold increase in RAS activation over basal WT SOS1, averaged from three replicates. Results from the mutants were compared to wild type at the same time points using one-tailed T-tests. Significant differences of $p<0.05$ are indicated with *.
Figure 3B:
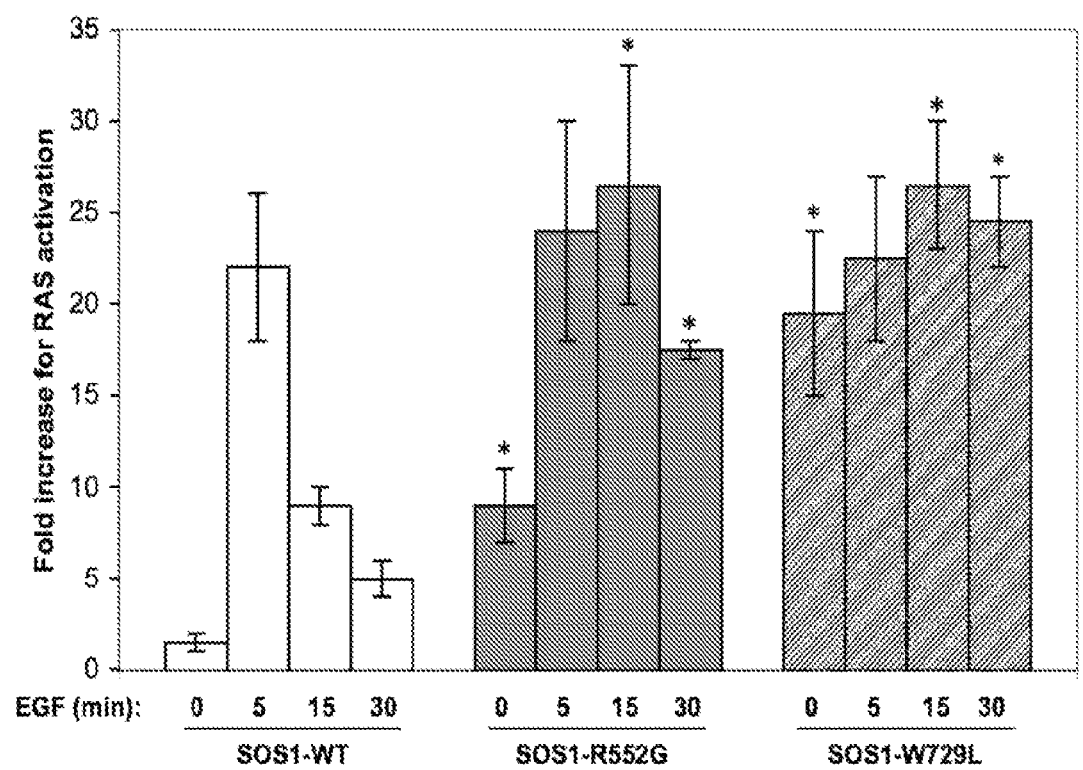

Two representative SOS1 mutants, R552G and W729L, were expressed transiently in Cos-1 cells. When wild type SOS1 was expressed, RAS activation was low in serum-deprived cells, then increased rapidly after EGF stimulation and finally returned toward basal levels by 30 min (FIGS. 3A and 3B). In contrast, expression of SOS1 variant R552G resulted in an increase in the basal level of active RAS and prolonged RAS activation following EGF stimulation. Expression of the W729L variant resulted in essentially constitutive RAS activation.

C. Effect of Mutated SOS1 on the ERK MAP Kinase Cascade

To investigate the role of SOS1 on the RAS-MAPK signaling pathway, Cos-1 cells were transfected with expression vectors encoding HA-ERK2 and HA-tagged SOS1 constructs. After 24 hours of expression, cells were serum starved for 16 hours and lysed in IP buffer (1% Triton X-100, 50 mM TrisCl [pH 7.5], 150 mM NaCl, 10% glycerol) supplemented with protease inhibitors. Lysates were immunoprecipitated with anti-HA monoclonal antibody (12CA5) and subsequently incubated with 1:1 protein A slurry. Beads were washed three times with IP buffer and resuspended in a SDS sample buffer. Samples were run on SDS-PAGE and then transferred to nitrocellulose membranes. Membranes were probed by anti-HA antibody or anti-ERK2 (Upstate Biotechnology) and anti-pERK (Cell Signaling) antibodies. Relative ERK phosphorylation ratios were quantified using the Odyssey software, and normalized to total ERK expression.

Figure 4A:
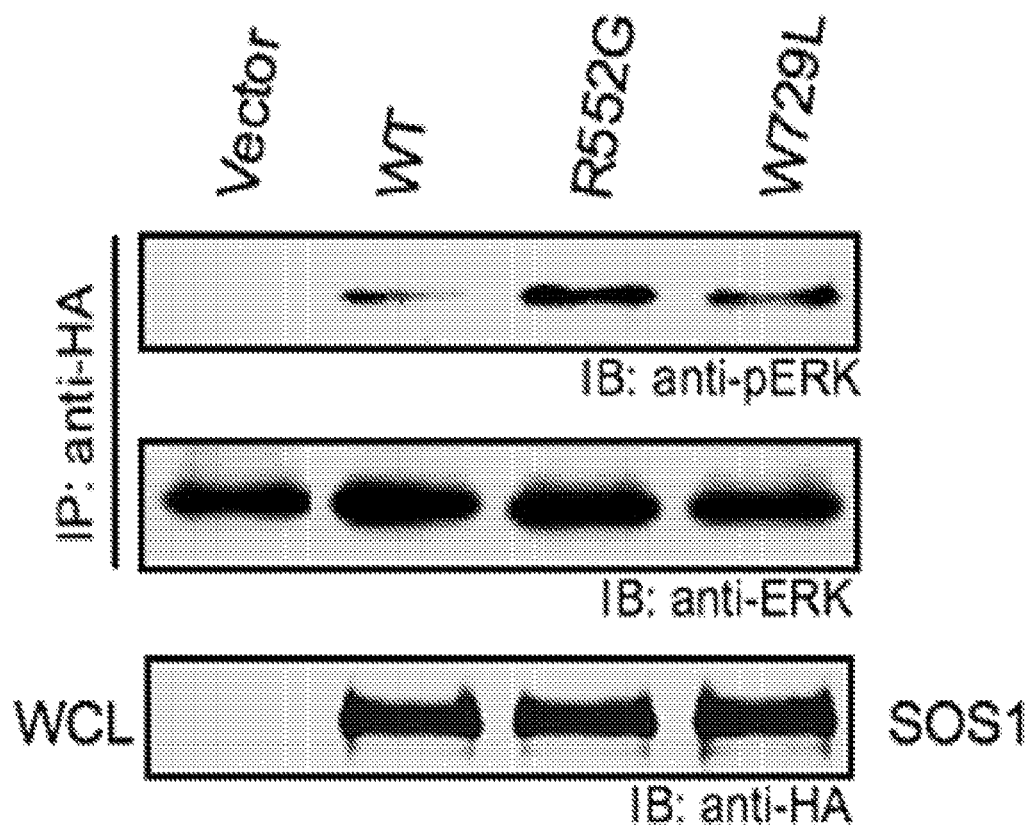
FIGS. 4A and 4B show ERK activation assays—full-length, HA-tagged wild-type SOS1 (WT), SOS1 variant R552G, and SOS1 variant W729L SOS1 were individually expressed in Cos-1 cells with HA-ERK2. The fraction of ERK that was phosphorylated was assayed to assess ERK activation in serum-starved cells. (A) Total SOS1 proteins in the WCL, shown in the lowest panel, were detected with anti-HA. Total ERK and phosphoERK (pERK) in the HA immunoprecipitates were detected with anti-ERK and anti-pERK antibodies in the middle and upper panels, respectively. (B) Relative fold increase in ERK activation basally over untransfected cells, averaged from three replicates.
Figure 4B:
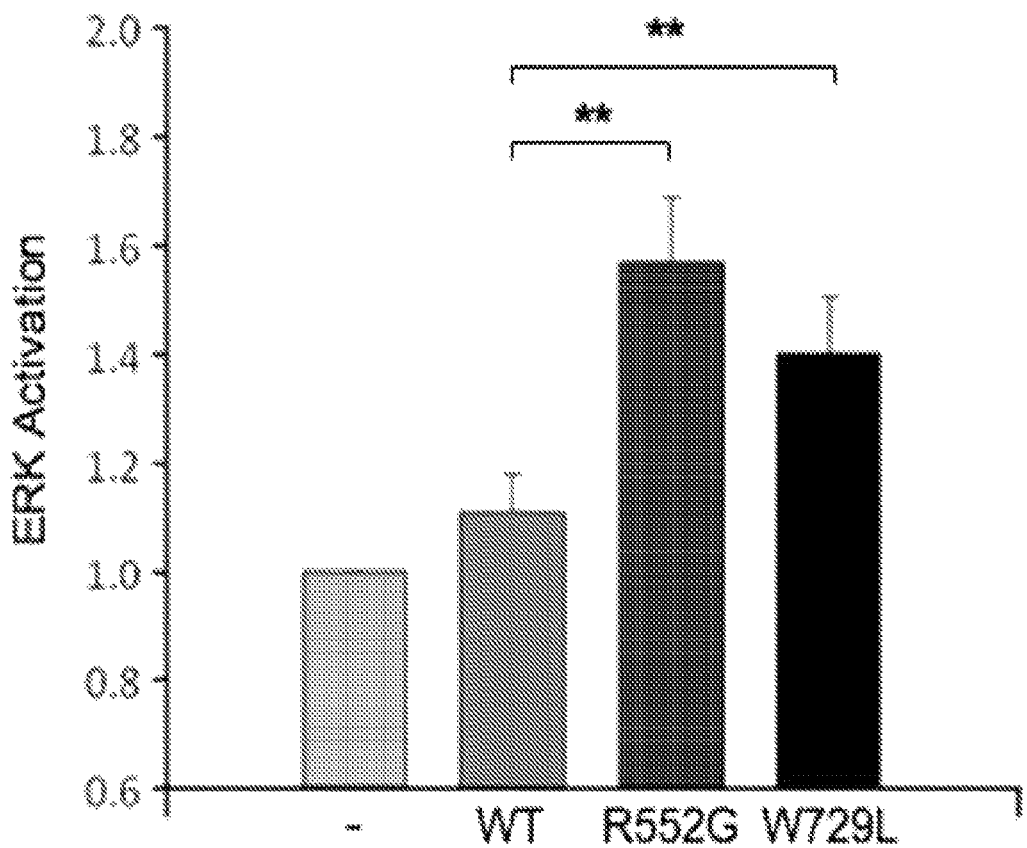

In serum-deprived cells, expression of SOS1 variants R552G and W729L resulted in modest increases in pERK compared to wild type (FIGS. 4A and 4B). EGF-induced ERK activation did not differ among the SOS1 proteins (not shown).

D. Conclusions

These results confirm that the NS-associated SOS1 mutations would principally abrogate autoinhibition, increasing RAS activation that would result in increased downstream signaling (i.e., gain-of-function mutants). Notably, tryptophan (W) at position 729 is involved in mediating the binding of RAS at the allosteric site, which potentiates exchange activity (Sondermann et al., *Cell* 119:393-405, 2004). Indeed, a W729E substitution in SOS1 was previously shown to abrogate the binding of RAS-GTP to the allosteric site and reduce GEF activity (Id.). The NS-associated W729L substitution is more conservative, and its gain-of-function effect is consistent with a preferential targeting of autoinhibition.

The allosteric site is bracketed by the Cdc25 domain and Rem domains. Basally, the catalytic output of SOS1 is constrained by the DH-PH unit (Corbalan-Garcia et al., 1998), and structural data indicate that this autoinhibitory effect is exerted through DH-PH-mediated blockade of the allosteric site (Sondermaun et al., 2004). The three NS-associated SOS1 mutation clusters reside in regions within the molecule that are predicted to contribute structurally to the maintenance of the autoinhibition. Arg552 lies in the helical linker between the PH and Rem domains (FIG. 2A) and is predicted to interact directly with the side chains of Asp140 and Asp169 in the histone domain of SOS1 (Sondermann et al., *Proc. Nat'l. Acad. Sci. USA* 102:16632-7, 2005). Disruption of this interaction could affect the relative orientation of the DH-PH unit and the Rem domain. The mutation cluster represented by W432R, E433K and C441Y may disrupt the autoinhibited conformation by destabilizing the conformation of the DH domain. The third cluster (M269R, W729L and I733F) includes residues that mediate the interaction of the DH and Rem domains. Trp729 interacts directly with Met269, thereby positioning the DH domain in its autoinhibitory conformation (Sondermann et al., 2004). Notably, mutation of Met269 was also identified in an NS patient.

In addition, the RAF1 mutants disclosed herein also appear to involve gain-of-function changes as described herein.

Example 3

RAF1 and SOS1 Mutations in Noonan Syndrome: Molecular Spectrum, Genotype-Phenotype Correlation, and Phenotypic Heterogeneity A. Analysis of Second NS Cohort To elucidate further the range of molecular defects, SOS1 was scanned in a second panel of 33, and RAF1 was scanned in a second panel of 152, SOS1-negative/PTPN11-negative/KRAS-negative NS genomic DNAs. These panels were used as confirmatory of the results of the first panel (Cohort A) and to extend the range of SOS1 and RAF1 mutations associated with NS. These DNAs were scanned for SOS1 and RAF1 mutations using DHPLC analysis of PCR-generated amplimers at column temperatures recommended by the Navigator version 1.5.4.23 software. DHPLC buffers and run conditions were as follows: buffer A (0.1M triethylammonium acetate (TEAA), 0.025% acetonitrile (ACN)), buffer B (0.1M TEAA, 25% ACN); a flow rate of 0.9 ml/min; and a gradient duration of 3 min, with active clean (75% ACN). The percentage of Buffer B used ranged from about 48-56% (loading), about 53-60% (initial), and about 59-67% (final), with temperatures ranging from about 53° C. to 66° C. (see Table A). Positive controls—that is, PCR products expected to result in variant elution profiles—were used in all DHPLC runs.

Amplimers having abnormal denaturing profiles were purified (Microcon PCR, Millipore) and sequenced bi-directionally using the ABI BigDye terminator Sequencing Kit v.1.1 (Applied Biosystems) and an ABI Prism 310 Genetic Analyzer (Applied Biosystems). When available, parental DNAs were sequenced to establish whether the identified changes were de novo. Paternity was confirmed by simple tandem repeat (STR) genotyping using the AmpF/STR Identifier PCR Amplification Kit (Applied Biosystems). Anonymous Caucasian control genomic DNAs were screened for SOS1 and RAF1 coding exons in which putative mutations had been identified using DHPLC and abnormal amplimers were sequenced bi-directionally as described above. Eighty-five (85) additional Caucasian control DNAs were digested with MneI Sew England Biolabs) or BsrsI (Promega) to further exclude occurrence of the SOS1 1297G→A and 1649T→C missense changes, respectively. The results provide a more extensive assessment of the range of SOS1 and RAF1 lesions causing NS, establishment of genotype-phenotype correlations, and identifying phenotypes associated with mutations.

RAF1 Results: DHPLC analysis of this second group of 152 NS subjects without known mutation allowed identification of eleven missense changes in twelve sporadic cases or families transmitting the trait (Table 1). Five mutations were found in Ser257, Pro261 or adjacent residues, which further confirms the functional relevance of mutations affecting this amino acid stretch. The remaining five changes involved residues Asp486, Thr491 and Ser612, which is indicative of two additional mutational hotspots (see Table 1). Available parental DNAs demonstrated the de novo origin of mutation in two sporadic cases, and genotyping of affected and unaffected members of families transmitting the disorder documented cosegregation in the four kindreds analyzed. No novel variants were found in the controls. These results confirm that at least 13 RAF1 mutants are involved in NS.

SOS1 Results: This analysis revealed nine subjects with SOS1 missense mutations, as well as another probable rare nonsynonymous polymorphism, Q977R, inherited from an unaffected mother (Table 2). In this Cohort B, two additional mutations altering Arg552 and two independent S548R alleles were observed, emphasizing the importance of that region. A second mutation cluster in SOS1's Pleckstrin Homology (PH) domain became apparent with the identification of an additional instance of E433K as well as a C441Y mutant. A third functional cluster residing in the interacting regions of the Dbl homology (DH) and RAS exchanger motif (Rem) domain was apparent with the identification of M269R, which joined W729L and I733F identified in Cohort A (Table 2). These results confirm that at least 14 SOS1 mutants are involved in NS.

B. Clinical Evaluation

Noonan syndrome. Subjects were examined by clinicians experienced with NS. Electrocardiograms, echocardiograms, and clinical photographs were obtained routinely for the probands, as well as for most of other affected family members in the kindreds segregating the disorder. NS was diagnosed on the basis of the presence of the following major characteristics: typical facial dysmorphia, pulmonic stenosis or hypertrophic cardiomyopathy (HCM) plus abnormal electrocardiogram pattern, pectus carinatum/excavatum, height >2 SD below the mean, and cryptorchidism in male subjects. To have a diagnosis of NS, individuals with typical facial dysmorphia had to have at least one additional major feature, whereas individuals with suggestive facial findings had to have at least two other major characteristics (van der Burgt et al., Am. J. Med. Genet. 53:187-91, 1994). HCM was diagnosed when the left-ventricular maximal end diastolic wall thickness was >1.5 cm in adults (Shapiro and McKenna, J. Am. Coll. Cardiol. 2:437-44, 1983) or >2 SD above the mean for a given age in children (Burch et al., J. Am. Coll. Cardiol. 22:1189-92, 1993). The clinical description of kindred with Noonan-like/multiple giant-cell lesion syndrome was reported elsewhere (Bertola et al., Am. J. Med. Genet. 98:230-4, 2001). Informed consent was obtained from all subjects included in the study.

SOS1 Genotype-Phenotype Correlation. Extensive phenotype data were available for 16 individuals with SOS1 missense mutations. These individuals had cardiac disease (primarily pulmonary valve stenosis), pectus deformities, shorted and webbed neck, and dysmorphic facial features ranging from typical for NS to an appearance resembling CFC (Table 3). Ectodermal features including facial keratosis pilaris, hypoplastic eyebrows and curly hair were significantly more prevalent among individuals with a SOS1 mutation compared to the general NS population. Height below the third centile was observed in only 2 of 15 individuals with a SOS1 mutation, whereas prevalence is 70-76% among NS in general and PTPN11 mutation-negative NS. In contrast, macrocephaly was overrepresented among those with SOS1 mutations. Only one individual with a SOS1 mutation had mental retardation, potentially attributable to critical illness as a newborn. In comparison, 30 and 35% of all children with NS and those without a PTPN11 mutation, respectively, require special education. Genotype-phenotype correlations were performed using 2×2 contingency-table analysis. The significance threshold was set at $P<0.05$.

TABLE 3

Genotype-Phenotype Correlation

| | No./Total (%) of Subjects | | |
|---|---|---|---|
| Clinical Feature | SOS1 Mutation | All[a] | Without PTPN11 Mutation[b] |
| Polyhydramnios | 8/15 (53) | 43/130 (33) | NA |
| Fetal Macrosomia | 9/15 (60) | NA | NA |
| Short Stature (<3rd centile) | 2/15 (13) | 84/115 (73)*** | 45/64 (70)*** |
| Macrocephaly | 9/16 (56) | 19/151 (12)*** | NA |
| Downslanting Palpebral Fissures | 15/16 (94) | NA | NA |
| Ptosis | 16/16 (100) | NA | NA |
| Low-Set Ears with Thickened Helix | 16/16 (100) | NA | NA |

TABLE 3-continued

Genotype-Phenotype Correlation

| | No./Total (%) of Subjects | | |
| --- | --- | --- | --- |
| Clinical Feature | SOS1 Mutation | All[a] | Without PTPN11 Mutation[b] |
| Thick Lips/Macrostomia | 14/16 (88) | NA | NA |
| Short/Webbed Neck | 15/16 (94) | NA | NA |
| Abnormal Pectus | 16/16 (100) | 144/151 (95) | 46/61 (75)* |
| Cardiac Involvement | 13/16 (81) | 132/151 (87) | 42/66 (64) |
| Pulmonary Valve Stenosis | 10/16 (62) | 93/151 (62) | 30/65 (46) |
| Septal Defect | 4/16 (25) | 29/151 (19) | 11/63 (18) |
| HCM | 2/16 (12) | 30/151 (20) | 17/65 (26) |
| Facial Keratosis Pilaris | 8/16 (50) | 21/151 (14)*** | NA |
| Curly Hair | 14/16 (88) | 44/151 (29)*** | NA |
| Cryptorchidism | 6/9 (67) | 64/83 (77) | 25/35 (71) |
| Mental Retardation | 1/16 (6) | 32/105 (30)* | 21/59 (36)* |
| Bleeding Diathesis | 5/16 (31) | 37/151 (25) | NA |

[a]See Sharland et al., Arch. Dis. Child 67: 178-83, 1992;
[b]See Tartaglia et al., 2002;
Significance:
*<.05;
**<.01;
***<.001;
Definitions:
HCM, hypertrophic cardiomyopathy;
NA, not available.

SOS1 Discussion. SOS1 analysis in PTPN11-/KRAS-mutation-negative NS cohorts identified mutations in 17% of subjects having NS. Like PTPN11, SOS1 mutations were found in sporadic and familial NS and engendered a high prevalence of pulmonary valve disease. The SOS1-associated phenotype, while clearly within the NS spectrum, resembled cardio-facio-cutanteous (CFC) syndrome in its dysmorphia, macrocephaly and ectodermal manifestations, but differed notably with preserved development (i.e., lack of mental retardation) and linear growth (i.e., normal stature). Among mutations causing developmental disorders with dysregulated RAS-MAPK signaling, SOS1 defects are notable for affecting a protein functioning upstream of RAS. An exon 21, frameshift mutation of SOS1 was reported in one family inheriting the autosomal dominant trait, hereditary gingival fibromatosis (Hart et al., *Am. J. Hum. Genet.* 70:943-54, 2002). But, this is the first report of inherited gain-of-function mutations in SOS1.

The biochemical analysis of two NS-related SOS1 proteins revealed gain-of-function effects resulting in increased RAS activation. Since many of the SOS1 mutations target residues that contribute to SOS autoinhibition, either by stabilizing the interaction of the histone folds with the PH-Rem linker or interaction of the DH domain with the Rem domain, the predominant pathogenetic mechanism appears to be a release of autoinhibition followed by an enhanced GEF activity and, as a consequence, increased RAS-GTP levels. GTP-bound RAS has been shown to interact with and activate multiple downstream effector pathways[23]. In addition, the DH-PH module of SOS has been implicated in the activation of the Rho GTPase Rac[24].

The two highly conserved vertebrate SOS genes are widely expressed[25]. Sos1 and Sos2 bind a docking protein, Grb2, with different affinities[26] and Sos2 cannot compensate for the loss of Sos1 in the Sos1 knockout mice, suggesting that these proteins play unique roles. The possibility that SOS2 mutations might also cause NS, similar to those in SOS1, was examined. But, no SOS2 sequence changes at homologous positions were detected.

RAF1 Genotype-Phenotype Correlation. Genotype-phenotype analyses have established that pulmonary valve stenosis is more prevalent among NS patients with PTPN11 mutation while HCM is quite rare. SOS1 and KRAS mutations are associated with distinct NS phenotypes, the former including ectodermal abnormalities, normal stature, and normal development, while the latter is associated with severe NS approaching CFC; neither has stereotypic cardiac features (Carta et al., 2006; Schubbert et al., 2006; Zenker et al., *J. Pediatr.* 144:368-74, 2004). Since SOS1 and KRAS mutation prevalence in NS is approximately 8% and 2%, respectively, 40% of NS remains unexplained, including most cases with hypertrophic cardiomyopathy (HCM). Phenotype analysis of the NS subjects with RAF1 mutations was notable for the observation that nearly all of them had HCM.

Previously, there have been several lines of evidence implicating RAS-MAPK signaling in compensatory and pathological cardiac hypertrophy. In cell culture, the hypertrophic response of murine cardiomyocytes to agents such as phenylephrine can be abrogated using pharmacologic inhibitors, anti-sense oligonucleotides and expression of dominant-negative proteins directed at Raf1, Mek1 and Erk1/2. Transgenic mice expressing activated Hras or Mek1 develop cardiac hypertrophy. Similarly, roughly one-half of patients with Costello syndrome and gain-of-function HRAS mutation have HCM (Estep et al., *Am. J. Med. Genet. A* 140:8-16, 2006; Gripp et al., *Am. J. Med. Genet. A* 140:1-7, 2006; Kerr et al., *J. Med. Genet.* 43:401-5, 2006; Zampino et al., *Hum. Mutat.*, 2006). Conversely, expression of a dominant-negative form of Raf-1 in mice increases apoptosis and reduces cardiac hypertrophy in response to a pressure overload stimulus.

RAF1 Discussion. RAF1 analysis in PTPN11-/KRAS-mutation-negative NS cohorts identified mutations in 7.5% of subjects having NS. Like PTPN11 and SOS1, mutations were found in sporadic and familial NS and engendered a high prevalence of hypertrophic cardiomyopathy (HCM). The noteworthy finding here is that RAF1 mutations result in HCM. Indeed, this is the first instance of this cardiac problem originating invariably from altered RAS-MAPK signaling in humans.

The present disclosure is not to be limited in scope by the specific embodiments described herein. Indeed, various modifications of this disclosure in addition to those described herein will become apparent to those skilled in the art from the foregoing description and the accompanying figures. Such modifications are intended to fall within the scope of the appended claims. It is further to be understood that all values are approximate, and are provided for description.

Patents, patent applications, publications, product descriptions, and protocols are cited throughout this application, the disclosures of which are incorporated herein by reference in their entireties for all purposes.

What is claimed is:

1. A method for diagnosing Noonan syndrome in a human subject, comprising amplifying all or part of a RAS-specific guanine nucleotide exchange factor (SOS1) nucleic acid molecule from a biological sample of the subject, and detecting a mutation in the SOS1 nucleic acid molecule, wherein the mutation results in an SOS1 polypeptide comprising an amino acid substitution at a position selected from the group consisting of:
   (a) a W to R substitution at position 432 of SEQ ID NO:4;
   (b) an E to K substitution at position 433 of SEQ ID NO:4; and
   (c) a C to Y substitution at position 441 of SEQ ID NO:4,
   and wherein the presence of said mutation in said SOS1 nucleic acid molecule is diagnostic of Noonan syndrome in said human subject.

2. The method of claim 1, wherein the mutation in the SOS1 nucleic acid molecule is selected from the group consisting of:
   (a) a T to C substitution at position 1294 of SEQ ID NO:3;
   (b) a G to A substitution at position 1297 of SEQ ID NO:3; and
   (c) a G to A substitution at position 1322 of SEQ ID NO:3,
   and wherein the presence of said mutation in said SOS1 nucleic acid molecule is diagnostic of Noonan syndrome in said human subject.

3. A method for diagnosing Noonan syndrome in a human subject, comprising obtaining a biological sample from the subject, and detecting a mutation in a RAS-specific guanine nucleotide exchange factor (SOS1) nucleic acid molecule from the sample, wherein the mutation results in an SOS1 polypeptide comprising an amino acid substitution at a position selected from the group consisting of:
   (a) a W to R substitution at position 432 of SEQ ID NO:4;
   (b) an E to K substitution at position 433 of SEQ ID NO:4; and
   (c) a C to Y substitution at position 441 of SEQ ID NO:4,
   and wherein the presence of said mutation in said SOS1 nucleic acid molecule is diagnostic of Noonan syndrome in said human subject.

4. The method of claim 3, wherein the mutation in the SOS1 nucleic acid molecule is selected from the group consisting of:
   (a) a T to C substitution at position 1294 of SEQ ID NO:3;
   (b) a G to A substitution at position 1297 of SEQ ID NO:3; and
   (c) a G to A substitution at position 1322 of SEQ ID NO:3,
   and wherein the presence of said mutation in said SOS1 nucleic acid molecule is diagnostic of Noonan syndrome in said human subject.

5. A method for diagnosing Noonan syndrome in a human subject, comprising sequencing all or part of a RAS-specific guanine nucleotide exchange factor (SOS1) nucleic acid molecule from the subject, and detecting a mutation in the SOS1 nucleic acid molecule, wherein the mutation results in an SOS1 polypeptide comprising an amino acid substitution at a position selected from the group consisting of:
   (a) a W to R substitution at position 432 of SEQ ID NO:4;
   (b) an E to K substitution at position 433 of SEQ ID NO:4; and
   (c) a C to Y substitution at position 441 of SEQ ID NO:4,
   and wherein the presence of said mutation in said SOS1 nucleic acid molecule is diagnostic of Noonan syndrome in said human subject.

6. The method of claim 5, wherein the mutation in the SOS1 nucleic acid molecule is selected from the group consisting of:
   (a) a T to C substitution at position 1294 of SEQ ID NO:3;
   (b) a G to A substitution at position 1297 of SEQ ID NO:3; and
   (c) a G to A substitution at position 1322 of SEQ ID NO:3,
   and wherein the presence of said mutation in said SOS1 nucleic acid molecule is diagnostic of Noonan syndrome in said human subject.

* * * * *

SEQUENCE LISTING

<160> NUMBER OF SEQ ID NOS: 125

<210> SEQ ID NO 1
<211> LENGTH: 3245
<212> TYPE: DNA
<213> ORGANISM: Homo sapiens

<400> SEQUENCE: 1

```
cgcaggtcgg gaggacgagc accgagtcga gggctcgctc gtctgggccg cccgagagtc      60
ttaatcgcgg gcgcttgggc cgccatctta gatggcggga gtaagaggaa aacgattgtg     120
aggcgggaac ggctttctgc tgcctttttt gggccccgaa aagggtcagc tggccgggct     180
ttggggcgcg tgccctgagg cgcggagcgc gtttgctacg atgcggggc tgctcggggc      240 ggggaggagg agcgggcgag aagctgccgc cgaacgacag gacgttgggg cggcctggct     300
tccgtcccct gggctgggga cgcgccgaat gtgaccgcct cccgctccct cacccgccgc     360
ccctcaggtt taagaattgt ttaagctgca tcaatggagc acatacaggg agcttggaag     420
acgatcagca atggttttgg attcaaagat gccgtgtttg atggctccag ctgcatctct     480
cctacaatag ttcagcagtt tggctatcag cgccgggcat cagatgatgg caaactcaca     540
gatccttcta agacaagcaa cactatccgt gttttcttgc cgaacaagca agaacagtg      600 gtcaatgtgc gaaatggaat gagcttgcat gactgcctta tgaaagcact caaggtgagg     660
ggcctgcaac cagagtgctg tgcagtgttc agacttctcc acgaacacaa aggtaaaaaa     720
gcacgcttag attggaatac tgatgctgcg tctttgattg gagaagaact tcaagtagat     780
ttcctggatc atgttcccct cacaacacac aactttgctc ggaagacgtt cctgaagctt     840
gccttctgtg acatctgtca gaaattcctg ctcaatggat ttcgatgtca gacttgtggc     900
tacaaatttc atgagcactg tagcaccaaa gtacctacta tgtgtgtgga ctggagtaac     960
atcagacaac tcttattgtt tccaaattcc actattggtg atagtggagt cccagcacta    1020
ccttctttga ctatgcgtcg tatgcgagag tctgtttcca ggatgcctgt tagttctcag    1080
cacagatatt ctacacctca cgccttcacc tttaacacct ccagtccctc atctgaaggt    1140
tccctctccc agaggcagag gtcgacatcc acacctaatg tccacatggt cagcaccacc    1200
ctgcctgtgg acagcaggat gattgaggat gcaattcgaa gtcacagcga atcagcctca    1260
ccttcagccc tgtccagtag ccccaacaat ctgagcccaa caggctggtc acagccgaaa    1320 accccgtgc cagcacaaag agagcgggca ccagtatctg ggacccagga gaaaaacaaa    1380
attaggcctc gtggacagag agattcaagc tattattggg aaatagaagc cagtgaagtg    1440
atgctgtcca ctcggattgg gtcaggctct ttggaacttg tttataaggg taatggcac     1500 ggagatgttg cagtaaagat cctaaaggtt gtcgacccaa ccccagagca attccaggcc    1560
ttcaggaatg aggtggctgt tctgcgcaaa acacggcatg tgaacattct gcttttcatg    1620
gggtacatga caaaggacaa cctggcaatt gtgacccagt ggtgcgaggg cagcagcctc    1680
tacaaacacc tgcatgtcca ggagaccaag tttcagatgt ccagctaat tgacattgcc     1740 cggcagacgc tcagggaat ggactatttg catgcaaaga acatcatcca tagagacatg    1800
aaatccaaca atattttct ccatgaaggc ttaacagtga aaattggaga ttttggtttg    1860
```

```
gcaacagtaa agtcacgctg gagtggttct cagcaggttg aacaacctac tggctctgtc    1920
ctctggatgg ccccagaggt gatccgaatg caggataaca acccattcag tttccagtcg    1980
gatgtctact cctatggcat cgtattgtat gaactgatga cggggggagct tccttattct    2040 cacatcaaca accgagatca gatcatcttc atggtgggcc gaggatatgc ctccccagat    2100
cttagtaagc tatataagaa ctgccccaaa gcaatgaaga ggctggtagc tgactgtgtg    2160
aagaaagtaa aggaagagag gcctcttttt ccccagatcc tgtcttccat tgagctgctc    2220
caacactctc taccgaagat caaccggagc gcttccgagc catccttgca tcgggcagcc    2280
cacactgagg atatcaatgc ttgcacgctg accacgtccc cgaggctgcc tgtcttctag    2340
ttgactttgc acctgtcttc aggctgccag gggaggagga gaagccagca ggcaccactt    2400
ttctgctccc tttctccaga ggcagaacac atgttttcag agaagctgct gctaaggacc    2460
ttctagactg ctcacagggc cttaacttca tgttgccttc ttttctatcc ctttgggccc    2520
tgggagaagg aagccatttg cagtgctggt gtgtcctgct ccctcccac attccccatg     2580 ctcaaggccc agccttctgt agatgcgcaa gtggatgttg atggtagtac aaaaagcagg    2640
ggcccagccc cagctgttgg ctacatgagt atttagagga agtaaggtag caggcagtcc    2700
agccctgatg tggagacaca tgggattttg gaaatcagct tctggaggaa tgcatgtcac    2760
aggcgggact ttcttcagag agtggtgcag cgccagacat tttgcacata aggcaccaaa    2820
cagcccagga ctgccgagac tctggccgcc gaaggagcc tgctttggta ctatggaact     2880
tttcttaggg gacacgtcct cctttcacag cttctaaggt gtccagtgca ttgggatggt    2940
tttccaggca aggcactcgg ccaatccgca tctcagccct ctcagggagc agtcttccat    3000
catgctgaat tttgtcttcc aggagctgcc cctatggggc ggggccgcag ggccagcctt    3060
gtttctctaa caaacaaaca aacaaacagc cttgtttctc tagtcacatc atgtgtatac    3120
aaggaagcca ggaatacagg ttttcttgat gatttgggtt ttaattttgt ttttattgca    3180
cctgacaaaa tacagttatc tgatggtccc tcaattatgt tatttttaata aaataaatta    3240 aattt                                                                3245

<210> SEQ ID NO 2
<211> LENGTH: 648
<212> TYPE: PRT
<213> ORGANISM: Homo sapiens

<400> SEQUENCE: 2

Met Glu His Ile Gln Gly Ala Trp Lys Thr Ile Ser Asn Gly Phe Gly
  1               5                  10                  15

Phe Lys Asp Ala Val Phe Asp Gly Ser Ser Cys Ile Ser Pro Thr Ile
             20                  25                  30

Val Gln Gln Phe Gly Tyr Gln Arg Arg Ala Ser Asp Asp Gly Lys Leu
         35                  40                  45

Thr Asp Pro Ser Lys Thr Ser Asn Thr Ile Arg Val Phe Leu Pro Asn
     50                  55                  60

Lys Gln Arg Thr Val Val Asn Val Arg Asn Gly Met Ser Leu His Asp
 65                  70                  75                  80

Cys Leu Met Lys Ala Leu Lys Val Arg Gly Leu Gln Pro Glu Cys Cys
                 85                  90                  95

Ala Val Phe Arg Leu Leu His Glu His Lys Gly Lys Lys Ala Arg Leu
            100                 105                 110

Asp Trp Asn Thr Asp Ala Ala Ser Leu Ile Gly Glu Glu Leu Gln Val
        115                 120                 125
```

```
Asp Phe Leu Asp His Val Pro Leu Thr Thr His Asn Phe Ala Arg Lys
    130                 135                 140

Thr Phe Leu Lys Leu Ala Phe Cys Asp Ile Cys Gln Lys Phe Leu Leu
145                 150                 155                 160

Asn Gly Phe Arg Cys Gln Thr Cys Gly Tyr Lys Phe His Glu His Cys
                165                 170                 175

Ser Thr Lys Val Pro Thr Met Cys Val Asp Trp Ser Asn Ile Arg Gln
            180                 185                 190

Leu Leu Leu Phe Pro Asn Ser Thr Ile Gly Asp Ser Gly Val Pro Ala
        195                 200                 205

Leu Pro Ser Leu Thr Met Arg Arg Met Arg Glu Ser Val Ser Arg Met
210                 215                 220

Pro Val Ser Ser Gln His Arg Tyr Ser Thr Pro His Ala Phe Thr Phe
225                 230                 235                 240

Asn Thr Ser Ser Pro Ser Ser Glu Gly Ser Leu Ser Gln Arg Gln Arg
                245                 250                 255

Ser Thr Ser Thr Pro Asn Val His Met Val Ser Thr Thr Leu Pro Val
            260                 265                 270

Asp Ser Arg Met Ile Glu Asp Ala Ile Arg Ser His Ser Glu Ser Ala
        275                 280                 285

Ser Pro Ser Ala Leu Ser Ser Pro Asn Asn Leu Ser Pro Thr Gly
290                 295                 300

Trp Ser Gln Pro Lys Thr Pro Val Pro Ala Gln Arg Glu Arg Ala Pro
305                 310                 315                 320

Val Ser Gly Thr Gln Glu Lys Asn Lys Ile Arg Pro Arg Gly Gln Arg
                325                 330                 335

Asp Ser Ser Tyr Tyr Trp Glu Ile Glu Ala Ser Glu Val Met Leu Ser
            340                 345                 350

Thr Arg Ile Gly Ser Gly Ser Phe Gly Thr Val Tyr Lys Gly Lys Trp
        355                 360                 365

His Gly Asp Val Ala Val Lys Ile Leu Lys Val Val Asp Pro Thr Pro
370                 375                 380

Glu Gln Phe Gln Ala Phe Arg Asn Glu Val Ala Val Leu Arg Lys Thr
385                 390                 395                 400

Arg His Val Asn Ile Leu Leu Phe Met Gly Tyr Met Thr Lys Asp Asn
                405                 410                 415

Leu Ala Ile Val Thr Gln Trp Cys Glu Gly Ser Ser Leu Tyr Lys His
            420                 425                 430

Leu His Val Gln Glu Thr Lys Phe Gln Met Phe Gln Leu Ile Asp Ile
        435                 440                 445

Ala Arg Gln Thr Ala Gln Gly Met Asp Tyr Leu His Ala Lys Asn Ile
450                 455                 460

Ile His Arg Asp Met Lys Ser Asn Asn Ile Phe Leu His Glu Gly Leu
465                 470                 475                 480

Thr Val Lys Ile Gly Asp Phe Gly Leu Ala Thr Val Lys Ser Arg Trp
                485                 490                 495

Ser Gly Ser Gln Gln Val Glu Gln Pro Thr Gly Ser Val Leu Trp Met
            500                 505                 510

Ala Pro Glu Val Ile Arg Met Gln Asp Asn Asn Pro Phe Ser Phe Gln
        515                 520                 525

Ser Asp Val Tyr Ser Tyr Gly Ile Val Leu Tyr Glu Leu Met Thr Gly
530                 535                 540

Glu Leu Pro Tyr Ser His Ile Asn Asn Arg Asp Gln Ile Ile Phe Met
```

```
545               550               555               560
Val Gly Arg Gly Tyr Ala Ser Pro Asp Leu Ser Lys Leu Tyr Lys Asn
                565               570               575
Cys Pro Lys Ala Met Lys Arg Leu Val Ala Asp Cys Val Lys Lys Val
            580               585               590
Lys Glu Glu Arg Pro Leu Phe Pro Gln Ile Leu Ser Ser Ile Glu Leu
        595               600               605
Leu Gln His Ser Leu Pro Lys Ile Asn Arg Ser Ala Ser Glu Pro Ser
    610               615               620
Leu His Arg Ala Ala His Thr Glu Asp Ile Asn Ala Cys Thr Leu Thr
625               630               635               640
Thr Ser Pro Arg Leu Pro Val Phe
            645

<210> SEQ ID NO 3
<211> LENGTH: 4002
<212> TYPE: DNA
<213> ORGANISM: Homo sapiens

<400> SEQUENCE: 3
```

| | | | | | |
|---|---|---|---|---|---|
| atgcaggcgc | agcagctgcc | ctacgagttt | ttcagcgaag | agaacgcgcc | caagtggcgg | 60 |
| ggactactgg | tgcctgcgct | gaaaaaggtc | caggggcaag | ttcatcctac | tctcgagtct | 120 |
| aatgatgatg | ctcttcagta | tgttgaagaa | ttaattttgc | aattattaaa | tatgctatgc | 180 |
| caagctcagc | cccgaagtgc | ttcagatgta | gaggaacgtg | ttcaaaaaag | tttccctcat | 240 |
| ccaattgata | aatgggcaat | agctgatgcc | caatcagcta | ttgaaaagag | gaagcgaaga | 300 |
| aacccttat | ctctcccagt | agaaaaaatt | catcctttat | taaggaggt | cctaggttat | 360 |
| aaaattgacc | accaggtttc | tgtttacata | gtagcagtct | tagaatacat | ttctgcagac | 420 |
| atttttaaagc | tggttgggaa | ttatgtaaga | aatatacggc | attatgaaat | tacaaaacaa | 480 |
| gatattaaag | tggcaatgtg | tgctgacaag | gtattgatgg | atatgtttca | tcaagatgta | 540 |
| gaagatatta | atatattatc | tttaactgac | gaagagcctt | ccacctcagg | agaacaaact | 600 |
| tactatgatt | tggtaaaagc | atttatggca | gaaattcgac | aatatataag | ggaactaaat | 660 |
| ctaattataa | aagttttag | agagcccttt | gtctccaatt | caaaattgtt | ttcagctaat | 720 |
| gatgtagaaa | atatatttag | tcgcatagta | gatatacatg | aacttagtgt | aaagttactg | 780 |
| ggccatatag | aagatacagt | agaaatgaca | gatgaaggca | gtccccatcc | actagtagga | 840 |
| agctgctttg | aagacttagc | agaggaactg | gcattttgatc | catatgaatc | gtatgctcga | 900 |
| gatattttgc | gacctggttt | tcatgatcgt | tccttagtc | agttatcaaa | gcctggggca | 960 |
| gcactttatt | tgcagtcaat | aggcgaaggt | tcaaagaag | ctgttcaata | tgttttaccc | 1020 |
| aggctgcttc | tggcccctgt | ttaccactgt | ctccattact | ttgaactttt | gaagcagtta | 1080 |
| gaagaaaaaa | gtgaagatca | agaagacaag | gaatgtttaa | acaagcaat | aacagctttg | 1140 |
| cttaatgttc | agagtggtat | ggaaaaaata | tgttctaaaa | gtcttgcaaa | acgaagactg | 1200 |
| agtgaatctg | catgtcggtt | ttatagtcag | caaatgaagg | ggaaacaact | agcaatcaag | 1260 |
| aagatgaacg | agattcagaa | gaatattgat | ggttgggagg | aaaagacat | tggacagtgt | 1320 |
| tgtaatgaat | ttataatgga | aggaactctt | acacgtgtag | agccaaaaca | tgagagacac | 1380 |
| atatttctct | ttgatggctt | aatgatttgc | tgtaaatcaa | atcatgggca | gccaagactt | 1440 |
| cctggtgcta | gcaatgcaga | atatcgtctt | aagaaaagt | tttttatgcg | aaaggtacaa | 1500 |
| attaatgata | aagatgacac | caatgaatac | aagcatgctt | ttgaaataat | tttaaagat | 1560 |

```
gaaaatagtg ttatattttc tgccaagtca gctgaagaga aaaacaattg gatggcagca   1620
ttgatatctt tacagtaccg gagtacactg gaaaggatgc ttgatgtaac aatgctacag   1680
gaagagaaag aggagcagat gaggctgcct agtgctgatg tttatagatt tgcagagcct   1740
gactctgaag agaatattat atttgaagag aacatgcagc ccaaggctgg aattccaatt   1800
atcaaagcag gaactgttat taaacttata gagaggctta cgtaccatat gtacgcagat   1860
cccaattttg ttcggacatt tcttacaaca tacagatcct tttgcaaacc tcaagaacta   1920
ctgagtctta aatagaaag gtttgaaatt ccagagcctg agccaacaga agctgatcgc   1980
atagctatag agaatggaga tcaacccttg agtgcagaac tgaaaagatt tagaaaagaa   2040
tatatacagc ctgtgcaact gcgagtatta aatgtatgtc ggcactgggt agagcaccac   2100
ttctatgatt ttgaaagaga tgcatatctt ttgcaacgaa tggaagaatt tattggaaca   2160
gtaagaggta aagcaatgaa aaaatgggtt gaatccatca ctaaaataat ccaaaggaaa   2220
aaaattgcaa gagacaatgg accaggtcat aatattacat tcagagttc acctcccaca    2280 gttgagtggc atataagcag acctgggcac atagagactt ttgacctgct caccttacac   2340
ccaatagaaa ttgctcgaca actcacttta cttgaatcag atctataccg agctgtacag   2400
ccatcagaat tagttggaag tgtgtggaca aaagaagaca agaaattaa ctctcctaat    2460 cttctgaaaa tgattcgaca taccaccaac ctcactctgt ggtttgagaa atgtattgta   2520
gaaactgaaa atttagaaga aagagtagct gtggtgagtc gaattattga gattctacaa   2580
gtctttcaag agttgaacaa ctttaatggt gtccttgagg ttgtcagtgc tatgaattca   2640
tcacctgttt acagactaga ccacacattt gagcaaatac caagtcgcca gaagaaaatt   2700
ttagaagaag ctcatgaatt gagtgaagat cactataaga aatatttggc aaaactcagg   2760
tctattaatc caccatgtgt gccttctctt ggaatttatc tcactaatat cttgaaaaca   2820
gaagaaggca cccctgaggt cctaaaaaga catggaaaag agcttataaa cttttagcaaa   2880 aggaggaaag tagcagaaat aacaggagag atccagcagt accaaaatca gccttactgt   2940
ttacgagtag aatcagatat caaaaggttc tttgaaaact tgaatccgat gggaaatagc   3000
atggagaagg aatttacaga ttatcttttc aacaaatccc tagaaataga accacgaaac   3060
cctaagcctc tcccaagatt tccaaaaaaa tatagctatc ccctaaaatc tcctggtgtt   3120
cgtccatcaa acccaagacc aggtaccatg aggcatccca cacctctgca gcaggagcca   3180
aggaaaatta gttatagtag gatccctgaa agtgaaacag aaagtacagc atctgcacca   3240
aattctccaa gaacaccgtt aacacctccg cctgcttctg gtgcttccag taccacagat   3300
gtttgcagtg tatttgattc cgatcattcg agccctttc actcaagcaa tgataccgtc   3360
tttatccaag ttactctgcc ccatggccca agatctgctt ctgtatcatc tataagttta   3420
accaaaggca ctgatgaagt gcctgtccct cctcctgttc ctccacgaag acgaccagaa   3480
tctgccccag cagaatcttc accatctaag attatgtcta agcatttgga cagtcccccca   3540 gccattcctc ctaggcaacc cacatcaaaa gcctattcac cacgatattc aatatcagac   3600
cggacctcta tctcagaccc tcctgaaagc cctcccttat taccaccacg agaacctgtg   3660
aggacacctg atgttttctc aagctcacca ctacatctcc aacctccccc tttgggcaaa   3720
aaaagtgacc atggcaatgc cttcttccca aacagccctt ccccctttac accacctcct   3780
cctcaaacac cttctcctca cggcacaaga aggcatctgc catcaccacc attgacacaa   3840
gaagtggacc ttcattccat tgctgggccg cctgttcctc cacgacaaag cacttctcaa   3900
catatcccta aactccctcc aaaaacttac aaaagggagc acacacaccc atccatgcac   3960
```

```
agagatggac caccactgtt ggagaatgcc cattcttcct ga                    4002
```

<210> SEQ ID NO 4
<211> LENGTH: 1333
<212> TYPE: PRT
<213> ORGANISM: Homo sapiens

<400> SEQUENCE: 4

```
Met Gln Ala Gln Gln Leu Pro Tyr Glu Phe Ser Glu Glu Asn Ala
 1               5                  10                  15

Pro Lys Trp Arg Gly Leu Leu Val Pro Ala Leu Lys Val Gln Gly
                20                  25                  30

Gln Val His Pro Thr Leu Glu Ser Asn Asp Asp Ala Leu Gln Tyr Val
                35                  40                  45

Glu Glu Leu Ile Leu Gln Leu Leu Asn Met Leu Cys Gln Ala Gln Pro
     50                  55                  60

Arg Ser Ala Ser Asp Val Glu Glu Arg Val Gln Lys Ser Phe Pro His
 65                  70                  75                  80

Pro Ile Asp Lys Trp Ala Ile Ala Asp Ala Gln Ser Ala Ile Glu Lys
                85                  90                  95

Arg Lys Arg Arg Asn Pro Leu Ser Leu Pro Val Glu Lys Ile His Pro
                100                 105                 110

Leu Leu Lys Glu Val Leu Gly Tyr Lys Ile Asp His Gln Val Ser Val
                115                 120                 125

Tyr Ile Val Ala Val Leu Glu Tyr Ile Ser Ala Asp Ile Leu Lys Leu
    130                 135                 140

Val Gly Asn Tyr Val Arg Asn Ile Arg His Tyr Glu Ile Thr Lys Gln
145                 150                 155                 160

Asp Ile Lys Val Ala Met Cys Ala Asp Lys Val Leu Met Asp Met Phe
                165                 170                 175

His Gln Asp Val Glu Asp Ile Asn Ile Leu Ser Leu Thr Asp Glu Glu
                180                 185                 190

Pro Ser Thr Ser Gly Glu Gln Thr Tyr Tyr Asp Leu Val Lys Ala Phe
                195                 200                 205

Met Ala Glu Ile Arg Gln Tyr Ile Arg Glu Leu Asn Leu Ile Ile Lys
    210                 215                 220

Val Phe Arg Glu Pro Phe Val Ser Asn Ser Lys Leu Phe Ser Ala Asn
225                 230                 235                 240

Asp Val Glu Asn Ile Phe Ser Arg Ile Val Asp Ile His Glu Leu Ser
                245                 250                 255

Val Lys Leu Leu Gly His Ile Glu Asp Thr Val Glu Met Thr Asp Glu
                260                 265                 270

Gly Ser Pro His Pro Leu Val Gly Ser Cys Phe Glu Asp Leu Ala Glu
                275                 280                 285

Glu Leu Ala Phe Asp Pro Tyr Glu Ser Tyr Ala Arg Asp Ile Leu Arg
    290                 295                 300

Pro Gly Phe His Asp Arg Phe Leu Ser Gln Leu Ser Lys Pro Gly Ala
305                 310                 315                 320

Ala Leu Tyr Leu Gln Ser Ile Gly Glu Gly Phe Lys Glu Ala Val Gln
                325                 330                 335

Tyr Val Leu Pro Arg Leu Leu Leu Ala Pro Val Tyr His Cys Leu His
                340                 345                 350

Tyr Phe Glu Leu Leu Lys Gln Leu Glu Glu Lys Ser Glu Asp Gln Glu
                355                 360                 365

Asp Lys Glu Cys Leu Lys Gln Ala Ile Thr Ala Leu Leu Asn Val Gln
```

-continued

```
            370                 375                 380
Ser Gly Met Glu Lys Ile Cys Ser Lys Ser Leu Ala Lys Arg Arg Leu
385                 390                 395                 400

Ser Glu Ser Ala Cys Arg Phe Tyr Ser Gln Gln Met Lys Gly Lys Gln
                405                 410                 415

Leu Ala Ile Lys Lys Met Asn Glu Ile Gln Lys Asn Ile Asp Gly Trp
                420                 425                 430

Glu Gly Lys Asp Ile Gly Gln Cys Cys Asn Glu Phe Ile Met Glu Gly
                435                 440                 445

Thr Leu Thr Arg Val Gly Ala Lys His Glu Arg His Ile Phe Leu Phe
450                 455                 460

Asp Gly Leu Met Ile Cys Cys Lys Ser Asn His Gly Gln Pro Arg Leu
465                 470                 475                 480

Pro Gly Ala Ser Asn Ala Glu Tyr Arg Leu Lys Glu Lys Phe Phe Met
                485                 490                 495

Arg Lys Val Gln Ile Asn Asp Lys Asp Thr Asn Glu Tyr Lys His
                500                 505                 510

Ala Phe Glu Ile Ile Leu Lys Asp Glu Asn Ser Val Ile Phe Ser Ala
                515                 520                 525

Lys Ser Ala Glu Glu Lys Asn Asn Trp Met Ala Ala Leu Ile Ser Leu
530                 535                 540

Gln Tyr Arg Ser Thr Leu Glu Arg Met Leu Asp Val Thr Met Leu Gln
545                 550                 555                 560

Glu Glu Lys Glu Glu Gln Met Arg Leu Pro Ser Ala Asp Val Tyr Arg
                565                 570                 575

Phe Ala Glu Pro Asp Ser Glu Glu Asn Ile Ile Phe Glu Glu Asn Met
                580                 585                 590

Gln Pro Lys Ala Gly Ile Pro Ile Ile Lys Ala Gly Thr Val Ile Lys
                595                 600                 605

Leu Ile Glu Arg Leu Thr Tyr His Met Tyr Ala Asp Pro Asn Phe Val
610                 615                 620

Arg Thr Phe Leu Thr Thr Tyr Arg Ser Phe Cys Lys Pro Gln Glu Leu
625                 630                 635                 640

Leu Ser Leu Ile Ile Glu Arg Phe Glu Ile Pro Glu Pro Glu Pro Thr
                645                 650                 655

Glu Ala Asp Arg Ile Ala Ile Glu Asn Gly Asp Gln Pro Leu Ser Ala
                660                 665                 670

Glu Leu Lys Arg Phe Arg Lys Glu Tyr Ile Gln Pro Val Gln Leu Arg
                675                 680                 685

Val Leu Asn Val Cys Arg His Trp Val Glu His His Phe Tyr Asp Phe
690                 695                 700

Glu Arg Asp Ala Tyr Leu Leu Gln Arg Met Glu Glu Phe Ile Gly Thr
705                 710                 715                 720

Val Arg Gly Lys Ala Met Lys Lys Trp Val Glu Ser Ile Thr Lys Ile
                725                 730                 735

Ile Gln Arg Lys Lys Ile Ala Arg Asp Asn Gly Pro Gly His Asn Ile
                740                 745                 750

Thr Phe Gln Ser Ser Pro Pro Thr Val Glu Trp His Ile Ser Arg Pro
                755                 760                 765

Gly His Ile Glu Thr Phe Asp Leu Leu Thr Leu His Pro Ile Glu Ile
                770                 775                 780

Ala Arg Gln Leu Thr Leu Leu Glu Ser Asp Leu Tyr Arg Ala Val Gln
785                 790                 795                 800
```

```
Pro Ser Glu Leu Val Gly Ser Val Trp Thr Lys Glu Asp Lys Glu Ile
            805                 810                 815

Asn Ser Pro Asn Leu Leu Lys Met Ile Arg His Thr Thr Asn Leu Thr
        820                 825                 830

Leu Trp Phe Glu Lys Cys Ile Val Glu Thr Glu Asn Leu Glu Glu Arg
            835                 840                 845

Val Ala Val Val Ser Arg Ile Ile Glu Ile Leu Gln Val Phe Gln Glu
    850                 855                 860

Leu Asn Asn Phe Asn Gly Val Leu Glu Val Val Ser Ala Met Asn Ser
865                 870                 875                 880

Ser Pro Val Tyr Arg Leu Asp His Thr Phe Glu Gln Ile Pro Ser Arg
            885                 890                 895

Gln Lys Lys Ile Leu Glu Glu Ala His Glu Leu Ser Glu Asp His Tyr
        900                 905                 910

Lys Lys Tyr Leu Ala Lys Leu Arg Ser Ile Asn Pro Pro Cys Val Pro
    915                 920                 925

Phe Phe Gly Ile Tyr Leu Thr Asn Ile Leu Lys Thr Glu Glu Gly Asn
930                 935                 940

Pro Glu Val Leu Lys Arg His Gly Lys Glu Leu Ile Asn Phe Ser Lys
945                 950                 955                 960

Arg Arg Lys Val Ala Glu Ile Thr Gly Glu Ile Gln Gln Tyr Gln Asn
            965                 970                 975

Gln Pro Tyr Cys Leu Arg Val Glu Ser Asp Ile Lys Arg Phe Phe Glu
        980                 985                 990

Asn Leu Asn Pro Met Gly Asn Ser Met Glu Lys Glu Phe Thr Asp Tyr
    995                 1000                1005

Leu Phe Asn Lys Ser Leu Glu Ile Glu Pro Arg Asn Pro Lys Pro Leu
    1010                1015                1020

Pro Arg Phe Pro Lys Lys Tyr Ser Tyr Pro Leu Lys Ser Pro Gly Val
1025                1030                1035                1040

Arg Pro Ser Asn Pro Arg Pro Gly Thr Met Arg His Pro Thr Pro Leu
            1045                1050                1055

Gln Gln Glu Pro Arg Lys Ile Ser Tyr Ser Arg Ile Pro Glu Ser Glu
        1060                1065                1070

Thr Glu Ser Thr Ala Ser Ala Pro Asn Ser Pro Arg Thr Pro Leu Thr
    1075                1080                1085

Pro Pro Pro Ala Ser Gly Ala Ser Ser Thr Thr Asp Val Cys Ser Val
    1090                1095                1100

Phe Asp Ser Asp His Ser Ser Pro Phe His Ser Ser Asn Asp Thr Val
1105                1110                1115                1120

Phe Ile Gln Val Thr Leu Pro His Gly Pro Arg Ser Ala Ser Val Ser
            1125                1130                1135

Ser Ile Ser Leu Thr Lys Gly Thr Asp Glu Val Pro Val Pro Pro Pro
        1140                1145                1150

Val Pro Pro Arg Arg Arg Pro Glu Ser Ala Pro Ala Glu Ser Ser Pro
    1155                1160                1165

Ser Lys Ile Met Ser Lys His Leu Asp Ser Pro Pro Ala Ile Pro Pro
    1170                1175                1180

Arg Gln Pro Thr Ser Lys Ala Tyr Ser Pro Arg Tyr Ser Ile Ser Asp
1185                1190                1195                1200

Arg Thr Ser Ile Ser Asp Pro Glu Ser Pro Leu Leu Pro Pro
            1205                1210                1215

Arg Glu Pro Val Arg Thr Pro Asp Val Phe Ser Ser Pro Leu His
    1220                1225                1230
```

Leu Gln Pro Pro Leu Gly Lys Lys Ser Asp His Gly Asn Ala Phe
    1235                1240                1245

Phe Pro Asn Ser Pro Ser Pro Phe Thr Pro Pro Pro Gln Thr Pro
  1250                1255                1260

Ser Pro His Gly Thr Arg Arg His Leu Pro Ser Pro Pro Leu Thr Gln
1265                1270                1275                1280

Glu Val Asp Leu His Ser Ile Ala Gly Pro Pro Val Pro Pro Arg Gln
            1285                1290                1295

Ser Thr Ser Gln His Ile Pro Lys Leu Pro Pro Lys Thr Tyr Lys Arg
        1300                1305                1310

Glu His Thr His Pro Ser Met His Arg Asp Gly Pro Pro Leu Leu Glu
    1315                1320                1325

Asn Ala His Ser Ser
    1330

<210> SEQ ID NO 5
<211> LENGTH: 9203
<212> TYPE: DNA
<213> ORGANISM: Homo sapiens

<400> SEQUENCE: 5

| | | | | | |
|---|---|---|---|---|---|
| atcttagatg | gcgggagtaa | gaggaaaacg | attgtgaggc | gggaacggct | ttctgctgcc | 60 |
| tttttgggc | cccgaaaagg | gtcagctggc | cgggctttgg | ggcgcgtgcc | ctgaggcgcg | 120 |
| gagcgcgttt | gctacgatgc | gggggctgct | cggggctccg | tcccctgggc | tggggacgcg | 180 |
| ccgaatgtga | ccgcctcccg | ctccctcacc | cgccgcgggg | aggaggagcg | ggcgagaagc | 240 |
| tgccgccgaa | cgacaggacg | ttggggcggc | ctggctccct | caggtaggtg | gcaggaccgg | 300 |
| gtcgtggatg | ccgggggagc | cgggcggcgg | ggctgaggga | tcggcttcca | gggcgaccgg | 360 |
| gcctgggtgg | cgctgatgga | gcggccccgc | ggctgccggg | cagagggctt | gggccaggcc | 420 |
| gttgtcaccc | tggggtagcg | ttgggcgggg | gccccggagt | ccgtcctcat | ctatgaaata | 480 |
| tttaatggaa | gtgtactatt | aaagaaactt | tctttgctg | atgaatgcag | gaggtatcat | 540 |
| taaaaaccca | catagtgcta | ttttcataat | tactctttat | gtattgtgtt | cttgggttga | 600 |
| atacttttgt | tctagagtta | caattatttg | tgtttcttac | caggtttaag | aattgtttaa | 660 |
| gctgcatcaa | tggagcacat | acaggggagct | tggaagacga | tcagcaatgg | ttttggattc | 720 |
| aaagatgccg | tgtttgatgg | ctccagctgc | atctctccta | caatagttca | gcagtttggc | 780 |
| tatcagcgcc | gggcatcaga | tgatggcaaa | ctcacagatc | cttctaagac | aagcaacact | 840 |
| atccgtgttt | tcttgccgaa | caagcaaaga | acagtggtat | gtgaacattc | tacttaggaa | 900 |
| atttagctat | ttatctgcct | gtggagcaca | ttaaggatca | tgttcaactt | aaagacaggc | 960 |
| aaaatattca | ttgtcattta | gggtctttat | ttttttttt | ctaactgcag | atttattttt | 1020 |
| ttatattgct | gttccttcca | cacccccctat | ttttctaca | gatgtctcac | actccattca | 1080 |
| agtactttcc | tattgctgga | cattcaggtt | gtttcgtata | tgtgtgtgtg | cgtgggccat | 1140 |
| cacaagcaat | acagactggt | gcatttattt | ctgtgcccac | ctttccaagg | ggtgctgcag | 1200 |
| cctgtgttgg | tcctaaaggt | ggtcctttgt | ttgtaggtca | atgtgcgaaa | tggaatgagc | 1260 |
| ttgcatgact | gccttatgaa | agcactcaag | gtgaggggcc | tgcaaccaga | gtgctgtgca | 1320 |
| gtgttcagac | ttctccacga | acacaaaggg | taagagctca | aaagtcaatt | gacttcttca | 1380 |
| gactagtaag | gatcttctag | cttcaaatag | ctatgtttgt | attaaattgt | actagcttcc | 1440 |
| tatagaatat | tgtatatttc | tataccttc | tttataaaga | gataattcag | aaaaataggt | 1500 |

```
attaagaaat tgaaattatt gcttggacaa acttgctgtg tggccttgag caaattacct    1560
tcttagagtc ccagttttct tattttttcag atagaaataa tacctacttc ataggtttgt   1620
tgtatgaatt aaataaatta ttgttgtatg gattaaataa agttgtgttt atatggcatg   1680
tgataaatgg tagctgttgt tatttctatt gaactttgat cttgtttaaa catttcatgt   1740 ttttttttaaa tcctttctag taaaaaagca cgcttagatt ggaatactga tgctgcgtct   1800
ttgattggag aagaacttca agtagatttc ctggatcatg ttcccctcac aacacacaac   1860
tttgtaagtt gcagatctct tctctttctg gcatgttgag ggctttgcca ggcataacag   1920
agatttctca ggtaatatgc gtatgtatat atatatatag ttggattgtt taaagttctt   1980
tatgctgttg tttacagtaa ggcaatttag atttcattag tcagagatat actctaattt   2040
gtgtacagta aggcaatttta gatttcatta gtcagagata tactctaatt tgtgattatg   2100
aattctgtac atgctggaag tatgattcat tttgtaaaaa cttttttgga ggccaagaaa   2160
tgaagttgtc ttttgtcatc ttttatttat tcagcataat ttacacctgt gttcttgttg   2220
taggctcgga agacgttcct gaagcttgcc ttctgtgaca tctgtcagaa attcctgctc   2280
aatggatttc gatgtcagac ttgtggctac aaatttcatg agcactgtag caccaaagta   2340
cctactatgt gtgtggactg gagtaacatc agacaactct tgtaaggcat tgttcttttta   2400 tccaaggaag atagggatga ggagtataca tactttaaag ggtatttgtt gtagattttg   2460
actgacaggt ctggattcta gactcattta atgaattgtg atccagaaac tactttagaa   2520
acagtgataa ttctgaaact agctaggttt ggtggcattc actgtatgtt tattggcagg   2580
tcagtattat tcacattcaa taatcattca aatccagtta tttggaatat tgttcccttt   2640
attctaggta atgtaaaaca gttgaggaaa atgtgactgg gaaaagttca gttttagtag   2700
ctctgagttt gcaaaagcaa ggcatgctga ttgtctctgt aagattactg caagcctaaa   2760
aaccagtctt tccctgcttt tgtttagatt gttttccaaat tccactattg gtgatagtgg   2820
agtcccagca ctaccttctt tgactatgcg tcgtatgcga gagtctgttt ccaggatgcc   2880
tgttaggtaa ttttttacct atagcttttc ttttagaaag ttatttgggg tggtggggtt   2940
ggaagcttga agacaaaaaa taagagtttc ttcgcattcc ctcctctcta cgtggaaacc   3000
ccttgctgct tctgtggaac ttgatactgg tggtacagaa aaggtagaaa tttctgttta   3060
tggaccaagc acctagactt aagataaattt ttagatgtca cacatttgaa agaatcaaac   3120
attttgtcaa aggttgtaca ggtagagttt gcccttaagc atcttactta gtcaaatatg   3180
tacttgaaag acttccaccag tatgaaagcc taagtgccaa tcatggaatt ttctttctcc   3240
tcctagttct cagcacagat attctacacc tcacgccttc acctttaaca cctccagtcc   3300
ctcatctgaa ggttccctct cccagaggca gaggtcgaca tccacaccta atgtccacat   3360
ggtcagcacc accctgcctg tggacagcag gatgattgag gtaatagggc accttggggg   3420
tggtaatgtc agtcaattaa tggggtgagg ttgatactta tttcagagtt ttgggtttca   3480
aatctgatca aggaatgttg caacactttc tcaggtctct ggactttttac agtttatttt   3540 atatccataa tatcttcaga ctggctgaat agtctggtta gccactgata tttgctgaat   3600
ttaatcaagg aacgttgatt agagtatgtt taggatttct atggttttta gaggttttta   3660
taatctattt tgttcttgca catcctcctc ctctttttttc cctcccccag agaaaatctt   3720
ttgtgtgtag gagttgacca gctttccttt tctgtttcag gatgcaattc gaagtcacag   3780
cgaatcaggt acttttccat agtcatttag ccaacaataa tgggcttttt ttctttatgc   3840
ggtgtatctt ctgttggctt atccttgtgt ggcttctgtt tgtcttgtct attaagcctc   3900
```

```
accttcagcc ctgtccagta gccccaacaa tctgagccca acaggctggt cacagccgaa    3960
aacccccgtc ttttgtgtgt aggagttgac cagcttttcct tttctgtttc aggatgcaat   4020
tcgaagtcac agcgaatcag gtacttttcc atagtcattt agccaacaat aatgggcttt    4080
ttttctttat gcggtgtatc ttctgttggc ttatccttgt gtggcttctg tttgtcttgt    4140
ctattaagcc tcaccttcag ccctgtccag tagccccaac aatctgagcc aacaggctg     4200 gtcacagccg aaaaccccg tgccagcaca agagagcgg gcaccagtat ctgggaccca      4260
ggagaaaaac aaaattgtga gtatagacaa cagtacctcc tgccaattag ggttcagtaa    4320
gaaaaacctc gttggaaatt agaatactta aacttatttt gggagaagat tctaataaaa    4380
tacattcaat gaaggagatt ataaatgtta ctgtcatttt tggcacactt gcatcagaca    4440
gtttgccagt gctataagtt tgccagtgct ataactaaaa tggtatttct caaaagacaa    4500
aaattggaag tatggttaat atgtttatct ttaaaagata tggaaacaga tgacatgggt    4560
tgatcctttg atgccctcat tatcaaaaga ttattaccat tgcatggagt ataataatga    4620
tctctacttg tttcagaggc ctcgtggaca gagagattca agctattatt gggaaataga   4680
agccagtgaa gtgatgctgt ccactcggat tgggtcaggc tcttttggaa ctgtttataa    4740
gggtaaatgg cacggtaagc ttggggccct ccctttacta actgcagggc tttggtgtga    4800
agtcaagttt cagcccaggg ggccaggagg aggagaggac tgagtgctcc tgggcttata    4860
gcagtactct cccttacata cttgattata cctgaagatt gaacttaatt cttttttagac  4920 taagttctta taaatagcct agacaacaga gtgagaccct gtctcaaaaa aaaaaaaaa    4980 attggaaatt tgccgtatct gtgtaggtat gtgattcttt ggataaatga ttcactgtat   5040
cttcctcaaa actaggttat ttgaaagact gagatcattc aactgattgc actgactgcc   5100
aactaatttt gcaggagatg ttgcagtaaa gatcctaaag gttgtcgacc caaccccaga    5160
gcaattccag gccttcagga atgaggtggc tgttctgcgg tgagtagaaa gctggcggtc    5220
cagtccctct ggagtgctgg agtggggagt acaaggactg tagagttagt ggactgtgcc    5280
gcaggttggg acgggcaggc agttaggact cactgtggag tttctgtggt tggatgctcc    5340
tcccttgaga gcaaagggat gtttcccttta gtttatgtgg cttctctttg ctcagaatgc    5400
cacccgggtt atcagccgtg ccatgtgttt gtttttggga ctgggggtgg tgttgggact   5460 ggggggtggtg tcgacagcac agaacccact gtccacggga aagcacagta gacctccctg    5520
agcactttcc tcctcctct cctctcttcc cctccctcc ccagcaaaac acggcatgtg    5580
aacattctgc ttttcatggg gtacatgaca aaggacaacc tggcaattgt gacccagtgg    5640
tgcgagggca gcagcctcta caaacacctg catgtccagg agaccaagtt tcagatgttc    5700
cagctaattg acattgcccg gcagacggct cagggaatgg agtgagtaga tggtctgatg    5760
cctctctggg acccaggcat caaatttgtc cctaaattgg aaccaggatc aggaaaagcc    5820
ttctagtcca ttaagcgatt ctgtgatatc tttgcacaag cctctggcct gggctggagg    5880
ggccaattat caggaatgag ttgttcaggt tccagctggg tgtggcctca ccttcaggta    5940
agcagtgatg tgaaccaggc tgaacagcac agggtctatc cctgtgtgta acactccttg    6000
gagccaggcc ttcagtggct ttacttctta gctgtagttt aaaactgctt tctactcatg    6060
cccctcaaac ttattttaa taatttcttt tcccttcaca gctatttgca tgcaagaac    6120 atcatccata gagacatgaa atccaacagt atcctttggt tgttgagttc atttgactgc    6180
tcggttctaa atttagggaa acagaaggga ggctttctat cacaagtggc tctcggtgcc    6240 agggggatatc tttttaagga aagaggcaga ggacaggaaa acagaaaagt cagaaaatta   6300
```

```
gtaggcttgg cctgtccctc agcagcttct ggaagaaggt gcatttcaaa agcactttaa      6360
agaacttcag aaaccttagg aagttcagtg cagagaggct gtgacagagg taaggtggag      6420
agattaccgt gttataaaga actttgggat atttttcaaa attaacctga ccattctttt      6480
gaaaccagag tccttaacaa gcattgagat atatttctcc atgaaggctt aacagtgaaa      6540
attggagatt ttggtttggc aacagtaaag tcacgctgga gtggttctca gcaggttgaa      6600
caacctactg gctctgtcct ctggatggtg agaatctggg ctcccaccag cagtctctgg      6660
tatagggcaa aaggaatgcc ttggagattt atgtgcaaac ttaaagcgtt tctgtacatt      6720
tccccgaaat ccacatgacc cctagtgaca gccagcctca gggcaattgt agattttctt      6780
gaggaagctg ttgatcagaa ccactgtcaa ggattcctga gctgttttaa ccagtgcctg      6840
agttggagtc ctttggggga aaagctatgt ggggactgaa gaatggactc attcataact      6900
aatgaaaggg acagcctggc ccctagatgt ctgtgaggcc tgtcatatgg tgataaatgc      6960
acttttgtca tatggtgata catgtaggcc ccagaggtga tccgaatgca ggataacaac      7020
ccattcagtt tccagtcgga tgtctactcc tatggcatcg tattgtatga actgatgacg      7080
ggggagcttc cttattctca catcaacaac cgagatcagg taagtctgtg ctggtgcgaa      7140
aggacccaac tcgtgggagc ccctgggcct ccgccagcct aagcagctag agggttagga      7200
cttgttatta tctgttgttc attcaccccc cattagctca gctgtttcct ttcccttaga      7260
tcatcttcat ggtgggccga ggatatgcct ccccagatcg ggggagcttc cttattctca      7320
catcaacaac cgagatcagg taagtctgtg ctggtgcgaa aggacccaac tcgtgggagc      7380
ccctgggcct ccgccagcct aagcagctag agggttagga cttgttatta tctgttgttc      7440
attcaccccc cattagctca gctgtttcct ttcccttaga tcatcttcat ggtgggccga      7500
ggatatgcct ccccagatct tagtaagcta tataagaact gccccaaagc aatgaagagg      7560
ctggtagctg actgtgtgaa gaaagtaaag gaagagaggc ctcttttttcc ccaggtaagg      7620 ctcagggctg ctagaatgtg attaaagcat gggttggttc gtaaagatgg caatataagg      7680
tgggagtgtt ttgtttttgtt ttataggggag gggacccagg tcctctacaa gatggtgggg      7740
ggcagggtac atcctgtgtc tttgagacac agctaatgag agcattcttg ggctagggct      7800
gctagaatgt gattaaagca tgggttggtt cgtaaagatg gcaatataag gtgggagtgt      7860
tttgttttgt tttataggga ggggacccag gtcctctaca agatggtggg gggcagggta      7920
catcctgtgt ctttgagaca cagctaatga gagcattctt gggctttgtt tcagatcctg      7980
tcttccattg agctgctcca acactctcta ccgaagatca accggagcgc ttccgagcca      8040
tccttgcatc gggcagccca cactgaggat atcaatgctt gcacgctgac cacgtccccg      8100
aggctgcctg tcttctagtt gactttgcac ctgtcttcag gctgccaggg gaggaggaga      8160
agccagcagg caccactttt ctgctccctt tctccagagg cagaacacat gttttcagag      8220
aagctgctgc taaggacctt ctagactgct cacagggcct taacttcatg ttgccttctt      8280
ttctatccct ttgggccctg ggagaaggaa gccatttgca gtgctggtgt gtcctgctcc      8340
ctccccacat tccccatgct caaggcccag ccttctgtag atgcgcaagt ggatgttgat      8400
ggtagtacaa aaagcagggg cccagcccca gctgttggct acatgagtat ttagaggaag      8460
taaggtagca ggcagtccag ccctgatgtg gagacacatg ggattttgga aatcagcttc      8520
tggaggaatg catgtcacag gcgggacttt cttcagagag tggtgcagcg ccagacattt      8580
tgcacataag gcaccaaaca gcccaggact gccgagactc tggccgcccg aaggagcctg      8640
ctttggtact atggaacttt tcttagggga cacgtcctcc tttcacagct tctaaggtgt      8700
```

| | |
|---|---:|
| ccagtgcatt gggatggttt tccaggcaag gcactcggcc aatccgcatc tcagccctct | 8760 |
| cagggagcag tcttccatca tgctgaattt tgtcttccag gagctgcccc tatggggcgg | 8820 |
| ggccgcaggg ccagccttgt ttctctaaca acaaacaaa caaacagcct tgtttctcta | 8880 |
| gtcacatcat gtgtatacaa ggaagccagg aatacaggtt tcttgatga tttgggtttt | 8940 |
| aattttgttt ttattgcacc tgacaaaata cagttatctg atggtccctc aattatgtta | 9000 |
| ttttaataaa ataaattaaa tttaggtgta atggctggct gttacctcct tttaaagtaa | 9060 |
| ttctgagctc acaacttgaa tgccccattt gttcaccctc ttcaggagca gaattcaaga | 9120 |
| acaggaaatg tgcccagagc ctaggctggg aatgaatttg taatttaacc tttgtactct | 9180 |
| ttgtaaacct ctactgaaga gtt | 9203 |

<210> SEQ ID NO 6
<211> LENGTH: 12419
<212> TYPE: DNA
<213> ORGANISM: Homo sapiens

<400> SEQUENCE: 6

| | |
|---|---:|
| tccacggctg gtacctgtgt cgggtgggtg gccaggcgcg ggcctcgccc cccagccccc | 60 |
| tcgccagggc tagcccggct gcgcggcgcc cggagggggc cgggccgtcc ggtggggccg | 120 |
| cggccctgtt ccgcgctgcg agctcgccct ctcgcggctc cctggcccgg ccgccgccgc | 180 |
| ccctctcccc gcccagaggc gcccggggg caccatgcag gcgcagcagc tgccctacga | 240 |
| gttttcagc gaagagaacg cgcccaagtg gcggggacta ctggtgcctg cgctgaaaaa | 300 |
| ggtgaggagc acgcgggacc ccgcttcccg gccgcagccc ccagcgcgg gcgctgggga | 360 |
| agggctgggg aggcggggcg cgcgcagggc cgtctttctt cccggtctcg ccgcgtctcc | 420 |
| aaaaggacgg cgcacacgga gaggcccccc tcatacggct ggctctcggt gttgacatcc | 480 |
| attggccagg gtggtctcaa actcctgacc tcaggtgatc tgcccgcctt ggcctcccag | 540 |
| agtgctggca ttacaggcat gagccaccgt gcccggccac aaacccacat tttttaaagt | 600 |
| tttaaaaatt tgtttaatga tatggaaccc acattttaat tactttgctt tttgttttata | 660 |
| ggtccagggg caagttcatc ctactctcga gtctaatgat gatgctcttc agtatgttga | 720 |
| agaattaatt ttgcaattat taaatatgct atgccaagct cagccccgaa gtgcttcaga | 780 |
| tgtagaggta tgacaaatgt tgtcttgtat ttactttata tctaatttgt gtgttggttg | 840 |
| taatgtcagt gaacagggaa agaatttgct ctctctatat atatggtata taagaaaatg | 900 |
| aagcctggat ttaactcttt acaggttgag tatcccttat ccagaatgct gggaacaga | 960 |
| agtgtttatt aaggaactaa tacattgaca attactgttt tctcttagct tcatatgttt | 1020 |
| gtaatgtaaa ttataccaca tgtgaaaagc tctacttttg gtattctttg attttaaaag | 1080 |
| taaatttttaa gtgaagagca ctatttaata tattttttgc ttagttgtta ttttcctatt | 1140 |
| ttccaaggaa cgtgttcaaa aaagtttccc tcatccaatt gataaatggg caatagctga | 1200 |
| tgcccaatca gctattgaaa agaggaagcg aagaaccct ttatctctcc cagtagaaaa | 1260 |
| aattcatcct ttattaaagg taatgctgaa ctactgcctt cttgcctttt aagggaaaaa | 1320 |
| taaaacccac cattttttata caataagaat atattttatg gataattgag tcaacttaag | 1380 |
| agtaaaattc tctcattcta gttttccag agatttatgt ggtgagaagg gatgctatga | 1440 |
| taataagaaa atataaactt tttcaatagt aatacatata ttattcattg ttgaaccact | 1500 |
| tacaattaaa tgttgttggt aagcacaggc ctcaggaaaa aaagtgtaag ttaaggtgca | 1560 |
| aatatgttttt ttatttttaa tcagtgtgtt aaatgtacag tatatgatgt ttaaacatgc | 1620 |

```
ttttcttttta attttgcagg aggtcctagg ttataaaatt gaccaccagg tttctgttta    1680
catagtagca gtcttagaat acatttctgc agacatttta aagctggttg ggaattatgt    1740
aagaaatata cggcattatg aaattacaaa acaagatatt aaagtggcaa tgtgtgctga    1800
caaggtagga aactgagctt ttctattttt ttcttaagtt tctttttatg acttattaga    1860
tgctaacgta ctattcatat agaataaaat tgtattatgt gttggggaat atctccagta    1920
acctaatagt agggattcaa gataccactt tatagaaata agacattaga tatataatat    1980
taaatgttga attctgtttt agagaagctg tggagggatg ctggcaatat atccaagaag    2040
agaaatttgt ttgtctgctt ttttatcatt taagaacttt attcagagaa cttagagcat    2100
ttcacatcaa attctacgaa agcttcatat tttattatac tttttttatat ctctgactgt   2160
ataggtattg atggatatgt ttcatcaaga tgtagaagat attaatatat tatctttaac    2220
tgacgaagag ccttccacct caggagaaca aacttactat gatttggtaa aagcatttat    2280
ggcagaaatt cgacaatata aagggaact aaatctaatt ataaaagttt ttagagagcc     2340
ctttgtctcc aattcaaaat tgtttcagc taatgtaagt atcattgtat atatgcctct     2400
cattgaatgt gttgtgaaat ttgcatgacc acttcaaatt tgaagttgta cagttcatca    2460
ttactaattt gttaattttt ttaagttgtg ggacttaatt catgatcaca aagttttaca    2520
acagtttcaa gagatttaac attagaaatt aagacactga cctagagaaa tgtatttgca    2580
aattgtacac ctttgcagaa ggaattcttg aattgtcctt tattcatatt tctaagtcat    2640
taaaatttt cactgtgtct gacatgttaa attttgtgat tataaaatga cttattggct     2700
caaaatttgt ttaatattat aataatacag cctcactgaa ttaatgtgtt ttcccccaaa    2760
caggatgtag aaaatatatt tagtcgcata gtagatatac atgaacttag tgtaaagtta    2820
ctgggccata tagaagatac agtagaaatg acagatgaag gcagtcccca tccactagta    2880
ggaagctgct ttgaagactt agcagaggta agtacttcaa ttatatacccc gaaaagtctg   2940
cataaaagcc tacatttaca ttaaaattga gagtcttact tctttccagc taaagtcata    3000
gatactaatt gttgactatt tatctgttat tgctcctttt tcatagggtc attgtcaaca    3060
tatgtttctg ttatcttagc aaacagatct cttacttgag aatattggga tctcttctat    3120
taaaattata attagtagtc atataatttt tgcttagaga ctttcaaaga catacataat    3180
tgtgctcgca tagtcgtgcc ccataattaa atctttctgt gtttgtaatg gtaaattatt    3240
tatgttttac cttctttatt ttctaaggaa ctggcatttg atccatatga atcgtatgct    3300
cgagatattt tgcgacctgg ttttcatgat cgtttcctta gtcagttatc aaagcctggg    3360
gcagcacttt atttgcaggt atagtaattt ttaaatgaag atgtacaatg tctgaaaagt    3420
aaacttaaaa aaaaaattaa atcacttttt tttccagtca ataggcgaag gtttcaaaga    3480
agctgttcaa tatgttttac ccaggctgct tctggcccct gtttaccact gtctccatta    3540
ctttgaactt tgaaggtttt gatccatatg aatcgtatgc tcgagatatt ttgcgacctg    3600
gttttcatga tcgtttcctt agtcagttat caaagcctgg ggcagcactt tatttgcagg    3660
tatagtaattt tttaaatgaa gatgtacaat gtctgaaaag taaacttaaa aaaaaaatta   3720
aatcactttt ttttccagtc aataggcgaa ggtttcaaag aagctgttca atatgtttta    3780
cccaggctgc ttctggcccc tgtttaccac tgtctccatt actttgaact tttgaaggta   3840
agaaaactct ttattgttat ttgtaacata ttcaagtgtg aattttttt tttgctactt     3900
catttgtaaa ttattgtgtg agtaccctgc acattagtgt gtttctgttt tctttttcca    3960
gtcaagaagc aaatggaaat cagtctgcaa aagagtagca tattttctcg tcttagtctt    4020
```

-continued

```
aacactgcta atcttggtct tttaatgtag aaaacttggt tgtgtattaa tagtaacaca      4080
caagaaaaac acttttaaaa agaatatttg atgacacatt taaaatttt attgtgacag       4140 ttgaataaat gttattttta tccttaaatg agtttattat tattttatcc aaaaatgtac      4200
tactggttca gatttgtcat tttggcttta cagcagttag aagaaaaaag tgaagatcaa      4260
gaagacaagg aatgtttaaa acaagcaata acagctttgc ttaatgttca gagtggtatg     4320
gaaaaaatat gttctaaaag tcttgcaaaa cgaagactga ggtgaatatt tttacttttt     4380
aaaatatcct tttttccctg aatattgtgg tgtaaattca gggatcccag ttcctcctc       4440 aagtaaacaa tgaagaaaat agttttagtg acaagcctgg tcttttagag gaagtgacat      4500
caaagccaag agaattgtta ttgtttgaaa aacctttcat aatttctagg ttgctttaat      4560
tttcaaaatt gtgtaatttt gtaattctaa tctatttggg gaattagtga ataccttctc     4620
agtgagactt gtaaaaatct acttttacac tttcccttac ttacatgagc tctaggtttt     4680
ctgtcatcta tgtactaata atgtcttttt ctttattcca gtgaatctgc atgtcggttt     4740
tatagtcagc aaatgaaggg gaaacaacta gcaatcaaga agatgaacga gattcagaag     4800
aatattgatg gttgggaggg aaaagacatt ggacagtgtt gtaatgaatt tataatggaa     4860
ggaactctta cacgtgtagg agccaaacat gagagacaca tatttctctt tgatggctta     4920
atgatttgct gtaaatcaaa tcatgggcag ccaagacttc ctggtgctag caatgcagaa     4980
tatcgtctta aagaaaagtt tttatgcga aaggtacaaa ttaatgataa agatgacacc      5040
aatgaataca agcatgcttt tgaaataatt ttaaaagatg aaaatagtgt tatatttctct    5100 gccaagtcag ctgaagagaa aaacaattgg atggcagcat tgatatcttt acagtaccgg     5160
agtacactgg aaaggatgct tgatgtaaca atgctacagg aagagaaaga ggagcagatg     5220
aggctgccta gtgctgatgt ttatagattt gcagagcctg actctgaaga gaatattata     5280
tttgaagaga acatgcagcc caaggctgga attccaatta tcaaagcagg aactgttatt     5340
aaacttatag agaggcttac gtaccatatg tacgcaggta agaattatgc agttgcctgt     5400 cactttttgtt ttcctgcttc aaactgattt tctttcctgc atgggtttat tgtgcctaaa    5460
atagaaaaga aactaacaac caaagacctc ttttctttga ctaaaaatac cccacttat     5520 atttctttgg aatgttttac ttttctact acacttacac cactaattta ggaggcacta     5580
agctagcagt gcattaccaa gtccaaagcc ttcacttggg caaaacattt tggaactttt    5640
aaacttgact atttgatcta ttttgaaaat gtacataaca gttttaatca ttttgaatca    5700
tagagtttaa taagatattt tcctttttc ttccttagatc ccaattttgt tcggacattt    5760
cttacaacat acagatcctt ttgcaaacct caagaactac tgagtcttat aatagaaagg    5820
tctgtccatt taaaaatat ttaaattcat tatttttgt taaaaagag attgagctaa      5880 gatccttttc agaaatgtta gatgagcttt aaaatatact tcacaagcac ttttcaata     5940 aataaaatct cttagatgaa catttatttt ataataatgt tagctttat tatttcaata    6000 ataatttat tagcctttaa tactatagga gtctcacttg tttacactga tatgcatatc     6060
ttcagtaatt ttttacagta ttctcttgat tttgctgact ggtgaaaacg tttgtggttt     6120
tctatttgta taactcgata taattagtct tttcattaat ttgttctatt ttatgttagg    6180
tttgaaattc cagagcctga gccaacagaa gctgatcgca tagctataga gaatggagat     6240
caacccttga gtgcagaact gaaaagattt agaaaagaat atatacagcc tgtgcaactg    6300
cggtaagcat taaataaatg aagtaaataa gtctttatca aactttcgtt tcaatgttga    6360
agtatataag gaccttcccc aaacaaggag aggggtgaca ataaaattag taaattaaat    6420
```

```
ttactaatta gagcagttat cagaaattat agtataagcc ttaacataga attttggaag   6480
tgaattagag cagttatcag aaattatagt ataagcctta acatagaatt ttggaagtgt   6540
taagcacact gataagatta atttggtaag agttactgca ttttcatttg tattgtactg   6600
tgcattgtga taaacattta tgtttgattc ccatgtaatt caattctgtg ttaatgccat   6660
agagtattaa atgtatgtcg gcactgggta gagcaccact tctatgattt tgaaagagat   6720
gcatatcttt tgcaacgaat ggaagaattt attggaacag taagaggtat gttttttttt   6780
ttaggtgcct agttttatat gtaataaaag taccaacacg gtgactatca attgatgtca   6840
ttggggctca gtaatgtaag atgtttataa tagtaccagc ataaccattt caaaaagtta   6900 aaaatttca tcaaatagca tttagacctg caaatggctc aagtcaagat taggattggg   6960
gaccgggaaa tggaaaagga gaacttgcat ttttcatttt gatcatttga actttttata   7020
gcaaagatac attcaggtgt catccgtgtg actttaaacc attttttaaaa tataaaatat   7080 taaataaaga atatttaaat gttatttaaa atataatgta ttgcaggtaa agcaatgaaa   7140
aaatgggttg aatccatcac taaaataatc caaaggaaaa aaattgcaag agacaatgga   7200
ccaggtcata atattacatt tcagagttca cctcccacag ttgagtggca tataagcaga   7260
cctgggcaca tagagacttt tgacctgctc accttacacc caatagaaat tgctcgacaa   7320
ctcactttac ttgaatcaga tctataccgg tatgtaattt aacattcaag ttgaaaagtc   7380
atttcaaaag agttaacttt taaaatgaaa tactgatttc tgccttatag ggttttcata   7440
agacttaact gaaatattac atgaagtgtc tagtaataag gccaggcagg cagttcctgt   7500
tcttttactc ccctggtccc tctagctgac cataaggaaa tatgcataat tacactttt   7560 tgttatacct tgttttcaca gacctttctg ttggtataag aggaaagttc atatgagagt   7620
ttagttttta tttgtctcct ttacttaata aaacaatgtc tatattagag aaaaaagtgt   7680
catgtagaat tatgtattga tgattttaga gctgtacagc catcagaatt agttggaagt   7740
gtgtggacaa aagaagacaa agaaattaac tctcctaatc ttctgaaaat gattcgacat   7800
accaccaacc tcactctgtg gtttgagaag taagtattcc tagcattctt atattttata   7860
gctgtcagct atgttatgaa tttcaatgca attttttgt ttgttttttt tgagacggag   7920
ttttgctctg tcacataggc tggagtgcag tggcacatcg gcccactgaa acctccacct   7980
cccaggctca gcgatcctc ccacctcagg tatgcctgac tggaggcact gccttccttc   8040
tatcagtcac cctgaatgtg tcttctctat agtagttata ctatcgccac ccccctactc   8100
tctacattat tttatttact aaattcttta agctataact ttattggaaa aactctaaaa   8160
cctttagttc actttttttt tattcccaga tgtattgtag aaactgaaaa tttagaagaa   8220
agagtagctg tggtgagtcg aattattgag attctacaag tctttcaaga gttgaacaac   8280
tttaatggtg tccttgaggt tgtcagtgct atgaattcat cacctgttta cagactagac   8340
cacacatttg aggtaggttt ctacatgtgt ttttaaaatg aactttcatt ccctattaga   8400
aaaattagat ttttaacaat tattatctttt aattttttaaa tgtctcatt gtcttttcag   8460 tagtagatta aaagactgaa ttatctaagt tttgtaatga attggttgct ttttaaaatt   8520
taagcattcc taactttaag tttatactga ggtctatgaa gataatttat ttgaagcaat   8580
atttgaagca atgttacagt cataaaatca aattgatact gttgtatttg ggcgtttctg   8640
ttagcctagt attttttttg acaagacctt tgattccttt tgtaaactta cgcctatttt   8700
ttttccttat agcaaatacc aagtcgccag aagaaaattt tagaagaagc tcatgaattg   8760
agtgaagatc actataagaa atatttggca aaactcaggt ctattaatcc accatgtgtg   8820
```

```
cctttctttg gtaagtattt ctttctgaat ttttattgca tttctggata aaacaaaaca    8880
ctcatttcat taaatgactg aataattaca tgtgtaatat gccagcagaa aatacttgtt    8940
tgatcaatat ttagcacctg aagcccttta gaattttttct cattaagact taaggtgaag   9000
tctaatatac ttaagtcttt cacagatact ttctcttaag ctgctgtttt catatcatgg    9060
aaatctgagc cttggttctt ttgttttggc aactgagatg gtacagtgta atatacccac    9120
aattaatgaa acagaaaaaa acttgcattt tccttcttta tccttgaaat cattccatta    9180
tatcttctag gaatttatct cactaatatc ttgaaaacag aagaaggcaa ccctgaggtc    9240
ctaaaaagac atggaaaaga gcttataaac tttagcaaaa ggaggaaagt agcagaaata    9300
acaggagaga tccagcagta ccaaaatcag ccttactgtt tacgagtaga atcagatatc    9360
aaagtaagtt gaattattta aagattcata cttctgatta agtttctaaa ctacttaata    9420
aaaggcaggt ttattttata ggggagaaaa agtaaaataa accttaaaag aataattca    9480 aatttacttg tattaaatgt tttcttaact ttccatgaat ttcaaactga atttataatt    9540
ttgttaagtt tctaaactac ttaataaaag gcaggtttat tttataggggg agaaaaagta   9600 aaataaacct taaagaaat aattcaaatt tacttgtatt aaatgttttc ttaacttttcc    9660 atgaatttca aactgaattt ataattttga atattaataa ttttttcttt gcatttattt    9720
tagaggttct ttgaaaactt gaatccgatg ggaaatagca tggagaagga atttacagat    9780
tatcttttca acaaatccct agaaatagaa ccacgaaacc ctaagcctct cccaagattt    9840
gtaagcattt gtatatttgt ctggtgatgt cattactacc atatgtgtta tatagttttc    9900
cataaaggta ttcagggatg aagtatacat gtgatagtta aaagtaatga aaaagtactt    9960
aataattatg tccaggaata tcccacttcc ttccaaataa atgaatgtta gtattaattt   10020
ggctttagca aaatagaatg ttaatgcttt aaatgttcta ctttttatttg aataattatg   10080 tccttattag tgatttatga ttttcctgta tattagctga attttaccag gcacatatag   10140
aaaaactttc ctttctacta cagtgtttaa agtattgtgt ttcttttgat atgtctacag    10200
ccaaaaaaat atagctatcc cctaaaatct cctggtgttc gtccatcaaa cccaagacca    10260
ggtaccatga ggcatcccac acctctgcag caggagccaa ggaaaattag ttatagtagg   10320
atccctgaaa gtgaaacaga aagtacagca tctgcaccaa attctccaag aacaccgtta   10380
acacctccgc ctgcttctgg tgcttccagt accacagatg tttgcagtgt atttgattcc   10440
gatcattcga gcccttttca ctcaagtagg tgcaaaaatt ctaagtgcat taaggtattt   10500
gttagtacta tacatgctag aggtaaaaaa gaatctctgt tatttttttg tatgtgtgaa    10560
cttgtagtta agtcaaatgc catttcaaaa gataatatta taaaatata agacaaattc    10620 taaactccac caacttgaaa tttctatgaa atcaagtaaa gctaaaagga atcttaaatt    10680
cccaatatga tatcatttt tcttctcaa agtaagtag taatgaggtt ttactataaa       10740
ctgttacagc attcttaaa acgacaatga caataacatt ttcatcataa tacaaatttt    10800
tgcagatgag ttgaatatat caatgaaaga aaaaaatcta ctttttcttg tttcctttca    10860
caggcaatga taccgtcttt atccaagtta ctctgcccca tggcccaagt tagtatattt    10920
ggtttaagac tcataattct tgctttggct ttaaaaatca aaccaagtgt aacctttcct    10980
gctaaaactc ttcttgggtc tggcagcatt ggtaccttgc ttgcaacatc ctagaagtga    11040
ggccttcact tgtgctatct ttagatcata agtgatttgc ttaaattttg catgcttta    11100 tggcagtttg cttaatgaa atactattcg gtattgggtt tattgaacagc ttttggtatt    11160 tctacacatt acttttaatt ataagcaatt tccagctaag acttttcaag gtaaataaat   11220
```

```
gaaataaaat tcctgtggac ttttcttaa aatttaaca tcccacagga tctgcttctg    11280
tatcatctat aagtttaacc aaaggcactg atgaagtgcc tgtccctcct cctgttcctc    11340
cacgaagacg accagaatct gccccagcag aatcttcacc atctaaggta aagtaagaaa    11400
tcttgttgtg tagaaattgg aatcattaca gttcattata ataaacggct gtctagttta    11460
gttctcacta ggataagtta acatttcaga gtatacaggc ttaatagttt aaacaaggat    11520
tacatataga tttagcatgc agtaatgttt ctttcttctg aaggtagagg cattgtctca    11580 aaaaaaaaa ttttttttta attaaaaaga aaacatatgg caaaactccc tgttccacac    11640
ttagcatcct gccaatagca tgtttgaaaa ccccaactta attcttatag tcatgatact    11700
tcataaattt attaataaat gtgtattta ttcttttcat ttgttagatt atgtctaagc    11760
atttggacag tcccccagcc attcctccta ggcaacccac atcaaaagcc tattcaccac    11820
gatattcaat atcagaccgg acctctatct cagaccctcc tgaaagccct cccttattac    11880
caccacgaga acctgtgagg acacctgatg ttttctcaag ctcaccacta catctccaac    11940
ctcccctttt gggcaaaaaa agtgaccatg gcaatgcctt cttcccaaac agcccttccc    12000
cctttacacc acctcctcct caaacacctt ctcctcacgg cacaagaagg catctgccat    12060
caccaccatt gacacaagaa gtggaccttc attccattgc tgggccgcct gttcctccac    12120
gacaaagcac ttctcaacat atccctaaac tccctccaaa aacttacaaa agggagcaca    12180
cacacccatc catgcacaga gatggaccac cactgttgga gaatgcccat tcttcctgag    12240
ttcctctgta ctgggatgta tattttccta gccccaaatc cattgctggc aatggatgca    12300
ctgaatgtgc cagcactgag gagttaaaat gagaactcca aacactaacg actcttcttc    12360
aagatgcagt ataagacaat gaattttaac ctagatgtaa ttatacaatg gaaatggta    12419

<210> SEQ ID NO 7
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
tccacggctg gtacctgtgt c                                                21

<210> SEQ ID NO 8
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
accgagagcc agccgtatga g                                                21

<210> SEQ ID NO 9
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
ggtggtctca aactcctgac c                                                21
```

```
<210> SEQ ID NO 10
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
acttctgttc ccaagcattc tgg                                            23

<210> SEQ ID NO 11
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
attataccac atgtgaaaag ctc                                            23

<210> SEQ ID NO 12
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
ttctcaccac ataaatctct gg                                             22

<210> SEQ ID NO 13
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
aaatgttgtt ggtaagcaca ggc                                            23

<210> SEQ ID NO 14
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
tccctactat taggttactg gag                                            23

<210> SEQ ID NO 15
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
aactttattc agagaactta gagc                                           24

<210> SEQ ID NO 16
<211> LENGTH: 22
```

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
ggtcatgcaa atttcacaac ac                                              22

<210> SEQ ID NO 17
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
cactgaccta gagaaatgta tttgc                                           25

<210> SEQ ID NO 18
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
tagctggaaa gaagtaagac tctc                                            24

<210> SEQ ID NO 19
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
aattgtgctc gcatagtcgt gc                                              22

<210> SEQ ID NO 20
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
ctaatgtgca gggtactcac ac                                              22

<210> SEQ ID NO 21
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
cttaacactg ctaatcttgg tc                                              22

<210> SEQ ID NO 22
<211> LENGTH: 22
<212> TYPE: DNA
<213> ORGANISM: Artificial Sequence
```

```
<220> FEATURE:
<223> OTHER INFORMATION: Description of Artificial Sequence: Synthetic
      primer

<400> SEQUENCE: 22
cttcattgtt tacttgagga gg                                               22

<210> SEQ ID NO 23
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
cactttccct tacttacatg agctc                                            25

<210> SEQ ID NO 24
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
ctgtaaagat atcaatgctg cca                                              23

<210> SEQ ID NO 25
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25
gatgacacca atgaatacaa gc                                               22

<210> SEQ ID NO 26
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26
catgcaggaa agaaaatcag t                                                21

<210> SEQ ID NO 27
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27
aagtccaaag ccttctactt gg                                               22

<210> SEQ ID NO 28
<211> LENGTH: 24
<212> TYPE: DNA
<213> ORGANISM: Artificial Sequence
<220> FEATURE:
<223> OTHER INFORMATION: Description of Artificial Sequence: Synthetic
```

-continued

```
<400> SEQUENCE: 28
tgaaaaggat cttagctcaa tctc                                           24

<210> SEQ ID NO 29
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 29
gtttacactg atatgcatat cttcag                                         26

<210> SEQ ID NO 30
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 30
ctaattttat tgtcacccct ctcc                                           24

<210> SEQ ID NO 31
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 31
ctgataagat taatttggta agag                                           24

<210> SEQ ID NO 32
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 32
tataaacatc ttacattact gagc                                           24

<210> SEQ ID NO 33
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 33
caaagataca ttcaggtgtc atcc                                           24

<210> SEQ ID NO 34
<211> LENGTH: 25
<212> TYPE: DNA
<213> ORGANISM: Artificial Sequence
<220> FEATURE:
<223> OTHER INFORMATION: Description of Artificial Sequence: Synthetic
      primer
```

-continued

<400> SEQUENCE: 34
gtcttatgaa aaccctataa ggcag                                    25

<210> SEQ ID NO 35
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 35
tataagagga aagttcatat gagag                                    25

<210> SEQ ID NO 36
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 36
gaaattcata acatagctga cagc                                     24

<210> SEQ ID NO 37
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 37
gccttccttc tatcagtcac cc                                       22

<210> SEQ ID NO 38
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 38
tagcttaggc tgggacctgt g                                        21

<210> SEQ ID NO 39
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 39
tgtatttggg cgtttctgtt agcc                                     24

<210> SEQ ID NO 40
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 40
gatcaaacaa gtattttctg ctggc                                              25

<210> SEQ ID NO 41
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 41
gatggtacag tgtaatatac ccac                                               24

<210> SEQ ID NO 42
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 42
cttctccatg ctatttccca tcg                                                23

<210> SEQ ID NO 43
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 43
ccaaaatcag ccttactgtt tacg                                               24

<210> SEQ ID NO 44
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 44
cacatatggt agtaatgaca tcacc                                              25

<210> SEQ ID NO 45
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 45
tatattagct gaattttacc aggc                                               24

<210> SEQ ID NO 46
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 46
acttaactac aagttcacac atac                                               24

```
<210> SEQ ID NO 47
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 47
atgaaatcaa gtaaagctaa aagg                                            24

<210> SEQ ID NO 48
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 48
ctaaagatag cacaagtgaa gg                                              22

<210> SEQ ID NO 49
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 49
attggtttat tgaacagctt ttgg                                            24

<210> SEQ ID NO 50
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 50
agtgagaact aaactagaca gc                                              22

<210> SEQ ID NO 51
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 51
acacttagca tcctgccaat agc                                             23

<210> SEQ ID NO 52
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 52
ctgtttggga agaaggcatt gc                                              22

<210> SEQ ID NO 53
```

```
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 53
tcaagctcac cactacatct cc                                              22

<210> SEQ ID NO 54
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 54
gttctcattt taactcctca gtgc                                            24

<210> SEQ ID NO 55
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 55
tctttgctga tgaatgcagg ag                                              22

<210> SEQ ID NO 56
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 56
aatgacaatg aatattttgc ctgtc                                           25

<210> SEQ ID NO 57
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 57
catcacaagc aatacagact gg                                              22

<210> SEQ ID NO 58
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 58 aactttcaa gagaatgtcc aagc                                             24

<210> SEQ ID NO 59
<211> LENGTH: 21
<212> TYPE: DNA
```

<213> ORGANISM: Artificial Sequence
<220> FEATURE:
<223> OTHER INFORMATION: Description of Artificial Sequence: Synthetic
      primer

<400> SEQUENCE: 59
aacttgctgt gtggccttga g                                               21

<210> SEQ ID NO 60
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 60
tgagaaatct ctgttatgcc tgg                                             23

<210> SEQ ID NO 61
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 61
gtacatgctg gaagtatgat tc                                              22

<210> SEQ ID NO 62
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 62
cctgtcagtc aaaatctaca ac                                              22

<210> SEQ ID NO 63
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 63
ctgtatgttt attggcaggt cag                                             23

<210> SEQ ID NO 64
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 64
cagtatcaag ttccacagaa gc                                              22

<210> SEQ ID NO 65
<211> LENGTH: 21
<212> TYPE: DNA
<213> ORGANISM: Artificial Sequence
<220> FEATURE:

<223> OTHER INFORMATION: Description of Artificial Sequence: Synthetic
      primer

<400> SEQUENCE: 65
ccagtatgaa agcctaagtg c                                              21

<210> SEQ ID NO 66
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 66
ctgaaataag tatcaacctc acc                                            23

<210> SEQ ID NO 67
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 67
atcttttgtg tgtaggagtt gacc                                           24

<210> SEQ ID NO 68
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 68
ttcttactga accctaattg gcag                                           24

<210> SEQ ID NO 69
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 69
catgggttga tcctttgatg c                                              21

<210> SEQ ID NO 70
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 70
cttgacttca caccaaagcc c                                              21

<210> SEQ ID NO 71
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

```
<400> SEQUENCE: 71
cactgtatct tcctcaaaac tag                                              23

<210> SEQ ID NO 72
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 72
cagtgagtcc taactgcctg c                                                21

<210> SEQ ID NO 73
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 73
gcttctcttt gctcagaatg c                                                21

<210> SEQ ID NO 74
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 74
ctgatcctgg ttccaattta gg                                               22

<210> SEQ ID NO 75
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 75
gtggctttac ttcttagctg tag                                              23

<210> SEQ ID NO 76
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 76
accgagagcc acttgtgata g                                                21

<210> SEQ ID NO 77
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 77
```

```
gaccattctt ttgaaaccag ag                                              22
```

<210> SEQ ID NO 78
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 78

```
gcattccttt tgccctatac c                                               21
```

<210> SEQ ID NO 79
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 79

```
ctagatgtct gtgaggcctg tc                                              22
```

<210> SEQ ID NO 80
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 80

```
caagtcctaa ccctctagct gc                                              22
```

<210> SEQ ID NO 81
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 81

```
ctaagcagct agagggttag gac                                             23
```

<210> SEQ ID NO 82
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 82

```
ctcccacctt atattgccat c                                               21
```

<210> SEQ ID NO 83
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 83

```
gatggcaata taaggtggga g                                               21
```

<210> SEQ ID NO 84
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 84
tccttagcag cagcttctct g                                              21

<210> SEQ ID NO 85
<211> LENGTH: 481
<212> TYPE: DNA
<213> ORGANISM: Homo sapiens

<400> SEQUENCE: 85
tccacggctg gtacctgtgt cgggtgggtg gccaggcgcg ggcctcgccc cccagccccc     60
tcgccagggc tagcccggct gcgcggcgcc cggaggggc cgggccgtcc ggtggggccg    120
cggccctgtt ccgcgctgcg agctcgccct ctcgcggctc cctggcccgg ccgccgccgc   180
ccctctcccc gcccagaggc gccccggggg caccatgcag gcgcagcagc tgccctacga   240 gttttttcagc gaagagaacg cgcccaagtg gcggggacta ctggtgcctg cgctgaaaaa   300
ggtgaggagc acgcgggacc ccgcttcccg gccgcagccc ccagcgcgg gcgctgggga   360 agggctgggg aggcggggcg cgcgcagggc cgtctttctt cccggtctcg ccgcgtctcc   420
aaaaggacgg cgcacacgga gaggccccccc tcatacggct ggctctcggt gttgacatcc   480
a                                                                   481

<210> SEQ ID NO 86
<211> LENGTH: 486
<212> TYPE: DNA
<213> ORGANISM: Homo sapiens

<400> SEQUENCE: 86
ttggccaggg tggtctcaaa ctcctgacct caggtgatct gcccgccttg gcctcccaga     60
gtgctggcat tacaggcatg agccaccgtg cccggccaca aacccacatt ttttaaagtt    120
ttaaaatttt gtttaatgat atggaaccca cattttaatt actttgcttt ttgtttatag    180
gtccaggggc aagttcatcc tactctcgag tctaatgatg atgctcttca gtatgttgaa    240
gaattaattt tgcaattatt aaatatgcta tgccaagctc agccccgaag tgcttcagat    300
gtagaggtat gacaaatgtt gtcttgtatt tactttatat ctaatttgtg tgttggttgt    360
aatgtcagtg aacagggaaa gaatttgctc tctctatata tatggtatat aagaaaatga    420
agcctggatt taactctttta caggttgagt atcccttatc cagaatgctt gggaacagaa   480
gtgttt                                                              486

<210> SEQ ID NO 87
<211> LENGTH: 492
<212> TYPE: DNA
<213> ORGANISM: Homo sapiens

<400> SEQUENCE: 87
attaaggaac taatacattg acaattactg ttttctctta gcttcatatg tttgtaatgt     60
aaattatacc acatgtgaaa agctctactt tggtattct ttgattttaa agtaaatttt    120
taagtgaaga gcactatttta atatattttt tgcttagttg ttattttcct attttccaag   180

```
gaacgtgttc aaaaaagttt ccctcatcca attgataaat gggcaatagc tgatgcccaa    240
tcagctattg aaaagaggaa gcgaagaaac cctttatctc tcccagtaga aaaaattcat    300
cctttattaa aggtaatgct gaactactgc cttcttgcct tttaagggaa aaataaaacc    360
caccattttt atacaataag aatatatttt atggataatt gagtcaactt aagagtaaaa    420
ttctctcatt ctaagttttc cagagattta tgtggtgaga agggatgcta tgataataag    480
aaaatataaa ct                                                        492
```

```
<210> SEQ ID NO 88
<211> LENGTH: 525
<212> TYPE: DNA
<213> ORGANISM: Homo sapiens

<400> SEQUENCE: 88
ttttcaatag taatacatat attattcatt gttgaaccac ttacaattaa atgttgttgg     60
taagcacagg cctcaggaaa aaagtgtaa gttaaggtgc aaatatgttt tttatttta    120 atcagtgtgt taaatgtaca gtatatgatg tttaaacatg ctttctttt aattttgcag    180 gaggtcctag gttataaaat tgaccaccag gtttctgttt acatagtagc agtcttagaa    240
tacatttctg cagacatttt aaagctggtt gggaattatg taagaaatat acggcattat    300
gaaattacaa acaagatat taagtgca atgtgtgctg acaaggtagg aaactgagct    360
tttctatttt tttcttaagt ttctttttat gacttattag atgctaacgt actattcata    420
tagaataaaa ttgtattatg tgttggggaa tatctccagt aacctaatag tagggattca    480
agataccact ttatagaaat aagacattag atatataata ttaaa                   525
```

```
<210> SEQ ID NO 89
<211> LENGTH: 570
<212> TYPE: DNA
<213> ORGANISM: Homo sapiens

<400> SEQUENCE: 89
tgttgaattc tgttttagag aagctgtgga gggatgctgg caatatatcc aagaagagaa     60
atttgtttgt ctgctttttt atcatttaag aactttattc agagaactta gagcatttca    120
catcaaattc tacgaaagct tcatatttta ttatacttttt ttatatctct gactgtatag    180
gtattgatgg atatgtttca tcaagatgta aagatatta atatattatc tttaactgac    240
gaagagcctt ccacctcagg agaacaaact tactatgatt tggtaaaagc atttatggca    300
gaaattcgac aatatataag ggaactaaat ctaattataa aagttttag agagcccttt    360 gtctccaatt caaaattgtt ttcagctaat gtaagtatca ttgtatatat gcctctcatt    420
gaatgtgttg tgaaatttgc atgaccactt caaatttgaa gttgtacagt tcatcattac    480
taatttgtta attttttaa gttgtgggac ttaattcatg atcacaaagt tttacaacag    540
tttcaagaga tttaacatta gaaattaaga                                    570
```

```
<210> SEQ ID NO 90
<211> LENGTH: 533
<212> TYPE: DNA
<213> ORGANISM: Homo sapiens

<400> SEQUENCE: 90
cactgaccta gagaaatgta tttgcaaatt gtacaccttt gcagaaggaa ttcttgaatt     60
gtcctttatt catatttcta agtcattaaa atttttcact gtgtctgaca tgttaaattt    120
tgtgattata aaatgactta ttggctcaaa atttgtttaa tattataata atacagcctc    180
```

| | |
|---|---|
| actgaattaa tgtgttttcc cccaaacagg atgtagaaaa tatatttagt cgcatagtag | 240 |
| atatacatga acttagtgta aagttactgg gccatataga agatacagta gaaatgacag | 300 |
| atgaaggcag tccccatcca ctagtaggaa gctgctttga agacttagca gaggtaagta | 360 |
| cttcaattat atacccgaaa agtctgcata aaagcctaca tttacattaa aattgagagt | 420 |
| cttacttctt tccagctaaa gtcatagata ctaattgttg actatttatc tgttattgct | 480 |
| cctttttcat agggtcattg tcaacatatg tttctgttat cttagcaaac aga | 533 |

<210> SEQ ID NO 91
<211> LENGTH: 471
<212> TYPE: DNA
<213> ORGANISM: Homo sapiens

<400> SEQUENCE: 91

| | |
|---|---|
| tctcttactt gagaatattg ggatctcttc tattaaaatt ataattagta gtcatataat | 60 |
| ttttgcttag agactttcaa agacatacat aattgtgctc gcatagtcgt gccccataat | 120 |
| taaatctttc tgtgtttgta atggtaaatt atttatgttt taccttcttt attttctaag | 180 |
| gaactggcat ttgatccata tgaatcgtat gctcgagata ttttgcgacc tggttttcat | 240 |
| gatcgtttcc ttagtcagtt atcaaagcct ggggcagcac tttatttgca ggtatagtaa | 300 |
| ttttttaaatg aagatgtaca atgtctgaaa agtaaactta aaaaaaaaat taaatcactt | 360 |
| tttttttccag tcaataggcg aaggtttcaa agaagctgtt caatatgttt tacccaggct | 420 |
| gcttctggcc cctgtttacc actgtctcca ttactttgaa cttttgaagg t | 471 |

<210> SEQ ID NO 92
<211> LENGTH: 459
<212> TYPE: DNA
<213> ORGANISM: Homo sapiens

<400> SEQUENCE: 92

| | |
|---|---|
| ttgatccata tgaatcgtat gctcgagata ttttgcgacc tggttttcat gatcgtttcc | 60 |
| ttagtcagtt atcaaagcct ggggcagcac tttatttgca ggtatagtaa ttttttaaatg | 120 |
| aagatgtaca atgtctgaaa agtaaactta aaaaaaaaat taaatcactt tttttttccag | 180 |
| tcaataggcg aaggtttcaa agaagctgtt caatatgttt tacccaggct gcttctggcc | 240 |
| cctgtttacc actgtctcca ttactttgaa cttttgaagg taagaaaact ctttattgtt | 300 |
| atttgtaaca tattcaagtg tgaatttttt tttttgctac ttcatttgta aattattgtg | 360 |
| tgagtacccct gcacattagt gtgttctgt tttctttttc cagtcaagaa gcaaatggaa | 420 |
| atcagtctgc aaaagagtag catattttct cgtcttagt | 459 |

<210> SEQ ID NO 93
<211> LENGTH: 524
<212> TYPE: DNA
<213> ORGANISM: Homo sapiens

<400> SEQUENCE: 93

| | |
|---|---|
| cttaacactg ctaatcttgg tcttttaatg tagaaaactt ggttgtgtat taatagtaac | 60 |
| acacaagaaa aacactttta aaaagaatat ttgatgacac atttaaaatt tttattgtga | 120 |
| cagttgaata aatgttattt ttatccttaa atgagtttat tattatttta tccaaaaatg | 180 |
| tactactggt tcagatttgt cattttggct ttacagcagt tagaagaaaa aagtgaagat | 240 |
| caagaagaca aggaatgttt aaaacaagca ataacagctt tgcttaatgt tcagagtggt | 300 |
| atggaaaaaa tatgttctaa aagtcttgca aaacgaagac tgaggtgaat atttttactt | 360 |

| | | | |
|---|---|---|---|
| tttaaaatat | ccttttttcc | ctgaatattg tggtgtaaat | tcagggatcc cagttccctc | 420 |
| ctcaagtaaa | caatgaagaa | aatagtttta gtgacaagcc | tggtctttta gaggaagtga | 480 |
| catcaaagcc | aagagaattg | ttattgtttg aaaaaccttt | cata | 524 |

<210> SEQ ID NO 94
<211> LENGTH: 1016
<212> TYPE: DNA
<213> ORGANISM: Homo sapiens

<400> SEQUENCE: 94

| | | | | |
|---|---|---|---|---|
| atttctaggt | tgctttaatt | ttcaaaattg | tgtaattttg taattctaat ctatttgggg | 60 |
| aattagtgaa | taccttctca | gtgagacttg | taaaaatcta cttttacact ttcccttact | 120 |
| tacatgagct | ctaggttttc | tgtcatctat | gtactaataa tgtcttttc tttattccag | 180 |
| tgaatctgca | tgtcggtttt | atagtcagca | aatgaagggg aaacaactag caatcaagaa | 240 |
| gatgaacgag | attcagaaga | atattgatgg | ttgggaggga aaagacattg acagtgttg | 300 |
| taatgaattt | ataatggaag | gaactcttac | acgtgtagga gccaaacatg agagacacat | 360 |
| atttctcttt | gatggcttaa | tgatttgctg | taaatcaaat catgggcagc caagacttcc | 420 |
| tggtgctagc | aatgcagaat | atcgtcttaa | agaaaagttt tttatgcgaa aggtacaaat | 480 |
| taatgataaa | gatgacacca | atgaatacaa | gcatgctttt gaataatttt taaaagatga | 540 |
| aaatagtgtt | atattttctg | ccaagtcagc | tgaagagaaa aacaattgga tggcagcatt | 600 |
| gatatcttta | cagtaccgga | gtacactgga | aaggatgctt gatgtaacaa tgctacagga | 660 |
| agagaaagag | gagcagatga | ggctgcctag | tgctgatgtt tatagatttg cagagcctga | 720 |
| ctctgaagag | aatattatat | ttgaagagaa | catgcagccc aaggctggaa ttccaattat | 780 |
| caaagcagga | actgttatta | aacttataga | gaggcttacg taccatatgt acgcaggtaa | 840 |
| gaattatgca | gttgcctgtc | acttttgttt | tcctgcttca aactgatttt ctttcctgca | 900 |
| tgggtttatt | gtgcctaaaa | tagaaaagaa | actaacaacc aaagacctct tttctttgac | 960 |
| taaaaatacc | ccactttata | tttctttgga | atgttttact ttttctacta cactta | 1016 |

<210> SEQ ID NO 95
<211> LENGTH: 442
<212> TYPE: DNA
<213> ORGANISM: Homo sapiens

<400> SEQUENCE: 95

| | | | | |
|---|---|---|---|---|
| caccactaat | ttaggaggca | ctaagctagc | agtgcattac caagtccaaa gccttctact | 60 |
| tggcaaaaca | ttttggaact | tttaaacttg | actatttgat ctattttgaa aatgtacata | 120 |
| acagttttaa | tcattttgaa | tcatagagtt | taataagata ttttccttt tcttccttag | 180 |
| atcccaattt | tgttcggaca | tttcttacaa | catacagatc cttttgcaaa cctcaagaac | 240 |
| tactgagtct | tataatagaa | aggtctgtcc | atttaaaaaa tatttaaatt cattatttt | 300 |
| tgttaaaaaa | gagattgagc | taagatcctt | ttcagaaatg ttagatgagc tttaaaatat | 360 |
| acttcacaag | cacttttca | ataaataaaa | tctcttagat gaacatttat tttataataa | 420 |
| tgttagcttt | tattatttca | at | | 442 |

<210> SEQ ID NO 96
<211> LENGTH: 483
<212> TYPE: DNA
<213> ORGANISM: Homo sapiens

<400> SEQUENCE: 96

```
aataatttta ttagccttta atactatagg agtctcactt gtttacactg atatgcatat    60
cttcagtaat ttttacagt attctcttga ttttgctgac tggtgaaaac gtttgtggtt   120
ttctatttgt ataactcgat ataattagtc ttttcattaa tttgttctat tttatgttag   180
gtttgaaatt ccagagcctg agccaacaga agctgatcgc atagctatag agaatggaga   240
tcaacccttg agtgcagaac tgaaaagatt tagaaaagaa tatatacagc ctgtgcaact   300
gcggtaagca ttaaataaat gaagtaaata agtctttatc aaactttcgt ttcaatgttg   360
aagtatataa ggacctttcc caaacaagga gaggggtgac aataaaatta gtaaattaaa   420
tttactaatt agagcagtta tcagaaatta tagtataagc cttaacatag aattttggaa   480
gtg                                                                 483
```

```
<210> SEQ ID NO 97
<211> LENGTH: 464
<212> TYPE: DNA
<213> ORGANISM: Homo sapiens

<400> SEQUENCE: 97
aattagagca gttatcagaa attatagtat aagccttaac atagaatttt ggaagtgtta    60
agcacactga taagattaat ttggtaagag ttactgcatt ttcatttgta ttgtactgtg   120
cattgtgata acatttatg tttgattccc atgtaattca attctgtgtt aatgccatag    180
agtattaaat gtatgtcggc actgggtaga gcaccacttc tatgattttg aaagagatgc   240
atatcttttg caacgaatgg aagaatttat tggaacagta agaggtatgt ttttttttt    300 aggtgcctag ttttatatgt aataaaagta ccaacacggt gactatcaat tgatgtcatt   360
ggggctcagt aatgtaagat gtttataata gtaccagcat aaccatttca aaaagttaaa   420
aattttcatc aaatagcatt tagacctgca aatggctcaa gtca                    464
```

```
<210> SEQ ID NO 98
<211> LENGTH: 583
<212> TYPE: DNA
<213> ORGANISM: Homo sapiens

<400> SEQUENCE: 98
agattaggat tggggaccgg gaaatggaaa aggagaactt gcatttttca ttttgatcat    60
ttgaactttt tatagcaaag atacattcag gtgtcatccg tgtgacttta aaccattttt   120
aaaatataaa atattaaata aagaatattt aaatgttatt taaaatataa tgtattgcag   180
gtaaagcaat gaaaaatgg gttgaatcca tcactaaaat aatccaaagg aaaaaaattg   240
caagagacaa tggaccaggt cataatatta catttcagag ttcacctccc acagttgagt   300
ggcatataag cagacctggg cacatagaga cttttgaccct gctcaccta cacccaatag   360 aaattgctcg acaactcact ttacttgaat cagatctata ccggtatgta atttaacatt   420
caagttgaaa agtcatttca aaagagttaa ctttaaaat gaaatactga tttctgcctt   480
atagggtttt cataagactt aactgaaata ttacatgaag tgtctagtaa taaggccagg   540
caggcagttc ctgttctttt actcccctgg tccctctagc tga                    583
```

```
<210> SEQ ID NO 99
<211> LENGTH: 480
<212> TYPE: DNA
<213> ORGANISM: Homo sapiens

<400> SEQUENCE: 99
ccataaggaa atatgcataa ttacactttt ttgttatacc ttgttttcac agacctttct    60
```

```
gttggtataa gaggaaagtt catatgagag tttagttttt atttgtctcc tttacttaat    120
aaaacaatgt ctatattaga gaaaaaagtg tcatgtagaa ttatgtattg atgattttag    180
agctgtacag ccatcagaat tagttggaag tgtgtggaca aaagaagaca aagaaattaa    240
ctctcctaat cttctgaaaa tgattcgaca taccaccaac ctcactctgt ggtttgagaa    300
gtaagtattc ctagcattct tatattttat agctgtcagc tatgttatga atttcaatgc    360 aattttttg tttgttttt ttgagacgga gttttgctct gtcacatagg ctggagtgca    420
gtggcacatc ggcccactga aacctccacc tcccaggctc aagcgatcct cccacctcag    480
```

```
<210> SEQ ID NO 100
<211> LENGTH: 523
<212> TYPE: DNA
<213> ORGANISM: Homo sapiens

<400> SEQUENCE: 100
gtatgcctga ctggaggcac tgccttcctt ctatcagtca ccctgaatgt gtcttctcta     60
tagtagttat actatcgcca ccccctact ctctacatta ttttatttac taaattcttt    120
aagctataac tttattggaa aaactctaaa acctttagtt cactttttt ttattcccag    180 atgtattgta gaaactgaaa atttagaaga aagagtagct gtggtgagtc gaattattga    240
gattctacaa gtcttttcaag agttgaacaa ctttaatggt gtccttgagg ttgtcagtgc    300
tatgaattca tcacctgttt acagactaga ccacacattt gaggtaggtt tctacatgtg    360
tttttaaaat gaactttcat tccctattag aaaaattaga ttttaacaa ttattatctt    420 taattttaa atgtctcatt tgtctttca gtagtagatt aaaagactga attatctaag    480
ttttgtaatg aattggttgc ttttaaaat ttaagcattc cta    523
```

```
<210> SEQ ID NO 101
<211> LENGTH: 478
<212> TYPE: DNA
<213> ORGANISM: Homo sapiens

<400> SEQUENCE: 101
actttaagtt tatactgagg tctatgaaga taatttattt gaagcaatat ttgaagcaat     60
gttacagtca taaaatcaaa ttgatactgt tgtatttggg cgtttctgtt agcctagtat    120
tttttttgac aagaccttg attccttttg taaacttacg cctatttttt ttccttatag    180
caaataccaa gtcgccagaa gaaaatttta gaagaagctc atgaattgag tgaagatcac    240
tataagaaat atttggcaaa actcaggtct attaatccac catgtgtgcc tttctttggt    300
aagtatttct ttctgaattt ttattgcatt tctggataaa acaaaacact catttcatta    360
aatgactgaa taattacatg tgtaatatgc cagcagaaaa tacttgtttg atcaatattt    420
agcacctgaa gccctttaga atttttctca ttaagactta aggtgaagtc taatatac    478
```

```
<210> SEQ ID NO 102
<211> LENGTH: 533
<212> TYPE: DNA
<213> ORGANISM: Homo sapiens

<400> SEQUENCE: 102
ttaagtcttt cacagatact ttctcttaag ctgctgtttt catatcatgg aaatctgagc     60
cttggttctt ttgttttggc aactgagatg gtacagtgta atatacccac aattaatgaa    120
acagaaaaaa acttgcattt tccttcttta tccttgaaat cattccatta tatcttctag    180
gaatttatct cactaatatc ttgaaaacag aagaaggcaa ccctgaggtc ctaaaaagac    240
```

```
atggaaaaga gcttataaac tttagcaaaa ggaggaaagt agcagaaata acaggagaga        300
tccagcagta ccaaaatcag ccttactgtt tacgagtaga atcagatatc aaagtaagtt        360
gaattattta aagattcata cttctgatta agtttctaaa ctacttaata aaaggcaggt        420
ttattttata ggggagaaaa agtaaaataa accttaaaag aaataattca aatttacttg        480
tattaaatgt tttcttaact ttccatgaat ttcaaactga atttataatt ttg               533
```

<210> SEQ ID NO 103
<211> LENGTH: 477
<212> TYPE: DNA
<213> ORGANISM: Homo sapiens

<400> SEQUENCE: 103

```
ttaagtttct aaactactta ataaaaggca ggtttatttt ataggggaga aaagtaaaa          60 taaaccttaa aagaaataat tcaaatttac ttgtattaaa tgttttctta actttccatg        120
aatttcaaac tgaatttata attttgaata ttaataatttt tttctttgca tttattttag      180
aggttctttg aaaacttgaa tccgatggga aatagcatgg agaaggaatt tacagattat        240
cttttcaaca aatccctaga aatagaacca cgaaaaccta agcctctccc aagatttgta        300
agcatttgta tatttgtctg gtgatgtcat tactaccata tgtgttatat agttttccat        360
aaaggtattc agggatgaag tatacatgtg atagttaaaa gtaatgaaaa agtacttaat        420
aattatgtcc aggaatatcc cacttccttc caaataaatg aatgttagta ttaattt          477
```

<210> SEQ ID NO 104
<211> LENGTH: 625
<212> TYPE: DNA
<213> ORGANISM: Homo sapiens

<400> SEQUENCE: 104

```
ggctttagca aaatagaatg ttaatgcttt aaatgttcta cttttatttg aataattatg         60
tccttattag tgatttatga ttttcctgta tattagctga attttaccag gcacatatag        120
aaaaactttc cttctactac agtgttttaa agtattgtgt ttcttttgat atgtctacag        180
ccaaaaaaat atagctatcc cctaaaatct cctggtgttc gtccatcaaa cccaagacca        240
ggtaccatga ggcatcccac acctctgcag caggagccaa ggaaaattag ttatagtagg        300
atccctgaaa gtgaaacaga aagtacagca tctgcaccaa attctccaag aacaccgtta        360
acacctccgc ctgcttctgg tgcttccagt accacagatg tttgcagtgt atttgattcc        420
gatcattcga gcccttttca ctcaagtagg tgcaaaaatt ctaagtgcat taaggtatt         480 gttagtacta tacatgctag aggtaaaaaa gaatctctgt tatttttttg tatgtgtgaa        540
cttgtagtta agtcaaatgc catttcaaaa gataatatta taaaaatata agacaaattc        600
taaactccac caacttgaaa tttct                                              625
```

<210> SEQ ID NO 105
<211> LENGTH: 443
<212> TYPE: DNA
<213> ORGANISM: Homo sapiens

<400> SEQUENCE: 105

```
atgaaatcaa gtaaagctaa aaggaatctt aaattcccaa tatgatatca ttttttttctt        60 ctcaaaagta agtagtaatg aggttttact ataaactgtt acagcattct ttaaaacgac        120
aatgacaata acattttcat cataatacaa attttttgcag atgagttgaa tatatcaatg      180
aaagaaaaaa atctactttt tcttgttttcc tttcacaggc aatgataccg tctttatcca      240
```

| | |
|---|---|
| agttactctg cccatggcc caagttagta tatttggttt aagactcata attcttgctt | 300 |
| tggctttaaa aatcaaacca agtgtaacct ttcctgctaa aactcttctt gggtctggca | 360 |
| gcattggtac cttgcttgca acatcctaga agtgaggcct tcacttgtgc tatctttaga | 420 |
| tcataagtga tttgcttaaa ttt | 443 |

<210> SEQ ID NO 106
<211> LENGTH: 479
<212> TYPE: DNA
<213> ORGANISM: Homo sapiens

<400> SEQUENCE: 106

| | |
|---|---|
| tgcatgcttt tatggcagtt tgctttaatg aaatactatt cggtattggt ttattgaaca | 60 |
| gcttttggta tttctacaca ttactttaa ttataagcaa tttccagcta agacttttca | 120 |
| aggtaaataa atgaaataaa attcctgtgg acttttctt aaaaatttaa catcccacag | 180 |
| gatctgcttc tgtatcatct ataagtttaa ccaaaggcac tgatgaagtg cctgtccctc | 240 |
| ctcctgttcc tccacgaaga cgaccagaat ctgccccagc agaatcttca ccatctaagg | 300 |
| taaagtaaga aatcttgttg tgtagaaatt ggaatcatta cagttcatta taataaacgg | 360 |
| ctgtctagtt tagttctcac taggataagt taacatttca gagtatacag cttaatagt | 420 |
| ttaaacaagg attacatata gatttagcat gcagtaatgt ttctttcttc tgaaggtag | 479 |

<210> SEQ ID NO 107
<211> LENGTH: 852
<212> TYPE: DNA
<213> ORGANISM: Homo sapiens

<400> SEQUENCE: 107

| | |
|---|---|
| aggcattgtc tcaaaaaaaa aaatttttt ttaattaaaa agaaaacata tggcaaaact | 60 |
| ccctgttcca cacttagcat cctgccaata gcatgtttga aaaccccaac ttaattctta | 120 |
| tagtcatgat acttcataaa tttattaata aatgtgtatt ttattctttt catttgttag | 180 |
| attatgtcta agcatttgga cagtccccca gccattcctc ctaggcaacc cacatcaaaa | 240 |
| gcctattcac cacgatattc aatatcagac cggacctcta tctcagaccc tcctgaaagc | 300 |
| cctcccttat taccaccacg agaacctgtg aggacacctg atgttttctc aagctcacca | 360 |
| ctacatctcc aacctccccc tttgggcaaa aaaagtgacc atggcaatgc cttcttccca | 420 |
| aacagcccctt ccccctttac accacctcct cctcaaacac cttctcctca cggcacaaga | 480 |
| aggcatctgc catcaccacc attgacacaa gaagtgacc ttcattccat tgctgggccg | 540 |
| cctgttcctc cacgacaaag cacttctcaa catatcccta aactccctcc aaaaacttac | 600 |
| aaaagggagc acacacaccc atccatgcac agagatggac caccactgtt ggagaatgcc | 660 |
| cattcttcct gagttcctct gtactgggat gtatattttc ctagccccaa atccattgct | 720 |
| ggcaatggat gcactgaatg tgccagcact gaggagttaa aatgagaact ccaaacacta | 780 |
| acgactcttc ttcaagatgc agtataagac aatgaatttt aacctagatg taattataca | 840 |
| atggaaatgg ta | 852 |

<210> SEQ ID NO 108
<211> LENGTH: 463
<212> TYPE: DNA
<213> ORGANISM: Homo sapiens

<400> SEQUENCE: 108

| | |
|---|---|
| atcttagatg gcgggagtaa gaggaaaacg attgtgaggc gggaacggct ttctgctgcc | 60 |

```
tttttttgggc ccgaaaagg gtcagctggc cgggctttgg ggcgcgtgcc ctgaggcgcg    120
gagcgcgttt gctacgatgc gggggctgct cggggctccg tccctgggc tggggacgcg     180 ccgaatgtga ccgcctcccg ctccctcacc cgccgcgggg aggaggagcg ggcgagaagc    240
tgccgccgaa cgacaggacg ttggggcggc ctggctccct caggtaggtg gcaggaccgg    300
gtcgtggatg ccggggagc cgggcggcgg ggctgaggga tcggcttcca gggcgaccgg    360
gcctgggtgg cgctgatgga gcggcccgc ggctgccggg cagagggctt gggccaggcc    420
gttgtcaccc tggggtagcg ttgggcgggg gccccggagt ccg                      463

<210> SEQ ID NO 109
<211> LENGTH: 593
<212> TYPE: DNA
<213> ORGANISM: Homo sapiens

<400> SEQUENCE: 109
tcctcatcta tgaaatattt aatggaagtg tactattaaa gaaacttttc tttgctgatg      60
aatgcaggag gtatcattaa aaacccacat agtgctattt cataattac tctttatgta     120 ttgtgttctt gggttgaata cttttgttct agagttacaa ttatttgtgt ttcttaccag    180
gtttaagaat tgtttaagct gcatcaatgg agcacataca gggagcttgg aagacgatca    240
gcaatggttt tggattcaaa gatgccgtgt ttgatggctc cagctgcatc tctcctacaa    300
tagttcagca gtttggctat cagcgccggg catcagatga tggcaaactc acagatcctt    360
ctaagacaag caacactatc cgtgttttct tgccgaacaa gcaaagaaca gtggtatgtg    420
aacattctac ttaggaaatt tagctattta tctgcctgtg gagcacatta aggatcatgt    480
tcaacttaaa gacaggcaaa atattcattg tcatttaggg tctttatttt tttttttcta    540
actgcagatt tattttttta tattgctgtt ccttccacac cccctatttt ttc            593

<210> SEQ ID NO 110
<211> LENGTH: 473
<212> TYPE: DNA
<213> ORGANISM: Homo sapiens

<400> SEQUENCE: 110
tacagatgtc tcacactcca ttcaagtact ttcctattgc tggacattca ggttgtttcg      60
tatatgtgtg tgtgcgtggg ccatcacaag caatacagac tggtgcattt atttctgtgc    120
ccacctttcc aaggggtgct gcagcctgtg ttggtcctaa aggtggtcct ttgtttgtag    180
gtcaatgtgc gaaatggaat gagcttgcat gactgcctta tgaaagcact caaggtgagg    240
ggcctgcaac cagagtgctg tgcagtgttc agacttctcc acgaacacaa agggtaagag    300
ctcaaaagtc aattgacttc ttcagactag taaggatctt ctagcttcaa atagctatgt    360
ttgtattaaa ttgtactagc ttcctataga atattgtata tttctatacc tttctttata    420
aagagataat tcagaaaaat aggtattaag aaattgaaat tattgcttgg aca            473

<210> SEQ ID NO 111
<211> LENGTH: 514
<212> TYPE: DNA
<213> ORGANISM: Homo sapiens

<400> SEQUENCE: 111
aacttgctgt gtggccttga gcaaattacc ttcttagagt cccagttttc ttatttttca      60
gatagaaata atacctactt cataggtttg ttgtatgaat taaataaatt attgttgtat    120
ggattaaata aagttgtgtt tatatggcat gtgataaatg gtagctgttg ttatttctat    180
```

| | | |
|---|---|---|
| tgaactttga tcttgtttaa acatttcatg ttttttttaa atcctttcta gtaaaaaagc | 240 | |
| acgcttagat tggaatactg atgctgcgtc tttgattgga gaagaacttc aagtagattt | 300 | |
| cctggatcat gttcccctca caacacacaa ctttgtaagt tgcagatctc ttctctttct | 360 | |
| ggcatgttga gggctttgcc aggcataaca gagatttctc aggtaaatatg cgtatgtata | 420 | |
| tatatatata gttggattgt ttaaagttct ttatgctgtt gtttacagta aggcaattta | 480 | |
| gatttcatta gtcagagata tactctaatt tgtg | 514 | |

<210> SEQ ID NO 112
<211> LENGTH: 518
<212> TYPE: DNA
<213> ORGANISM: Homo sapiens

<400> SEQUENCE: 112

| | |
|---|---|
| tacagtaagg caatttagat ttcattagtc agagatatac tctaatttgt gattatgaat | 60 |
| tctgtacatg ctggaagtat gattcatttt gtaaaaactt ttttggaggc caagaaatga | 120 |
| agttgtcttt tgtcatcttt tatttattca gcataattta cacctgtgtt cttgttgtag | 180 |
| gctcggaaga cgttcctgaa gcttgccttc tgtgacatct gtcagaaatt cctgctcaat | 240 |
| ggatttcgat gtcagacttg tggctacaaa tttcatgagc actgtagcac caaagtacct | 300 |
| actatgtgtg tggactggag taacatcaga caactcttgt aaggcattgt tcttttatcc | 360 |
| aaggaagata gggatgagga gtatacatac tttaaagggt atttgttgta gattttgact | 420 |
| gacaggtctg gattctagac tcatttaatg aattgtgatc cagaaactac tttagaaaca | 480 |
| gtgataattc tgaaactagc taggtttggt ggcattca | 518 |

<210> SEQ ID NO 113
<211> LENGTH: 505
<212> TYPE: DNA
<213> ORGANISM: Homo sapiens

<400> SEQUENCE: 113

| | |
|---|---|
| ctgtatgttt attggcaggt cagtattatt cacattcaat aatcattcaa atccagttat | 60 |
| ttggaatatt gttcccttta ttctaggtaa tgtaaaacag ttgaggaaaa tgtgactggg | 120 |
| aaaagttcag ttttagtagc tctgagtttg caaaagcaag gcatgctgat tgtctctgta | 180 |
| agattactgc aagcctaaaa accagtcttt ccctgctttt gtttagattg tttccaaatt | 240 |
| ccactattgg tgatagtgga gtcccagcac taccttcttt gactatgcgt cgtatgcgag | 300 |
| agtctgtttc caggatgcct gttaggtaat ttttaccta tagcttttct tttagaaagt | 360 |
| tatttggggt ggtggggttg aagcttgaa acaaaaaat aagagtttct tcgcattccc | 420 |
| tcctctctac gtggaaaccc cttgctgctt ctgtggaact tgatactggt ggtacagaaa | 480 |
| aggtagaaat ttctgtttat ggacc | 505 |

<210> SEQ ID NO 114
<211> LENGTH: 514
<212> TYPE: DNA
<213> ORGANISM: Homo sapiens

<400> SEQUENCE: 114

| | |
|---|---|
| aagcacctag acttaagata atttttagat gtcacacatt tgaaagaatc aaacattttg | 60 |
| tcaaaggttg tacaggtaga gtttgcccctt aagcatctta cttagtcaaa tatgtacttg | 120 |
| aaagacttca ccagtatgaa agcctaagtg ccaatcatgg aatttttcttt ctcctcctag | 180 |
| ttctcagcac agatattcta cacctcacgc cttcacctttt aacacctcca gtccctcatc | 240 |

```
tgaaggttcc ctctcccaga ggcagaggtc gacatccaca cctaatgtcc acatggtcag      300
caccaccctg cctgtggaca gcaggatgat tgaggtaata gggcacctta ggggtggtaa      360
tgtcagtcaa ttaatggggt gaggttgata cttatttcag agttttgggt ttcaaatctg      420
atcaaggaat gttgcaacac tttctcaggt ctctggactt ttacagttta ttttatatcc      480
ataatatctt cagactggct gaatagtctg gtta                                   514
```

<210> SEQ ID NO 115
<211> LENGTH: 388
<212> TYPE: DNA
<213> ORGANISM: Homo sapiens

<400> SEQUENCE: 115

```
gccactgata tttgctgaat ttaatcaagg aacgttgatt agagtatgtt taggatttct       60
atggttttta gaggttttta taatctattt tgttcttgca catcctcctc ctcttttttc      120
cctcccccag agaaaatctt ttgtgtgtag gagttgacca gctttccttt tctgtttcag      180
gatgcaattc gaagtcacag cgaatcaggt acttttccat agtcatttag ccaacaataa      240
tgggcttttt ttctttatgc ggtgtatctt ctgttggctt atccttgtgt ggcttctgtt      300
tgtcttgtct attaagcctc accttcagcc ctgtccagta gccccaacaa tctgagccca      360
acaggctggt cacagccgaa aaccccccg                                         388
```

<210> SEQ ID NO 116
<211> LENGTH: 488
<212> TYPE: DNA
<213> ORGANISM: Homo sapiens

<400> SEQUENCE: 116

```
tcttttgtgt gtaggagttg accagctttc cttttctgtt tcaggatgca attcgaagtc       60
acagcgaatc aggtactttt ccatagtcat ttagccaaca ataatgggct tttttttctt      120
atgcggtgta tcttctgttg gcttatcctt gtgtggcttc tgtttgtctt gtctattaag      180
cctcaccttc agccctgtcc agtagcccca acaatctgag cccaacaggc tggtcacagc      240
cgaaaacccc cgtgccagca caaagagagc gggcaccagt atctgggacc aggagaaaa      300 acaaaattgt gagtatagac aacagtacct cctgccaatt agggttcagt aagaaaaacc      360
tcgttggaaa ttagaatact taaacttatt ttgggagaag attctaataa aatacattca      420
atgaaggaga ttataaatgt tactgtcatt tttggcacac ttgcatcaga cagtttgcca      480
gtgctata                                                                488
```

<210> SEQ ID NO 117
<211> LENGTH: 478
<212> TYPE: DNA
<213> ORGANISM: Homo sapiens

<400> SEQUENCE: 117

```
agtttgccag tgctataact aaaatggtat ttctcaaaag acaaaaattg gaagtatggt       60
taatatgttt atctttaaaa gatatggaaa cagatgacat gggttgatcc tttgatgccc      120
tcattatcaa aagattatta ccattgcatg gagtataata atgatctcta cttgtttcag      180
aggcctcgtg gacagagaga ttcaagctat tattgggaaa tagaagccag tgaagtgatg      240
ctgtccactc ggattgggtc aggctctttt ggaactgttt ataagggtaa atggcacggt      300
aagcttgggg ccctcccttt actaactgca gggctttggt gtgaagtcaa gtttcagccc      360 aggggggccag gaggaggaga ggactgagtg ctcctgggct tatagcagta ctctccctta      420
```

```
catacttgat tatacctgaa gattgaactt aattcttttt agactaagtt cttataaa      478
```

```
<210> SEQ ID NO 118
<211> LENGTH: 445
<212> TYPE: DNA
<213> ORGANISM: Homo sapiens

<400> SEQUENCE: 118
tagcctagac aacagagtga gaccctgtct caaaaaaaaa aaaaaaattg gaaatttgcc     60
gtatctgtgt aggtatgtga ttcttttggat aaatgattca ctgtatcttc ctcaaaacta  120
ggttatttga aagactgaga tcattcaact gattgcactg actgccaact aattttgcag   180
gagatgttgc agtaaagatc ctaaaggttg tcgacccaac cccagagcaa ttccaggcct   240
tcaggaatga ggtggctgtt ctgcggtgag tagaaagctg gcggtccagt ccctctggag   300
tgctggagtg gggagtacaa ggactgtaga gttagtggac tgtgccgcag gttgggacgg   360
gcaggcagtt aggactcact gtggagtttc tgtggttgga tgctcctccc ttgagagcaa   420
agggatgttt cctttagttt atgtg                                          445
```

```
<210> SEQ ID NO 119
<211> LENGTH: 542
<212> TYPE: DNA
<213> ORGANISM: Homo sapiens

<400> SEQUENCE: 119
gcttctcttt gctcagaatg ccacccgggt tatcagccgt gccatgtgtt tgttttttggg    60 actgggggtg gtgttgggac tgggggtggt gtcgacagca cagaacccac tgtccacggg   120
aaagcacagt agacctccct gagcactttc ctcctccctc tcctctcttc ccctcccctc   180
cccagcaaaa cacggcatgt gaacattctg cttttcatgg ggtacatgac aaaggacaac   240
ctggcaattg tgacccagtg gtgcgagggc agcagcctct acaaacacct gcatgtccag   300
gagaccaagt ttcagatgtt ccagctaatt gacattgccc ggcagacggc tcagggaatg   360
gagtgagtag atggtctgat gcctctctgg gacccaggca tcaaatttgt ccctaaattg   420
gaaccaggat caggaaaagc cttctagtcc attaagcgat tctgtgatat ctttgcacaa   480
gcctctggcc tgggctggag gggccaatta tcaggaatga gttgttcagg ttccagctgg   540
gt                                                                   542
```

```
<210> SEQ ID NO 120
<211> LENGTH: 407
<212> TYPE: DNA
<213> ORGANISM: Homo sapiens

<400> SEQUENCE: 120
gtggcctcac cttcaggtaa gcagtgatgt gaaccaggct gaacagcaca gggtctatcc     60
ctgtgtgtaa cactccttgg agccaggcct tcagtggctt tacttcttag ctgtagttta   120
aaactgcttt ctactcatgc ccctcaaact tatttttaat aatttctttt cccttcacag   180
ctatttgcat gcaaagaaca tcatccatag agacatgaaa tccaacagta tcctttggtt   240
gttgagttca tttgactgct cggttctaaa tttagggaaa cagaagggag ctttctatc   300 acaagtggct ctcggtgcca ggggatatct ttttaaggaa agaggcagag gacaggaaaa   360
cagaaaagtc agaaaattag taggcttggc ctgtccctca gcagctt                  407
```

```
<210> SEQ ID NO 121
<211> LENGTH: 479
<212> TYPE: DNA
```

<213> ORGANISM: Homo sapiens

<400> SEQUENCE: 121

```
ctggaagaag gtgcatttca aaagcacttt aaagaacttc agaaaccttta ggaagttcag      60
tgcagagagg ctgtgacaga ggtaaggtgg agagattacc gtgttataaa gaactttggg     120
atatttttca aaattaacct gaccattctt ttgaaaccag agtccttaac aagcattgag     180
atatatttct ccatgaaggc ttaacagtga aaattggaga ttttggtttg gcaacagtaa     240
agtcacgctg gagtggttct cagcaggttg aacaacctac tggctctgtc ctctggatgg     300
tgagaatctg ggctcccacc agcagtctct ggtatagggc aaaaggaatg ccttggagat     360
ttatgtgcaa acttaaagcg tttctgtaca tttccccgaa atccacatga cccctagtga     420
cagccagcct cagggcaatt gtagattttc ttgaggaagc tgttgatcag aaccactgt      479
```

<210> SEQ ID NO 122
<211> LENGTH: 492
<212> TYPE: DNA
<213> ORGANISM: Homo sapiens

<400> SEQUENCE: 122

```
caaggattcc tgagctgttt taaccagtgc ctgagttgga gtcctttggg ggaaaagcta      60
tgtggggact gaagaatgga ctcattcata actaatgaaa gggacagcct ggcccctaga     120
tgtctgtgag gcctgtcata tggtgataaa tgcacttttg tcatatggtg atacatgtag     180
gccccagagg tgatccgaat gcaggataac aacccattca gtttccagtc ggatgtctac     240
tcctatggca tcgtattgta tgaactgatg acggggagc ttccttattc tcacatcaac      300
aaccgagatc aggtaagtct gtgctggtgc gaaaggaccc aactcgtggg agcccctggg     360
cctccgccag cctaagcagc tagagggtta ggacttgtta ttatctgttg ttcattcacc     420
ccccattagc tcagctgttt tctttcccctt agatcatctt catggtgggc cgaggatatg     480
cctccccaga tc                                                         492
```

<210> SEQ ID NO 123
<211> LENGTH: 495
<212> TYPE: DNA
<213> ORGANISM: Homo sapiens

<400> SEQUENCE: 123

```
gggggagctt ccttattctc acatcaacaa ccgagatcag gtaagtctgt gctggtgcga      60
aaggacccaa ctcgtgggag cccctgggcc tccgccagcc taagcagcta gagggttagg     120
acttgttatt atctgttgtt cattcacccc ccattagctc agctgttttc tttcccttag     180
atcatcttca tggtgggccg aggatatgcc tccccagatc ttagtaagct atataagaac     240
tgccccaaag caatgaagag gctggtagct gactgtgtga agaaagtaaa ggaagagagg     300
cctctttttc cccaggtaag gctcaggggct gctagaatgt gattaaagca tgggttggtt     360
cgtaaagatg gcaatataag gtgggagtgt tttgttttgt tttatagggaa ggggacccag    420
gtcctctaca agatggtggg gggcagggta catcctgtgt cttgagaca cagctaatga     480
gagcattctt gggct                                                      495
```

<210> SEQ ID NO 124
<211> LENGTH: 1409
<212> TYPE: DNA
<213> ORGANISM: Homo sapiens

<400> SEQUENCE: 124

```
agggctgcta gaatgtgatt aaagcatggg ttggttcgta agatggcaa tataaggtgg      60 gagtgttttg ttttgtttta tagggagggg acccaggtcc tctacaagat ggtgggggc    120 agggtacatc ctgtgtcttt gagacacagc taatgagagc attcttgggc tttgtttcag   180
atcctgtctt ccattgagct gctccaacac tctctaccga agatcaaccg gagcgcttcc   240
gagccatcct tgcatcgggc agcccacact gaggatatca atgcttgcac gctgaccacg   300
tccccgaggc tgcctgtctt ctagttgact ttgcacctgt cttcaggctg ccaggggagg   360
aggagaagcc agcaggcacc acttttctgc tcccttttctc cagaggcaga acacatgttt  420
tcagagaagc tgctgctaag gaccttctag actgctcaca gggccttaac ttcatgttgc   480
cttcttttct atccctttgg gccctgggag aaggaagcca tttgcagtgc tggtgtgtcc   540
tgctccctcc ccacattccc catgctcaag gcccagcctt ctgtagatgc gcaagtggat   600
gttgatggta gtacaaaaag caggggccca gccccagctg ttggctacat gagtatttag   660
aggaagtaag gtagcaggca gtccagccct gatgtggaga cacatgggat tttggaaatc   720
agcttctgga ggaatgcatg tcacaggcgg actttcttc agagagtggt gcagcgccag    780
acattttgca cataaggcac caaacagccc aggactgccg agactctggc cgcccgaagg   840
agcctgcttt ggtactatgg aactttctt aggggacacg tcctcctttc acagcttcta    900
aggtgtccag tgcattggga tggttttcca ggcaaggcac tcggccaatc cgcatctcag   960
ccctctcagg gagcagtctt ccatcatgct gaattttgtc ttccaggagc tgcccctatg  1020
gggcggggcc gcagggccag ccttgtttct ctaacaaaca aacaaacaaa cagccttgtt  1080
tctctagtca catcatgtgt atacaaggaa gccaggaata caggttttct tgatgatttg  1140
ggttttaatt ttgtttttat tgcacctgac aaaatacagt tatctgatgg tccctcaatt  1200
atgttatttt aataaaataa attaaattta ggtgtaatgg ctggctgtta cctcctttta  1260
aagtaattct gagctcacaa cttgaatgcc ccatttgttc accctcttca ggagcagaat  1320
tcaagaacag gaaatgtgcc cagagcctag gctgggaatg aatttgtaat ttaacctttg  1380
tactctttgt aaacctctac tgaagagtt                                    1409
```

<210> SEQ ID NO 125
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)
<223> OTHER INFORMATION: variable amino acid
<220> FEATURE:
<221> NAME/KEY: MOD_RES
<222> LOCATION: (4)
<223> OTHER INFORMATION: Phospho-Ser
<220> FEATURE:
<221> NAME/KEY: MOD_RES
<222> LOCATION: (5)
<223> OTHER INFORMATION: variable amino acid

<400> SEQUENCE: 125

Arg Ser Xaa Ser Xaa Pro
 1               5